United States Patent
Telfort et al.

(10) Patent No.: US 9,131,917 B2
(45) Date of Patent: *Sep. 15, 2015

(54) ACOUSTIC SENSOR ASSEMBLY

(71) Applicant: Masimo Corporation, Irvine, CA (US)

(72) Inventors: Valery G. Telfort, Montreal (CA); Predrag Pudar, Lachine (CA); Dimitar Dimitrov, Saint-Laurent (CA); Phi Trang, Montreal (CA); Ammar Al-Ali, San Juan Capistrano, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/671,367

(22) Filed: Mar. 27, 2015

(65) Prior Publication Data
US 2015/0196270 A1 Jul. 16, 2015

Related U.S. Application Data

(63) Continuation of application No. 14/259,527, filed on Apr. 23, 2014, now Pat. No. 9,028,429, which is a continuation of application No. 12/643,939, filed on Dec. 21, 2009, now Pat. No. 8,771,204.

(60) Provisional application No. 61/141,584, filed on Dec. 30, 2008, provisional application No. 61/252,076, filed on Oct. 15, 2009.

(51) Int. Cl.
*A61B 7/00* (2006.01)
*A61B 7/02* (2006.01)
*H04R 25/02* (2006.01)
(Continued)

(52) U.S. Cl.
CPC ............... *A61B 7/04* (2013.01); *A61B 5/6832* (2013.01); *A61B 5/6843* (2013.01)

(58) Field of Classification Search
CPC ........................................................ A61B 5/00
USPC ........................... 600/300, 586; 181/130, 131
See application file for complete search history.

(56) References Cited

U.S. PATENT DOCUMENTS

| | | | |
|---|---|---|---|
| 3,682,161 | A | 8/1972 | Alibert |
| 3,951,230 | A | 4/1976 | Littmann |

(Continued)

FOREIGN PATENT DOCUMENTS

| | | |
|---|---|---|
| CA | 2490438 | 1/2004 |
| CA | 2262236 | 4/2008 |

(Continued)

OTHER PUBLICATIONS

US 8,740,816, 06/2014, Telfort et al. (withdrawn).
(Continued)

*Primary Examiner* — Rene Towa
*Assistant Examiner* — May Abouelela
(74) *Attorney, Agent, or Firm* — Knobbe, Martens, Olson & Bear LLP

(57) ABSTRACT

An acoustic sensor is configured to provide accurate and robust measurement of bodily sounds under a variety of conditions, such as in noisy environments or in situations in which stress, strain, or movement may be imparted onto a sensor with respect to a patient. Embodiments of the sensor provide a conformable electrical shielding, as well as improved acoustic and mechanical coupling between the sensor and the measurement site.

21 Claims, 24 Drawing Sheets

(51) Int. Cl.
*A61B 7/04* (2006.01)
*A61B 5/00* (2006.01)

(56) References Cited

U.S. PATENT DOCUMENTS

| | | | |
|---|---|---|---|
| 4,127,749 A | 11/1978 | Atoji et al. | |
| 4,254,302 A * | 3/1981 | Walshe | 381/67 |
| 4,326,143 A | 4/1982 | Guth et al. | |
| 4,413,202 A | 11/1983 | Krempl et al. | |
| 4,537,200 A | 8/1985 | Widrow | |
| 4,576,179 A * | 3/1986 | Manus et al. | 600/484 |
| 4,578,613 A | 3/1986 | Posthuma de Boer et al. | |
| 4,634,917 A | 1/1987 | Dvorsky et al. | |
| 4,672,976 A * | 6/1987 | Kroll | 600/528 |
| 4,805,633 A * | 2/1989 | Kotani et al. | 600/528 |
| 4,827,943 A | 5/1989 | Bornn et al. | |
| 4,884,809 A | 12/1989 | Rowan | |
| 4,924,876 A | 5/1990 | Cameron | |
| 4,947,859 A * | 8/1990 | Brewer et al. | 600/528 |
| 4,960,118 A * | 10/1990 | Pennock | 128/200.24 |
| 4,960,128 A | 10/1990 | Gordon et al. | |
| 4,964,408 A | 10/1990 | Hink et al. | |
| 4,982,738 A | 1/1991 | Griebel | |
| 5,003,605 A * | 3/1991 | Phillipps et al. | 381/67 |
| 5,033,032 A | 7/1991 | Houghtaling | |
| 5,036,857 A * | 8/1991 | Semmlow et al. | 600/528 |
| 5,041,187 A | 8/1991 | Hink et al. | |
| 5,069,213 A | 12/1991 | Polczynski | |
| 5,078,151 A * | 1/1992 | Laballery | 600/528 |
| 5,140,992 A * | 8/1992 | Zuckerwar et al. | 600/528 |
| 5,143,078 A | 9/1992 | Mather et al. | |
| 5,163,438 A | 11/1992 | Gordon et al. | |
| 5,269,314 A * | 12/1993 | Kendall et al. | 600/528 |
| 5,278,627 A | 1/1994 | Aoyagi et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| 5,406,952 A * | 4/1995 | Barnes et al. | 600/485 |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,448,996 A | 9/1995 | Bellin et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,539,831 A | 7/1996 | Harley | |
| 5,561,275 A | 10/1996 | Savage et al. | |
| 5,562,002 A | 10/1996 | Lalin | |
| 5,564,108 A | 10/1996 | Hunsaker et al. | |
| 5,578,799 A * | 11/1996 | Callahan et al. | 181/137 |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,738,106 A | 4/1998 | Yamamori et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,812,678 A * | 9/1998 | Scalise et al. | 381/67 |
| 5,823,950 A | 10/1998 | Diab et al. | |
| 5,825,895 A | 10/1998 | Grasfield et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,912,656 A | 6/1999 | Tham et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,977,538 A | 11/1999 | Unger et al. | |
| 5,989,193 A | 11/1999 | Sullivan | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,083,156 A | 7/2000 | Lisiecki | |
| 6,088,607 A | 7/2000 | Diab et al. | |
| 6,106,481 A | 8/2000 | Cohen | |
| 6,110,522 A | 8/2000 | Lepper, Jr. et al. | |
| 6,124,597 A | 9/2000 | Shehada | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A * | 12/2000 | Mills et al. | 439/489 |
| 6,168,568 B1 | 1/2001 | Gavriely | |
| 6,184,521 B1 | 2/2001 | Coffin, IV et al. | |
| 6,206,830 B1 | 3/2001 | Diab et al. | |
| 6,210,344 B1 * | 4/2001 | Perin et al. | 600/528 |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,248,083 B1 | 6/2001 | Smith et al. | |
| 6,253,097 B1 | 6/2001 | Aronow et al. | |
| 6,256,523 B1 | 7/2001 | Diab et al. | |
| 6,261,237 B1 * | 7/2001 | Swanson et al. | 600/527 |
| 6,263,222 B1 | 7/2001 | Diab et al. | |
| 6,275,594 B1 * | 8/2001 | Senoo et al. | 381/114 |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,295,365 B1 | 9/2001 | Ota | |
| 6,301,493 B1 | 10/2001 | Marro et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,415,033 B1 | 7/2002 | Halleck et al. | |
| 6,423,013 B1 | 7/2002 | Bakker et al. | |
| 6,430,437 B1 | 8/2002 | Marro | |
| 6,430,525 B1 | 8/2002 | Weber et al. | |
| 6,438,238 B1 * | 8/2002 | Callahan | 381/67 |
| 6,463,311 B1 | 10/2002 | Diab | |
| 6,470,199 B1 | 10/2002 | Kopotic et al. | |
| 6,486,588 B2 | 11/2002 | Doron et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |

(56) References Cited

U.S. PATENT DOCUMENTS

| | | |
|---|---|---|
| 6,517,497 B2 | 2/2003 | Rymut et al. |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 * | 7/2003 | Cybulski et al. ............ 181/131 |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,816,744 B2 | 11/2004 | Garfield et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,937,736 B2 | 8/2005 | Toda |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,954,971 B1 * | 10/2005 | Bryant et al. ............ 29/25.35 |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,035,684 B2 | 4/2006 | Lee |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,096,060 B2 | 8/2006 | Arand et al. |
| 7,110,804 B2 * | 9/2006 | Baumer et al. .............. 600/372 |
| 7,132,641 B2 * | 11/2006 | Schulz et al. ............... 250/221 |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,246,069 B1 | 7/2007 | O'Hanlon et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,270,126 B2 | 9/2007 | Wallace et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,361,148 B2 | 4/2008 | Narimatsu |
| 7,368,855 B2 * | 5/2008 | Orten ............ 310/328 |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 * | 5/2008 | Al-Ali et al. .................... 439/77 |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,469,158 B2 | 12/2008 | Cutler et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,515,044 B2 | 4/2009 | Welch et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |

(56) References Cited

U.S. PATENT DOCUMENTS

| | | | |
|---|---|---|---|
| 7,618,375 B2 | 11/2009 | Flaherty | |
| D606,659 S | 12/2009 | Kiani et al. | |
| 7,647,083 B2 | 1/2010 | Al-Ali et al. | |
| D609,193 S | 2/2010 | Al-Ali et al. | |
| 7,662,105 B2 | 2/2010 | Hatlestad | |
| D614,305 S | 4/2010 | Al-Ali et al. | |
| RE41,317 E | 5/2010 | Parker | |
| 7,729,733 B2 | 6/2010 | Al-Ali et al. | |
| 7,734,320 B2 | 6/2010 | Al-Ali | |
| 7,761,127 B2 | 7/2010 | Al-Ali et al. | |
| 7,761,128 B2 | 7/2010 | Al-Ali et al. | |
| 7,764,982 B2 | 7/2010 | Dalke et al. | |
| D621,516 S | 8/2010 | Kiani et al. | |
| 7,783,056 B2 * | 8/2010 | Wilmink | 381/72 |
| 7,791,155 B2 | 9/2010 | Diab | |
| 7,801,581 B2 | 9/2010 | Diab | |
| 7,806,226 B2 | 10/2010 | Drummong et al. | |
| 7,822,452 B2 | 10/2010 | Schurman et al. | |
| RE41,912 E | 11/2010 | Parker | |
| 7,844,313 B2 | 11/2010 | Kiani et al. | |
| 7,844,314 B2 | 11/2010 | Al-Ali | |
| 7,844,315 B2 | 11/2010 | Al-Ali | |
| 7,860,553 B2 | 12/2010 | Govari et al. | |
| 7,865,222 B2 | 1/2011 | Weber et al. | |
| 7,873,497 B2 | 1/2011 | Weber et al. | |
| 7,880,606 B2 | 2/2011 | Al-Ali | |
| 7,880,626 B2 | 2/2011 | Al-Ali et al. | |
| 7,891,355 B2 | 2/2011 | Al-Ali et al. | |
| 7,894,868 B2 | 2/2011 | Al-Ali et al. | |
| 7,899,507 B2 | 3/2011 | Al-Ali et al. | |
| 7,899,518 B2 | 3/2011 | Trepagnier et al. | |
| 7,904,132 B2 | 3/2011 | Weber et al. | |
| 7,909,772 B2 | 3/2011 | Popov et al. | |
| 7,910,875 B2 | 3/2011 | Al-Ali | |
| 7,919,713 B2 | 4/2011 | Al-Ali et al. | |
| 7,937,128 B2 | 5/2011 | Al-Ali | |
| 7,937,129 B2 | 5/2011 | Mason et al. | |
| 7,937,130 B2 | 5/2011 | Diab et al. | |
| 7,940,937 B2 | 5/2011 | Smith | |
| 7,941,199 B2 | 5/2011 | Kiani | |
| 7,951,086 B2 | 5/2011 | Flaherty et al. | |
| 7,957,780 B2 | 6/2011 | Lamego et al. | |
| 7,962,188 B2 | 6/2011 | Kiani et al. | |
| 7,962,190 B1 | 6/2011 | Diab et al. | |
| 7,976,472 B2 | 7/2011 | Kiani | |
| 7,976,480 B2 | 7/2011 | Grajales et al. | |
| 7,988,637 B2 | 8/2011 | Diab | |
| 7,988,688 B2 | 8/2011 | Webb et al. | |
| 7,990,382 B2 | 8/2011 | Kiani | |
| 7,991,165 B2 | 8/2011 | Kassal et al. | |
| 7,991,446 B2 | 8/2011 | Al-Ali et al. | |
| 8,000,761 B2 | 8/2011 | Al-Ali | |
| 8,008,088 B2 | 8/2011 | Bellott et al. | |
| RE42,753 E | 9/2011 | Kiani-Azarbayjany et al. | |
| 8,019,400 B2 | 9/2011 | Diab et al. | |
| 8,028,701 B2 | 10/2011 | Al-Ali et al. | |
| 8,029,765 B2 | 10/2011 | Bellott et al. | |
| 8,036,728 B2 | 10/2011 | Diab et al. | |
| 8,046,040 B2 | 10/2011 | Ali et al. | |
| 8,046,041 B2 | 10/2011 | Diab et al. | |
| 8,046,042 B2 | 10/2011 | Diab et al. | |
| 8,048,040 B2 | 11/2011 | Kiani | |
| 8,050,728 B2 | 11/2011 | Al-Ali et al. | |
| 8,092,396 B2 * | 1/2012 | Bagha et al. | 600/586 |
| 8,108,039 B2 | 1/2012 | Saliga et al. | |
| RE43,169 E | 2/2012 | Parker | |
| 8,118,620 B2 | 2/2012 | Al-Ali et al. | |
| 8,121,673 B2 | 2/2012 | Tran | |
| 8,126,528 B2 | 2/2012 | Diab et al. | |
| 8,128,572 B2 | 3/2012 | Diab et al. | |
| 8,130,105 B2 | 3/2012 | Al-Ali et al. | |
| 8,145,287 B2 | 3/2012 | Diab et al. | |
| 8,150,487 B2 | 4/2012 | Diab et al. | |
| 8,175,672 B2 | 5/2012 | Parker | |
| 8,180,420 B2 | 5/2012 | Diab et al. | |
| 8,182,443 B1 | 5/2012 | Kiani | |
| 8,185,180 B2 | 5/2012 | Diab et al. | |
| 8,190,223 B2 | 5/2012 | Al-Ali et al. | |
| 8,190,227 B2 | 5/2012 | Diab et al. | |
| 8,203,438 B2 | 6/2012 | Kiani et al. | |
| 8,203,704 B2 | 6/2012 | Merritt et al. | |
| 8,224,411 B2 | 7/2012 | Al-Ali et al. | |
| 8,228,181 B2 | 7/2012 | Al-Ali et al. | |
| 8,229,533 B2 | 7/2012 | Diab et al. | |
| 8,233,955 B2 | 7/2012 | Al-Ali et al. | |
| 8,241,223 B2 | 8/2012 | Gavriely et al. | |
| 8,244,325 B2 | 8/2012 | Al-Ali et al. | |
| 8,255,026 B1 | 8/2012 | Al-Ali | |
| 8,255,027 B2 | 8/2012 | Al-Ali et al. | |
| 8,255,028 B2 | 8/2012 | Al-Ali et al. | |
| 8,260,577 B2 | 9/2012 | Weber et al. | |
| 8,265,291 B2 * | 9/2012 | Bridger et al. | 381/67 |
| 8,265,723 B1 | 9/2012 | McHale et al. | |
| 8,274,360 B2 | 9/2012 | Sampath et al. | |
| 8,275,140 B2 | 9/2012 | Smith | |
| 8,301,217 B2 | 10/2012 | Al-Ali et al. | |
| 8,310,336 B2 | 11/2012 | Muhsin et al. | |
| 8,315,683 B2 | 11/2012 | Al-Ali et al. | |
| 8,320,576 B1 * | 11/2012 | Abbruscato | 381/67 |
| RE43,860 E | 12/2012 | Parker | |
| 8,337,403 B2 | 12/2012 | Al-Ali et al. | |
| 8,346,330 B2 | 1/2013 | Lamego | |
| 8,353,842 B2 | 1/2013 | Al-Ali et al. | |
| 8,355,766 B2 | 1/2013 | MacNeish, III et al. | |
| 8,359,080 B2 | 1/2013 | Diab et al. | |
| 8,364,223 B2 | 1/2013 | Al-Ali et al. | |
| 8,364,226 B2 | 1/2013 | Diab et al. | |
| 8,374,665 B2 | 2/2013 | Lamego | |
| 8,385,995 B2 | 2/2013 | Al-ali et al. | |
| 8,385,996 B2 | 2/2013 | Smith et al. | |
| 8,388,353 B2 | 3/2013 | Kiani et al. | |
| 8,396,228 B2 * | 3/2013 | Bilan | 381/67 |
| 8,399,822 B2 | 3/2013 | Al-Ali | |
| 8,401,602 B2 | 3/2013 | Kiani | |
| 8,403,865 B2 | 3/2013 | Halperin et al. | |
| 8,405,608 B2 * | 3/2013 | Al-Ali et al. | 345/158 |
| 8,414,499 B2 | 4/2013 | Al-Ali et al. | |
| 8,418,524 B2 | 4/2013 | Al-Ali | |
| 8,423,106 B2 | 4/2013 | Lamego et al. | |
| 8,428,967 B2 | 4/2013 | Olsen et al. | |
| 8,430,817 B1 | 4/2013 | Al-Ali et al. | |
| 8,437,825 B2 | 5/2013 | Dalvi et al. | |
| 8,449,469 B2 * | 5/2013 | Banet et al. | 600/483 |
| 8,455,290 B2 | 6/2013 | Siskavich | |
| 8,457,703 B2 | 6/2013 | Al-Ali | |
| 8,457,707 B2 | 6/2013 | Kiani | |
| 8,463,349 B2 | 6/2013 | Diab et al. | |
| 8,466,286 B2 | 6/2013 | Bellot et al. | |
| 8,471,713 B2 | 6/2013 | Poeze et al. | |
| 8,473,020 B2 | 6/2013 | Kiani et al. | |
| 8,483,787 B2 | 7/2013 | Al-Ali et al. | |
| 8,489,364 B2 | 7/2013 | Weber et al. | |
| 8,498,684 B2 | 7/2013 | Weber et al. | |
| 8,509,867 B2 | 8/2013 | Workman et al. | |
| 8,515,509 B2 | 8/2013 | Bruinsma et al. | |
| 8,517,981 B2 | 8/2013 | Zornow | |
| 8,523,781 B2 | 9/2013 | Al-Ali | |
| 8,526,665 B2 | 9/2013 | Lutz et al. | |
| 8,529,301 B2 | 9/2013 | Al-Ali et al. | |
| 8,532,727 B2 | 9/2013 | Ali et al. | |
| 8,532,728 B2 | 9/2013 | Diab et al. | |
| D692,145 S | 10/2013 | Al-Ali et al. | |
| 8,547,209 B2 | 10/2013 | Kiani et al. | |
| 8,548,548 B2 | 10/2013 | Al-Ali | |
| 8,548,550 B2 | 10/2013 | Al-Ali et al. | |
| 8,560,032 B2 | 10/2013 | Al-Ali et al. | |
| 8,560,034 B1 | 10/2013 | Diab et al. | |
| 8,570,167 B2 | 10/2013 | Al-Ali | |
| 8,570,503 B2 | 10/2013 | Vo et al. | |
| 8,571,618 B1 | 10/2013 | Lamego et al. | |
| 8,571,619 B2 | 10/2013 | Al-Ali et al. | |
| 8,577,431 B2 | 11/2013 | Lamego et al. | |
| 8,584,345 B2 | 11/2013 | Al-Ali et al. | |
| 8,588,880 B2 | 11/2013 | Abdul-Hafiz et al. | |

(56) References Cited

U.S. PATENT DOCUMENTS

| | | |
|---|---|---|
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,595 B2 | 2/2014 | Basinger |
| 8,641,631 B2 | 2/2014 | Sierra et al. |
| 8,652,060 B2 | 2/2014 | Al-Ali et al. |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| RE44,823 E | 4/2014 | Parker |
| 8,690,799 B2 | 4/2014 | Telfort et al. |
| 8,702,627 B2 | 4/2014 | Telfort et al. |
| 8,715,206 B2 | 5/2014 | Telfort et al. |
| 8,755,535 B2 | 6/2014 | Telfort et al. |
| 8,771,204 B2 | 7/2014 | Telfort et al. |
| 8,790,268 B2 | 7/2014 | Al-Ali et al. |
| 8,801,613 B2 | 8/2014 | Al-Ali et al. |
| 8,821,415 B2 | 9/2014 | Al-Ali et al. |
| 8,870,792 B2 | 10/2014 | Al-Ali et al. |
| 2004/0215094 A1* | 10/2004 | Baumer et al. ............... 600/528 |
| 2004/0228494 A1* | 11/2004 | Smith ........................... 381/67 |
| 2006/0047215 A1 | 3/2006 | Newman et al. |
| 2006/0184052 A1 | 8/2006 | Iwasawa |
| 2006/0190051 A1* | 8/2006 | Gerber et al. ................. 607/41 |
| 2006/0198533 A1 | 9/2006 | Wang |
| 2007/0049837 A1 | 3/2007 | Shertukde et al. |
| 2007/0058818 A1 | 3/2007 | Yoshimine |
| 2007/0106179 A1* | 5/2007 | Bagha et al. ................. 600/586 |
| 2007/0165872 A1* | 7/2007 | Bridger et al. ................ 381/67 |
| 2007/0173730 A1 | 7/2007 | Bikko |
| 2007/0282174 A1* | 12/2007 | Sabatino ....................... 600/300 |
| 2008/0039735 A1 | 2/2008 | Hickerson |
| 2008/0076972 A1 | 3/2008 | Dorogusker et al. |
| 2008/0077026 A1 | 3/2008 | Banet et al. |
| 2008/0077435 A1 | 3/2008 | Muradia |
| 2008/0093157 A1* | 4/2008 | Drummond et al. ......... 181/131 |
| 2008/0097249 A1* | 4/2008 | Pool et al. .................... 600/586 |
| 2008/0188733 A1 | 8/2008 | Al-Ali et al. |
| 2009/0093687 A1 | 4/2009 | Telfort et al. |
| 2009/0170664 A1 | 7/2009 | Shirasaki |
| 2009/0299157 A1 | 12/2009 | Telfort et al. |
| 2009/0316925 A1 | 12/2009 | Eisenfeld et al. |
| 2010/0090901 A1 | 4/2010 | Smith et al. |
| 2010/0094096 A1 | 4/2010 | Petruzzelli et al. |
| 2011/0034831 A1* | 2/2011 | Christensen et al. ......... 600/586 |
| 2011/0125060 A1 | 5/2011 | Telfort et al. |
| 2011/0172561 A1* | 7/2011 | Kiani et al. .................. 600/586 |
| 2011/0209915 A1 | 9/2011 | Telfort et al. |
| 2011/0213273 A1 | 9/2011 | Telfort et al. |
| 2011/0288431 A1 | 11/2011 | Alshaer et al. |
| 2012/0232427 A1* | 9/2012 | Bakema et al. ............... 600/586 |
| 2012/0302920 A1* | 11/2012 | Bridger et al. ................ 600/586 |
| 2014/0081175 A1 | 3/2014 | Telfort |
| 2014/0303520 A1 | 10/2014 | Telfort et al. |
| 2014/0309559 A1 | 10/2014 | Telfort et al. |
| 2014/0371632 A1 | 12/2014 | Al-Ali et al. |
| 2015/0025406 A1 | 1/2015 | Al-Ali et al. |
| 2015/0045685 A1 | 2/2015 | Al-Ali et al. |

FOREIGN PATENT DOCUMENTS

| | | |
|---|---|---|
| CN | 201497610 | 6/2010 |
| CN | 202005761 | 10/2011 |
| EP | 0716628 | 12/1998 |
| EP | 0659058 | 1/1999 |
| EP | 0956820 A1 | 11/1999 |
| EP | 1518442 | 3/2005 |
| EP | 2 014 234 | 1/2009 |
| EP | 1207536 | 2/2010 |
| EP | 2391273 | 12/2011 |
| EP | 2488106 | 8/2012 |
| EP | 2488978 | 8/2012 |
| EP | 2710959 | 3/2014 |
| EP | 2765909 | 8/2014 |
| FR | 2 847 796 | 6/2004 |
| GB | 2358546 | 7/2001 |
| JP | S56-031742 A | 3/1961 |
| JP | S53-094482 A | 8/1978 |
| JP | 60059900 | 4/1985 |
| JP | 6214898 | 1/1987 |
| JP | 01-309872 | 12/1989 |
| JP | H04-317637 A | 11/1992 |
| JP | H07-152553 A | 6/1995 |
| JP | 10-155755 | 6/1998 |
| JP | 2001-50713 | 2/2001 |
| JP | 2003-329719 | 11/2003 |
| JP | 2005-522292 A | 7/2005 |
| JP | 2005-531230 A | 10/2005 |
| JP | 2012-513872 | 6/2012 |
| JP | 2013-508029 | 3/2013 |
| JP | 2013-508030 | 3/2013 |
| NO | 20040819 | 2/2004 |
| WO | WO 94/05207 | 3/1994 |
| WO | WO 94/13207 | 6/1994 |
| WO | WO 95/29632 | 11/1995 |
| WO | WO 99/53277 | 10/1999 |
| WO | WO 00/10462 | 3/2000 |
| WO | WO 01/34033 | 5/2001 |
| WO | WO 01/87005 | 11/2001 |
| WO | WO 01/97691 | 12/2001 |
| WO | WO 01/78059 | 3/2002 |
| WO | WO 02/024067 | 7/2002 |
| WO | WO 02/003042 | 12/2002 |
| WO | WO 03/058646 | 7/2003 |
| WO | WO 03/087737 | 10/2003 |
| WO | WO 2004/000111 | 12/2003 |
| WO | WO 2004/004411 | 1/2004 |
| WO | WO 2005/096931 | 10/2005 |
| WO | WO 2005/099562 | 10/2005 |
| WO | WO 2008/017246 | 2/2008 |
| WO | WO 2008/148172 | 12/2008 |
| WO | WO 2009/137524 | 11/2009 |
| WO | WO 2009/155593 | 12/2009 |
| WO | WO 2010/078168 | 7/2010 |
| WO | WO 2011/047211 | 4/2011 |
| WO | WO 2011/047213 | 4/2011 |
| WO | WO 2011/047216 | 8/2011 |
| WO | WO 2011/047207 | 9/2011 |
| WO | WO 2011/047209 | 3/2012 |
| WO | WO 2013/056141 | 4/2013 |

OTHER PUBLICATIONS

Analog Devices, 12-Bit Serial Input Multiplying D/A Converter, Product Data Sheet, 2000.

Avago Technologies, "HCNR200 and HCNR201, High-Linearity Analog Optocouplers," Data Sheet, Avago Technologies, Nov. 18, 2008.

Images showing tear down of a Measurement Specialties' stethoscope, Images taken on Sep. 7, 2007, in 38 pages.

Eldor et al., "A device for monitoring ventilation during anesthesia; the paratracheal audible respiratory monitor", Canadian Journal of Anesthesia, 1990, vol. 9, No. 1, p. 95-98.

Sierra et al., Monitoring Respiratory Rate Based on Tracheal Sounds. First Experiences, Proceedings of the 26th Annual Int'l Conf. of the IEEE EMBS (Sep. 2004), 317-320.

WelchAllyn OEM Technologies, ECG ASIC, ECG 3-lead, 5-lead, 12-lead and RESP Signal Processing, ECG ASIC Part No. 000.91163 (2001).

International Search Report & Written Opinion, PCT Application PCT/US2010/052758, Feb. 10, 2011; 12 pages.

International Search Report & Written Opinion, PCT Application PCT/US2010/058981, Feb. 17, 2011; 11 pages.

International Search Report and Written Opinion for PCT/US2009/042902, mailed Dec. 8, 2009.

International Search Report, PCT Application PCT/CA2003/000536, Dec. 11, 2003; 2 pages.

(56) References Cited

OTHER PUBLICATIONS

EP Office Action dated May 18, 2011 in application No. 03711767.8.
Japanese Office Action re Application No. 2007-506626, dated Mar. 1, 2011.
PCT Invitation to Pay Fees and Initial Search Report in PCT/US2010/052756, dated Oct. 5, 2011.
International Search Report & Written Opinion for PCT/US2010/052756, mailed Feb. 6, 2012; 17 pages.
PCT Invitation to Pay Fees and Initial Search Report in PCT/US2009/069287, dated Apr. 21, 2010.
International Search Report and Written Opinion issued in PCT Application No. PCT/US2009/069287, Jun. 30, 2010.
Office Action in Japanese Application No. 2011-544508 mailed Apr. 30, 2014.
EP Office Action dated Mar. 5, 2013 in application No. 10779086.7.
PCT Invitation to Pay Fees and Initial Search Report in PCT/US2010/052754, dated Mar. 15, 2011.
International Search Report and Written Opinion in PCT/US2010/052754 mailed Jul. 27, 2011.
International Preliminary Report on Patentability (IPRP) in PCT/US2010/052754, dated Apr. 26, 2012.
International Search Report and Written Opinion in PCTUS2010052760 mailed Mar. 8, 2011 in 11 pages.
International Search Report and Written Opinion in PCT/US2010/052763, mailed May 13, 2011.
International Preliminary Report on Patentability in PCT/US2010/052763 dated Apr. 17, 2012 in 9 pages.
International Search Report and Written Opinion dated Dec. 21, 2012 for PCT Application No. PCT/US2012/060084.
International Preliminary Report on Patentability dated Apr. 15, 2014 for PCT Application No. PCT/US2012/060084.
European Search Report for Application No. 13185148.7 dated Dec. 6, 2013.

* cited by examiner

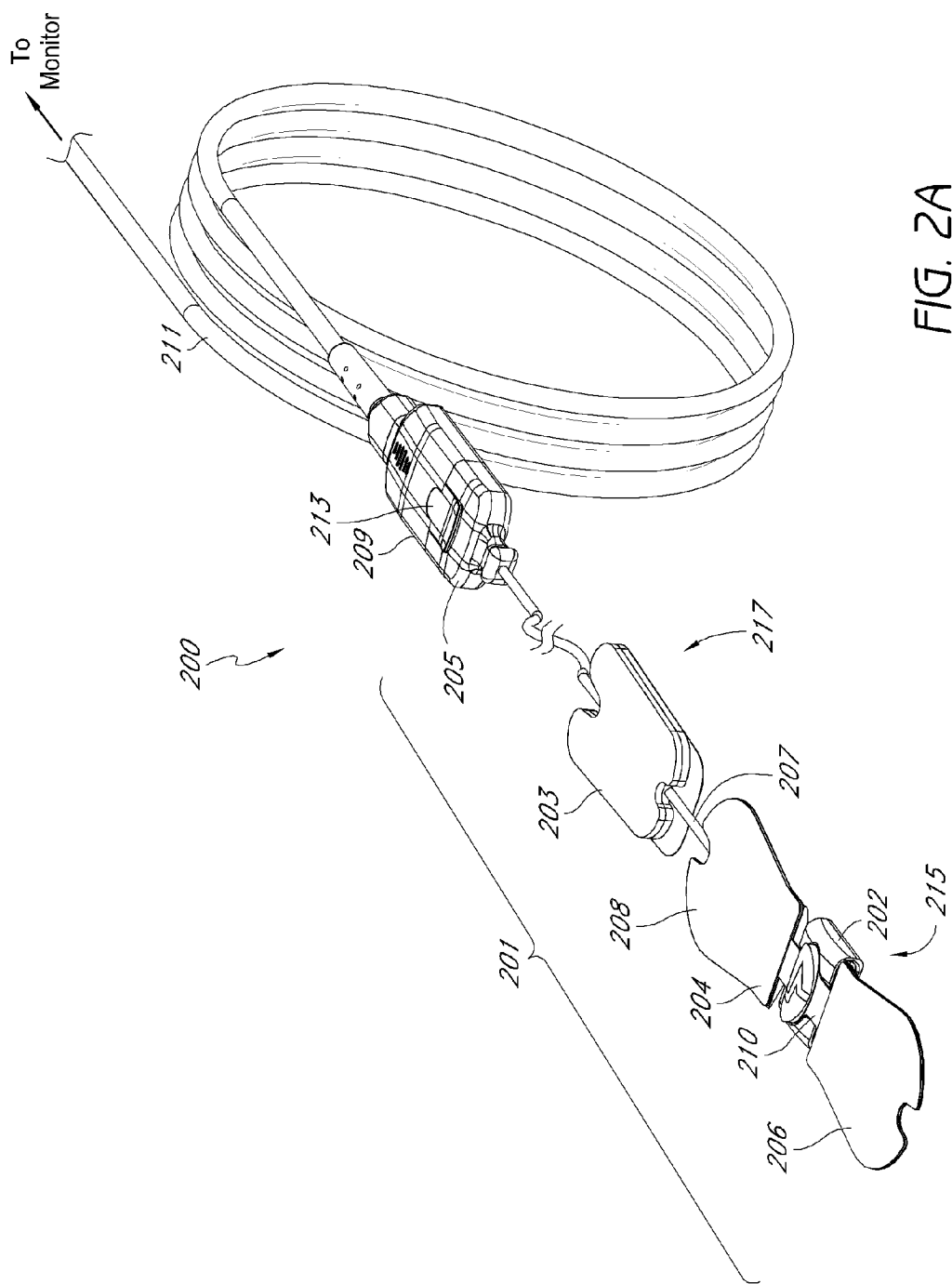

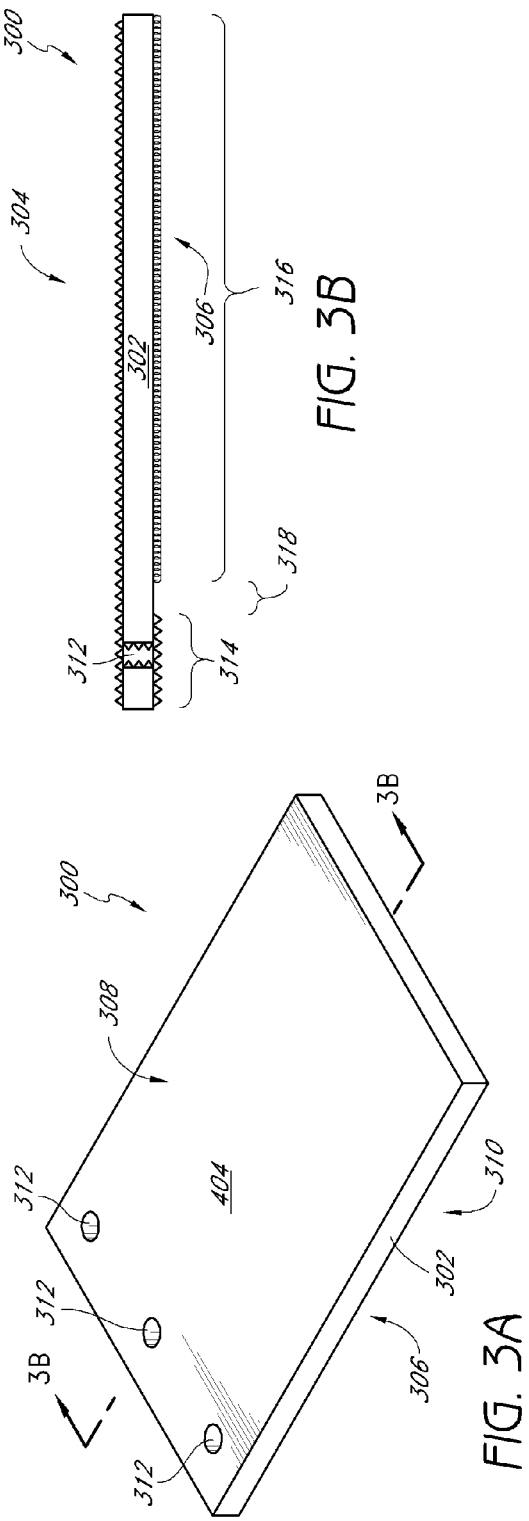
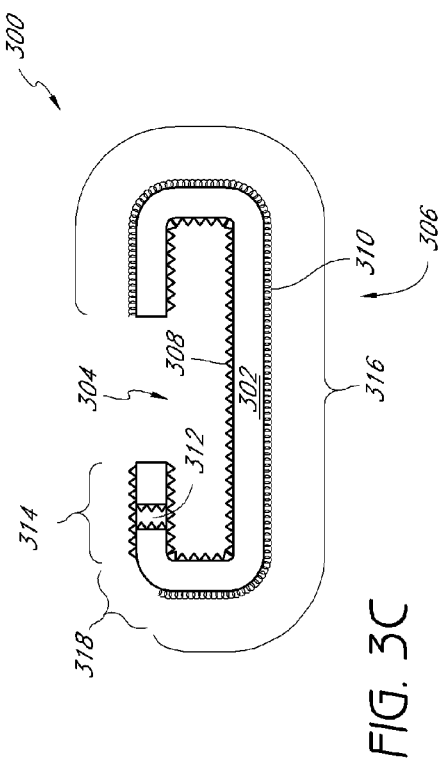
FIG. 3A
FIG. 3B
FIG. 3C

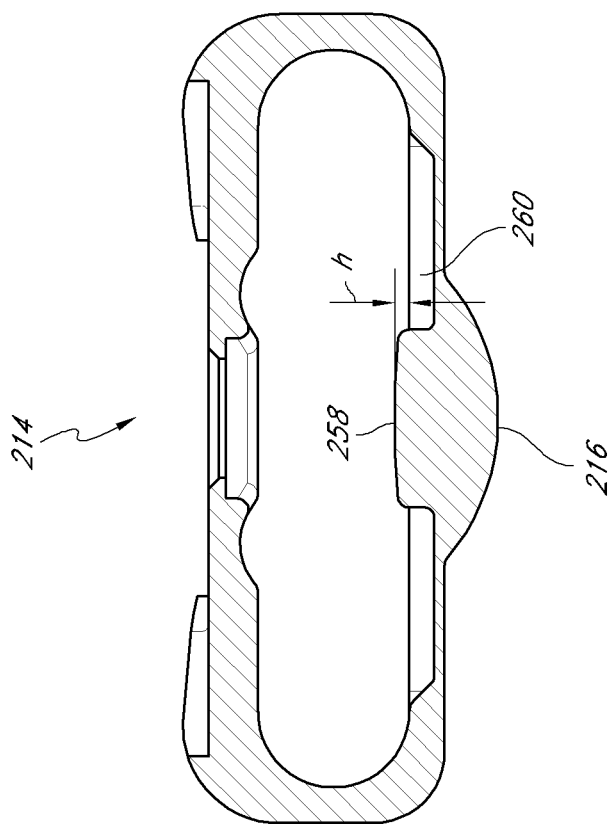

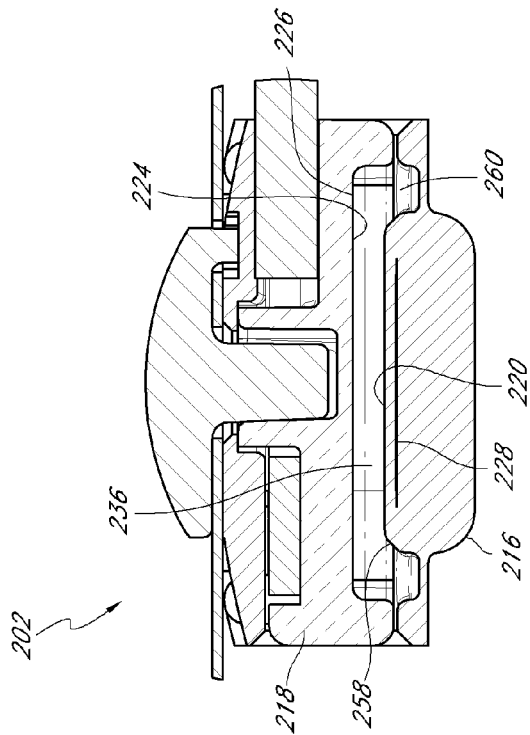
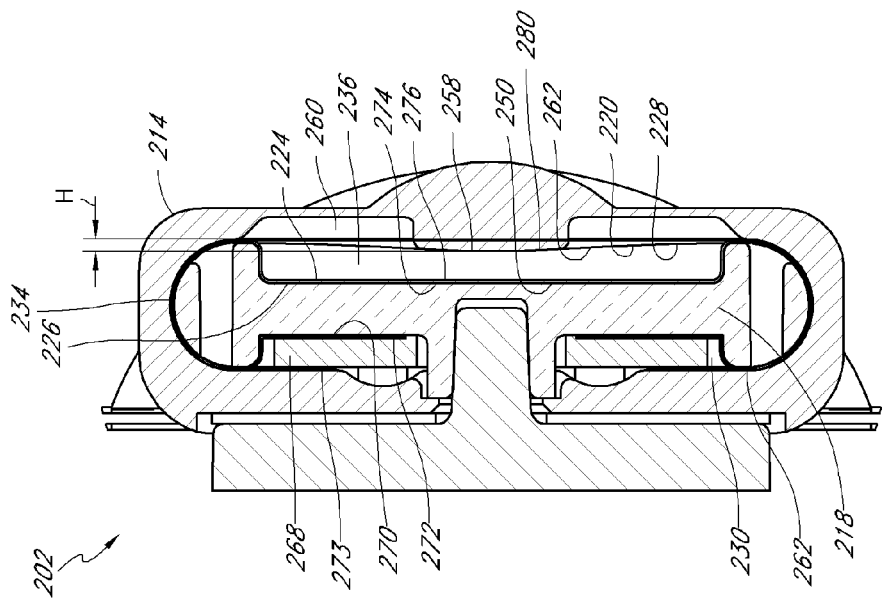
FIG. 5B
FIG. 5A

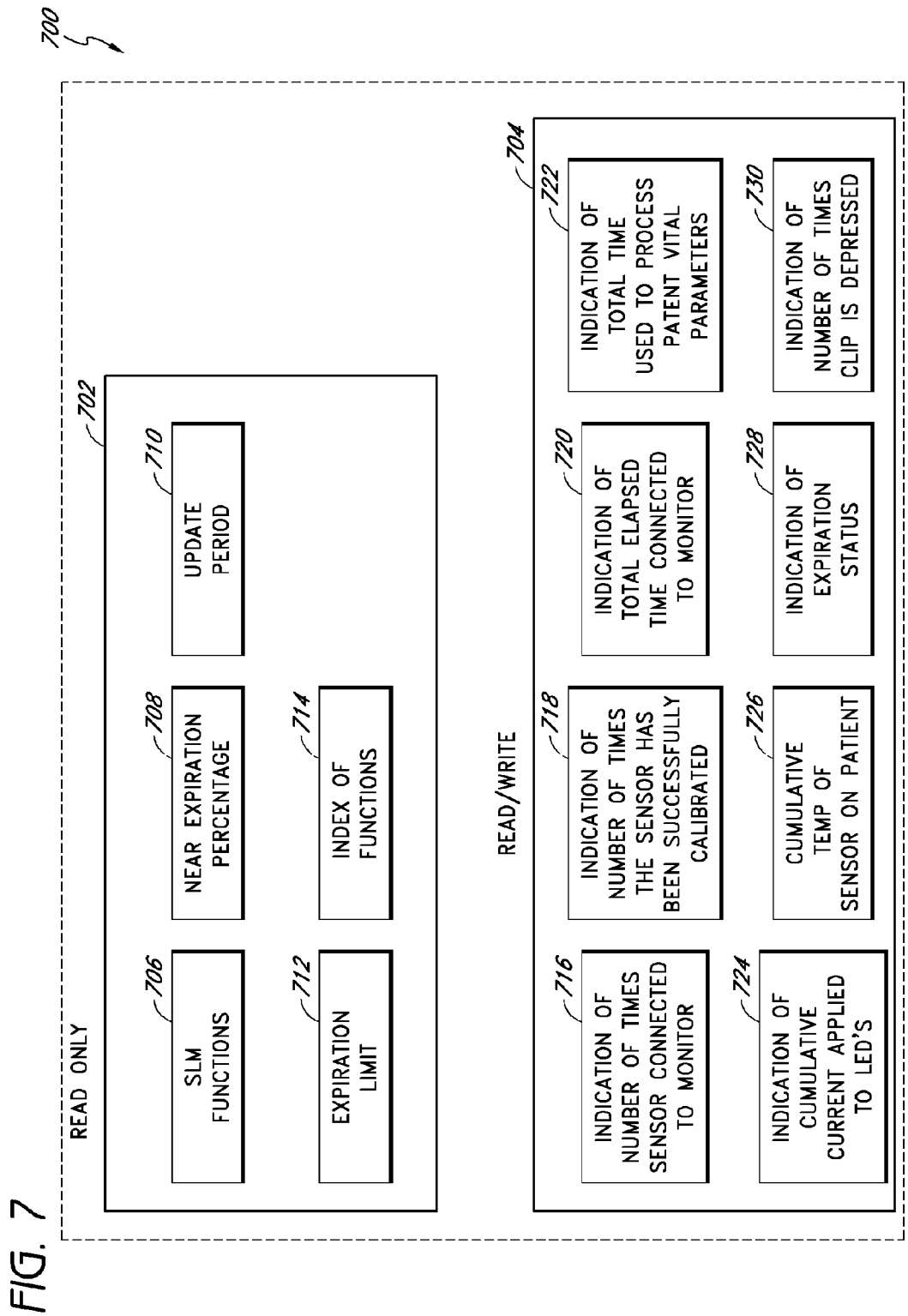

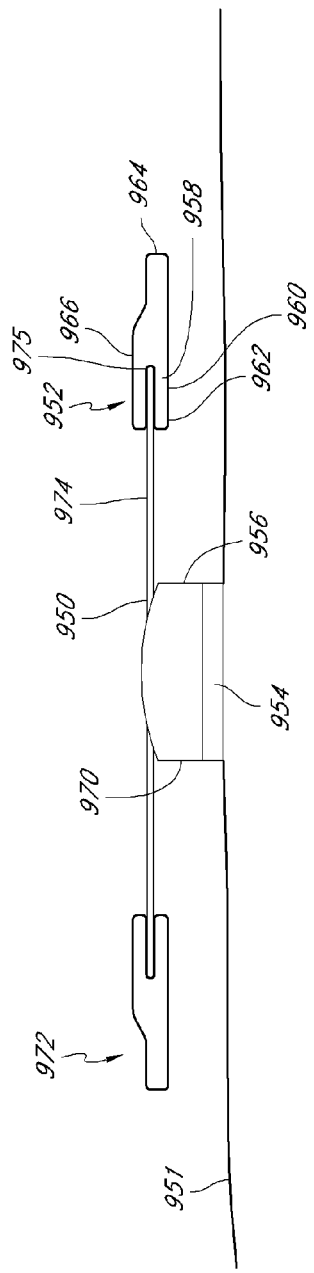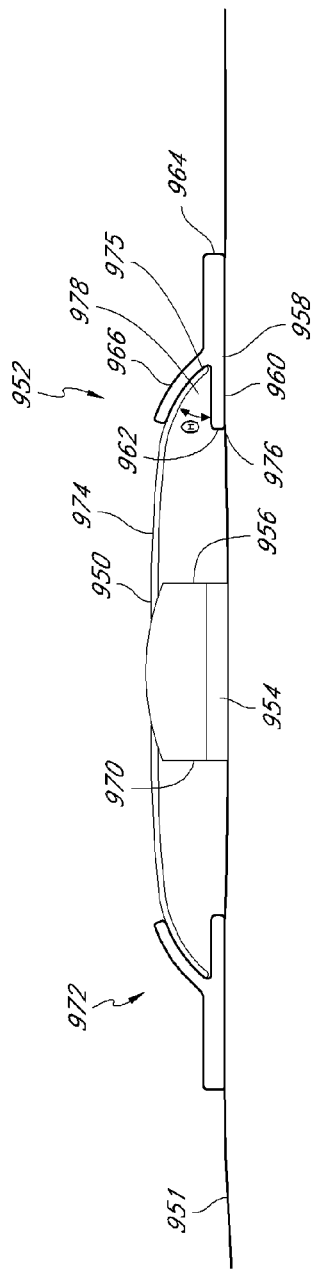

ACOUSTIC SENSOR ASSEMBLY

CROSS-REFERENCE TO RELATED APPLICATIONS

This application is a continuation of U.S. patent application Ser. No. 14/259,527, filed Apr. 23, 2014, which is a continuation of U.S. patent application Ser. No. 12/643,939, filed Dec. 21, 2009, which application claims the benefit of priority from U.S. Provisional Application Nos. 61/141,584 filed Dec. 30, 2008, and 61/252,076 filed Oct. 15, 2009. All of the above-identified applications are hereby incorporated by reference herein in their entireties and for all purposes.

BACKGROUND

1. Field

The present invention relates to non-invasive biological parameter sensing, including sensing using acoustic sensors.

2. Description of the Related Art

The "piezoelectric effect" is the appearance of an electric potential and current across certain faces of a crystal when it is subjected to mechanical stresses. Due to their capacity to convert mechanical deformation into an electric voltage, piezoelectric crystals have been broadly used in devices such as transducers, strain gauges and microphones. However, before the crystals can be used in many of these applications they must be rendered into a form which suits the requirements of the application. In many applications, especially those involving the conversion of acoustic waves into a corresponding electric signal, piezoelectric membranes have been used.

Piezoelectric membranes are typically manufactured from polyvinylidene fluoride plastic film. The film is endowed with piezoelectric properties by stretching the plastic while it is placed under a high-poling voltage. By stretching the film, the film is polarized and the molecular structure of the plastic aligned. A thin layer of conductive metal (typically nickel-copper) is deposited on each side of the film to form electrode coatings to which connectors can be attached.

Piezoelectric membranes have a number of attributes that make them interesting for use in sound detection, including: a wide frequency range of between 0.001 Hz to 1 GHz; a low acoustical impedance close to water and human tissue; a high dielectric strength; a good mechanical strength; and piezoelectric membranes are moisture resistant and inert to many chemicals.

Due in large part to the above attributes, piezoelectric membranes are particularly suited for the capture of acoustic waves and the conversion thereof into electric signals and, accordingly, have found application in the detection of body sounds. However, there is still a need for a reliable acoustic sensor particularly suited for measuring bodily sounds in noisy environments.

SUMMARY

Embodiments of an acoustic sensor described herein are configured to provide accurate and robust measurement of bodily sounds under a variety of conditions, such as in noisy environments or in situations in which stress, strain, or movement may be imparted onto sensor with respect to a patient. For example, embodiments of the sensor provide enhanced electrical shielding, improved coupling between the sensor and the measurement site, and robust physical connection between the sensor and the patient, among other advantages.

The acoustic sensor can include an electrical shielding barrier, for example, which provides for beneficial electrical shielding of a sensing element, such as a piezoelectric element of the sensor, from external electrical noises. The electrical shielding barrier can include one or more layers which form a Faraday cage around the piezoelectric element, for example, and which distribute external electrical noise substantially equally to first and second electrical poles of the piezoelectric sensing element. In addition, the shielding barrier flexibly conforms to the surface shape of the piezoelectric element as the surface shape of the piezoelectric element changes, thereby improving the shielding and sensor performance.

Embodiments of the acoustic sensor also include an acoustic coupler which advantageously improves the coupling between the source of the signal to be measured by the sensor (e.g., the patient's skin) and the sensing element. The acoustic coupler of one embodiment includes a bump positioned to apply pressure to the sensing element to bias the sensing element in tension. The acoustic coupler is further configured to transmit bodily sound waves to the sensing element. The acoustic coupler can also provide electrical isolation between the patient and the electrical components of the sensor. Such isolation can beneficially prevent potentially harmful electrical pathways or ground loops from forming and affecting the patient or the sensor.

An attachment element of the sensor may also be included which is configured to press the sensor against the patient's skin with a pre-determined amount of force. The attachment element can include an elongate member including lateral extensions symmetrically placed about the sensor such as wing-like extensions or arms that extend from the sensor. The elongate member can be made from a resilient, bendable material which rebounds readily after being bent or otherwise acts in a spring-like manner to press the sensor against the patient. The attachment element can also be configured such that movement of the sensor with respect to the attachment element does not cause the attachment element to peel off or otherwise detach from the patient during use.

In some embodiments, a cable assembly for use with an acoustic sensor includes a patient anchor which advantageously secures the sensor to the patient at a point between the ends of the cable. Securing the cable to the patient can decouple movement of the cable due to various movements such as accidental yanking or jerking on the cable or movement of the patient. Decoupling the sensor from cable movement can significantly improve performance by eliminating or reducing acoustical noise associated with cable movement. For example, by decoupling the sensor from cable movement, cable movement will not register or otherwise be introduced as noise in the acoustical signal generated by the sensor.

While some aspects of the disclosure are often described separately herein, various aspects can be combined in certain embodiment to provide synergistic results. While a variety of beneficial combinations are possible, as one example, attachment elements described herein can be used in conjunction with the acoustic couplers, e.g., to provide improved coupling between the signal and the sensor. Patient anchors and attachment elements can combine to ensure that the sensor assembly remains securely attached to the patient during use.

The sensor of certain embodiments is resposable and includes both reusable and disposable elements. For example, in certain embodiments, the sensor includes a reusable sensor portion and a disposable attachment portion. In one embodiment, the reusable elements may include those components of the sensor that are more expensive such as the sensing components and other electrical components of the sensor. The disposable elements, on the other hand, may include those components of the sensor that are relatively less expensive, such as, for example, tape portions, bandages, or other mechanisms for removably attaching the sensor to a measurement site. For example, the disposable portion may include one of the attachment elements described herein and the reusable portion may include the sensor subassemblies described herein. Additional information relating to resposable sensors compatible with embodiments described herein may be found in U.S. Pat. No. 6,920,345, filed Jan. 24, 2003, entitled "Optical Sensor Including Disposable and Reusable Elements," (hereinafter referred to as "the '345 Patent"), which is incorporated in its entirety by reference herein.

An acoustic sensor assembly is provided for non-invasively outputting a signal responsive to acoustic vibrations indicative of one or more physiological parameters of a medical patient. The sensor assembly includes a frame and a first electrical shielding layer supported by the frame. The sensor assembly can further include a sensing element configured to output a signal responsive to acoustic vibrations. In some embodiments, the sensing element comprises a piezoelectric film. The sensing element can be supported by the frame and, in certain embodiments, the first electrical shielding layer is positioned between the frame and the sensing element. The sensor assembly can also include a second electrical shielding layer supported by the frame. In some embodiments, the sensing element positioned between the second electrical shielding element and the frame. The second electrical shielding layer can also be configured to conform to a surface shape of the sensing element as the sensing element surface moves in response to said acoustic vibrations. In certain embodiments, the first electrical shielding layer is configured to conform to the surface the sensing element as the sensing element moves in response to said acoustic vibrations. Additionally, the first and second electrical shielding layers form a Faraday cage around the sensing element in some embodiments.

In certain embodiments, the sensing element comprises first and second electrical poles, and the first and second electrical shielding layers distribute electrical noise directed to the shielding element substantially equally to the first and second electrical poles. The shielding layers can be configured to distribute electrical noise substantially in phase to the first and second electrical poles, for example. In some embodiments, the sensing element and first and second shielding layers are configured to substantially shield noise by common-mode rejection. According to certain embodiments, the electrical shielding element is configured to improve noise immunity of the acoustic sensor assembly. The electrical shielding element can also be configured to lower a noise component of an output signal generated by the acoustic sensor assembly. The electrical shielding element can additionally be configured to provide an improved signal-to-noise ratio.

One or more of the first and second electrical shielding layers comprise copper in certain embodiments. One or more of the first and second electrical shielding layers can be from between about 0.5 micrometer and about 10 micrometers thick, for example. In one embodiment, one or more of the first and second electrical shielding layers are approximately 3 micrometers thick.

The acoustic sensor assembly may further include an insulating layer positioned between the sensing element and the first shielding layer. A second insulating layer can be positioned between the sensing element and the second shielding layer in some embodiments. The insulating layer can comprise an adhesive, for example.

According to another aspect of the disclosure, an acoustic sensor assembly is provided for non-invasively outputting a signal responsive to acoustic vibrations indicative of one or more physiological parameters of a medical patient. The sensor assembly includes a frame and a sensing element configured to output a signal responsive to acoustic vibrations and supported by the frame, the sensing element comprising a first electrical pole and a second electrical pole. The sensor assembly also includes an electrical shielding element supported by the frame and positioned relative to the sensing element, wherein the electrical shielding element distributes noise directed to the sensing element substantially equally to the first and second electrical poles.

According to certain embodiments, the electrical shielding element forms a faraday cage with respect to the sensing element. Additionally, the electrical shielding element can distribute a first portion of the electrical noise to the first electrical pole and a second portion of the electrical noise to the second electrical pole, wherein the first and second noise portions are substantially in phase with each other, for example. The electrical shielding element may be configured to remove noise by common-mode rejection. In some embodiments, the electrical shielding element is configured to lower a noise component of an output signal generated by the acoustic sensor assembly.

In some embodiments, the electrical shielding element includes a first layer and a second layer, and the sensing element is positioned between the first layer and the second layer. The electrical shielding element is from between about 0.5 micrometer and about 10 micrometers thick in certain embodiments. In some embodiments, the electrical shielding element is approximately 3 micrometers thick. At least a portion of the electrical shielding element conforms to a surface of the sensing element during use in certain embodiments.

In yet other embodiments, a method of manufacturing a shielded acoustic sensor includes attaching a first electrical shielding layer to a frame. The method can further include attaching a sensing layer to the frame and over the first electrical shielding layer. The method may also include attaching a second electrical shielding layer to the frame and over the sensing layer, wherein said second electrical shielding layer is configured to conform to a surface defined by the sensing layer as the sensing layer surface changes shape.

In another embodiment, a method of manufacturing a shielded acoustic sensor includes attaching a sensing element configured to output a signal responsive to acoustic vibrations to a frame, the sensing element comprising a first electrical pole and a second electrical pole. In certain embodiments, the method includes and positioning an electrical shielding element relative to the sensing element, wherein the electrical shielding element distributes noise directed to the sensing element substantially equally to the first and second electrical poles.

According to another aspect of the disclosure, an acoustic sensor assembly for non-invasively outputting a signal responsive to acoustic vibrations indicative of one or more physiological parameters of a medical patient includes a frame. The sensor assembly can also include a sensing element configured to output a signal responsive to acoustic vibrations and supported by the frame. The sensor assembly can also include and an acoustic coupler supported by the frame and positioned to apply pressure to the sensing element to bias the sensing element at a predetermined tension. The acoustic coupler can be configured to transmit acoustic vibrations to the sensing element through the acoustic coupler when the acoustic sensor assembly is attached to the medical patient.

The acoustic coupler can include an inner protrusion disposed on an inside surface of the acoustic coupler. In some embodiments, the acoustic coupler further comprises an outer protrusion disposed on an outside surface of the acoustic coupler.

Additionally, the acoustic coupler can electrically insulate the acoustic sensing element from the medical patient when the acoustic sensor assembly is attached to the medical patient. According to some embodiments, the acoustic coupler electrically isolates the acoustic sensing element from the medical patient when the acoustic sensor assembly is attached to the medical patient. The acoustic coupler comprises an elastomer in some embodiments.

The acoustic coupler can be configured to substantially evenly distribute pressure on the sensing element, for example. The sensing element can comprises a piezoelectric material. In certain embodiments, the acoustic coupler comprises a gel. The gel according to some embodiments provides acoustic impedance matching between a measurement site of the patient and the sensing element.

The acoustic sensor assembly may further include an information element supported by the frame. The information element is configured to store one or more of sensor use information, sensor compatibility information, and sensor calibration information, for example. The acoustic sensor assembly can further include a cable in communication with the sensing element and a connector attached to the cable, wherein the information element is supported by the connector. In some embodiments, the information element comprises one or more memory devices. The acoustic sensor assembly can further include an attachment element configured to apply a predetermined force to the frame during use, further improving the coupling between the signal and the sensing element.

A method of manufacturing an acoustic sensor is provided in certain embodiments. The method can include providing an acoustic coupler, a sensing element, and a frame, the frame defining an open cavity. The method can further include attaching the sensing element to the frame such that the sensing layer extends across the open cavity. In certain embodiments, the method also include attaching the acoustic coupler to the frame. The acoustic coupler applies pressure to the sensing element to bias the sensing element at a predetermined tension, for example. Additionally, the acoustic coupler is configured to transmit acoustic vibrations to the sensing element through the acoustic coupler when the acoustic sensor assembly is attached to a medical patient.

In another embodiment, a method of non-invasively outputting a signal responsive to acoustic vibrations indicative of one or more physiological parameters of a medical patient includes providing an acoustic sensor, the acoustic sensor comprising a frame, a sensing element configured to detect acoustic vibrations and supported by the frame, and an acoustic coupler supported by the frame and positioned to apply pressure to the sensing element so as to bias the sensing element to a predetermined tension prior to attachment to a medical patient. The method can further include attaching the acoustic sensor to the medical patient wherein the acoustic coupler is placed in contact with the medical patient. The method can further include outputting a signal responsive to acoustic vibrations indicative of a physiological parameter of the medical patient based on acoustic vibrations transmitted through the acoustic coupler and detected by the sensing element. In some embodiments, the attaching further includes using an attachment assembly of the acoustic sensor configured to apply a predetermined force to the frame, wherein the acoustic sensor is pressed against the medical patient.

In another embodiment, an acoustic sensor assembly is provided for non-invasively outputting a signal responsive to acoustic vibrations indicative of one or more physiological parameters of a medical patient, including a frame and a sensing element supported by the frame and configured to detect acoustic vibrations from the medical patient and provide an output signal indicative of the acoustic vibrations. The sensor assembly can further include an elongate member supported by the frame, the elongate member comprising a spring portion extending at least partially beyond opposite sides of the frame. The elongate member can be configured to apply a predetermined force to the frame with the spring portion, wherein the acoustic sensor assembly is pressed against a measurement site of the medical patient when the acoustic sensor assembly is attached to the medical patient. The predetermined force can be determined at least in part based upon a stiffness of the spring portion.

The elongate member is substantially flat when the acoustic sensor assembly is not attached to the medical patient in some embodiments. Additionally, the elongate member may bend away from the frame when the acoustic sensor assembly is not attached to the medical patient.

In certain embodiments, the frame can include a top surface and a bottom surface, the sensing element extending across the bottom surface, and the elongate member extending across and beyond the top surface. The elongate member can be coupled to a middle portion of the frame, for example. In some embodiments, the acoustic sensor assembly further includes a dielectric material supported by the frame and positioned between the frame and the elongate member. Additionally, the elongate member may be configured to apply continuous force on the frame to press it into the medical patient's skin as the medical patient's skin stretches.

The elongate member according to some embodiments further includes an attachment portion configured to attach the acoustic sensor assembly to the patient. The attachment portion comprises an adhesive, for example. The elongate member can be removably coupled to the frame, be disposable and/or have a forked shape according to various embodiments.

An acoustic sensor assembly is provided for non-invasively outputting a signal responsive to acoustic vibrations indicative of one or more physiological parameters of a medical patient. The sensor assembly includes a frame and a sensing element supported by the frame. The sensor assembly can be configured to provide a signal indicative of acoustic vibrations detected by the sensing element. The sensor assembly can further include an attachment element supported by the frame, including an attachment layer, configured to secure the acoustic sensor assembly to the medical patient. The attachment element may further include an elongate member comprising a resilient material wherein the elongate member is movably coupled to the attachment layer. The elongate member can be configured to move from a first position in which the elongate member is substantially parallel to the attachment layer to a second position in which the elongate member is inclined at an angle with respect to the attachment layer when the attachment layer is attached to the medical patient.

An end of the elongate member is positioned a predetermined distance from an edge of the attachment layer in some embodiments. The end of the elongate member can be positioned near the attachment layer's center, for example. The elongate member can be connected to the attachment layer wherein movement of the frame with respect to the attachment layer does not cause the attachment layer to detach from the medical patient during use. The elongate member may be configured to apply a predetermined force on the frame to press the acoustic sensor assembly against a measurement site of the medical patient during use, for example. In certain embodiments, the attachment layer comprises an adhesive. The attachment element can also be removably coupled to the frame. In certain embodiments, the attachment element is disposable, for example. In one embodiment, the elongate member comprises a forked shape.

In another aspect of the disclosure, a method of attaching an acoustic sensor assembly for non-invasively sensing one or more physiological parameters to a medical patient includes providing an acoustic sensor assembly comprising a frame. The sensor assembly can also include a sensing element supported by the frame. The elongate member can be supported by the frame and can include a spring portion extending at least partially beyond opposite sides of the frame. The method can further include attaching the acoustic sensor assembly to a medical patient by attaching the elongate member to the medical patient's skin. The method can also include applying a predetermined force to the frame with the spring portion, wherein the acoustic sensor assembly is pressed against the medical patient's skin, wherein the predetermined force is determined at least in part based upon a stiffness of the spring portion.

In yet another embodiment, a method of attaching an acoustic sensor assembly for non-invasively sensing one or more physiological parameters to a medical patient can includes providing an acoustic sensor assembly comprising a frame, a sensing element supported by the frame, and an attachment element supported by the frame. The attachment element can include an attachment layer which can be configured to secure the acoustic sensor assembly to the medical patient. An elongate member can be included comprising a resilient material and coupled to the attachment layer. The method can also include attaching the acoustic sensor assembly to a medical patient by attaching the attachment layer to the medical patient's skin. The attaching of the attachment layer can include bending the elongate member from a first position in which the elongate member is substantially parallel to the attachment layer to a second position in which the elongate member is inclined at an angle with respect to the attachment layer.

In another embodiment, an acoustic sensor assembly is provided including a frame and a sensing element, supported by the frame. The sensor assembly can further include a resilient backbone extending across and beyond opposite sides of the frame. An attachment element can be provided at outside ends of said backbone can include top and bottom portions. The top portion can be attached to the backbone, and the bottom portion can be configured to attach to a medical patient, for example. The top portion can also be configured to be inclined with respect to said bottom portion when attached to said medical patient.

In another embodiment, a cable assembly for use with a sensor configured to sense one or more physiological parameters of a medical patient is provided. The cable assembly can include a connector and a cable, for example. The cable can have a proximal end attached to the connector and a distal end. The distal end can be configured to attach to a sensor adapted to output a signal responsive to acoustic vibrations from a medical patient. The cable assembly can also include a patient anchor attached to the cable between the proximal end and the distal end. The patient anchor can be configured to attach to the patient at an anchoring site and to secure the cable to the patient with respect to the anchoring site, for example.

The patient anchor can be configured to decouple movement of the cable proximal end from the cable distal end when the patient anchor is attached to the patient. Additionally, the cable can further include a bent portion located at the patient anchor. The bent portion forms an "S" shape in some embodiments. The patient anchor comprises an adhesive in some embodiments. The cable assembly can also be removably coupled to the sensor. The patient anchor can be configured to be attached to the medical patient's neck.

In another embodiment, a method of securing a non-invasive physiological sensor to a measurement site on a medical patient includes providing a sensor assembly. The sensor assembly can have a sensor and a cable, for example. The sensor can also have a patient attachment portion. The cable may have first end, a second end, and an anchor located between the first and second ends. The method can further include attaching the sensor to a measurement site on the medical patient with the patient attachment portion. The method of certain embodiments also includes attaching the cable to an anchoring site on the medical patient with the anchor. The attaching the sensor can include attaching the sensor to the measurement site with an adhesive located on the patient attachment portion. Additionally, the attaching the cable can include attaching the cable to the anchoring site with an adhesive located on the anchor.

BRIEF DESCRIPTION OF THE DRAWINGS

FIG. 2A is a top perspective view illustrating portions of a sensor assembly in accordance with an embodiment of the disclosure;

FIG. 3A a perspective view of a sensing element according to an embodiment of the disclosure usable with the sensor assembly of FIG. 2A;

FIG. 3B is a cross-sectional view of the sensing element of FIG. 3A along the line 3B-3B;

FIG. 3C is a cross-sectional view of the sensing element of FIGS. 3A-B shown in a wrapped configuration;

FIG. 4 is a cross-sectional view of the coupler of FIGS. 2A-2E taken along the line 4-4 shown in FIG. 2D;

FIG. 5A-B are cross-sectional views of the sensor subassembly of FIGS. 2-3 along the lines 5A-5A and 5B-5B, respectively;

FIG. 7 illustrates a block diagram of an information element according to embodiments of the disclosure;

FIGS. 9C-D show an embodiment of a attachment subassembly when unattached and attached to a measurement site, respectively;

DETAILED DESCRIPTION

Various embodiments will be described hereinafter with reference to the accompanying drawings. These embodiments are illustrated and described by example only, and are not intended to be limiting.

In various embodiments, an acoustic sensor configured to operate with a physiological monitoring system includes an acoustic signal processing system that measures and/or determines any of a variety of physiological parameters of a medical patient. For example, in an embodiment, the physiological monitoring system includes an acoustic monitor. For example, the acoustic monitor may be an acoustic respiratory monitor which can determine any of a variety of respiratory parameters of a patient, including respiratory rate, expiratory flow, tidal volume, minute volume, apnea duration, breath sounds, riles, rhonchi, stridor, and changes in breath sounds such as decreased volume or change in airflow. In addition, in some cases the acoustic signal processing system monitors other physiological sounds, such as heart rate to help with probe off detection, heart sounds (S1, S2, S3, S4, and murmurs), and change in heart sounds such as normal to murmur or split heart sounds indicating fluid overload. Moreover, the acoustic signal processing system may (1) use a second probe over the chest for additional heart sound detection; (2) keep the user inputs to a minimum (example, height); and/or (3) use a Health Level 7 (HL7) interface to automatically input patient demography.

In certain embodiments, the physiological monitoring system includes an electrocardiograph (ECG or EKG) that measures and/or determines electrical signals generated by the cardiac system of a patient. The ECG includes one or more sensors for measuring the electrical signals. In some embodiments, the electrical signals are obtained using the same sensors used to obtain acoustic signals.

In still other embodiments, the physiological monitoring system includes one or more additional sensors used to determine other desired physiological parameters. For example, in some embodiments, a photoplethysmograph sensor determines the concentrations of analytes contained in the patient's blood, such as oxyhemoglobin, carboxyhemoglobin, methemoglobin, other dyshemoglobins, total hemoglobin, fractional oxygen saturation, glucose, bilirubin, and/or other analytes. In other embodiments, a capnograph determines the carbon dioxide content in inspired and expired air from a patient. In other embodiments, other sensors determine blood pressure, pressure sensors, flow rate, air flow, and fluid flow (first derivative of pressure). Other sensors may include a pneumotachometer for measuring air flow and a respiratory effort belt. In certain embodiments, these sensors are combined in a single processing system which processes signal output from the sensors on a single multi-function circuit board.

Figure 1A:
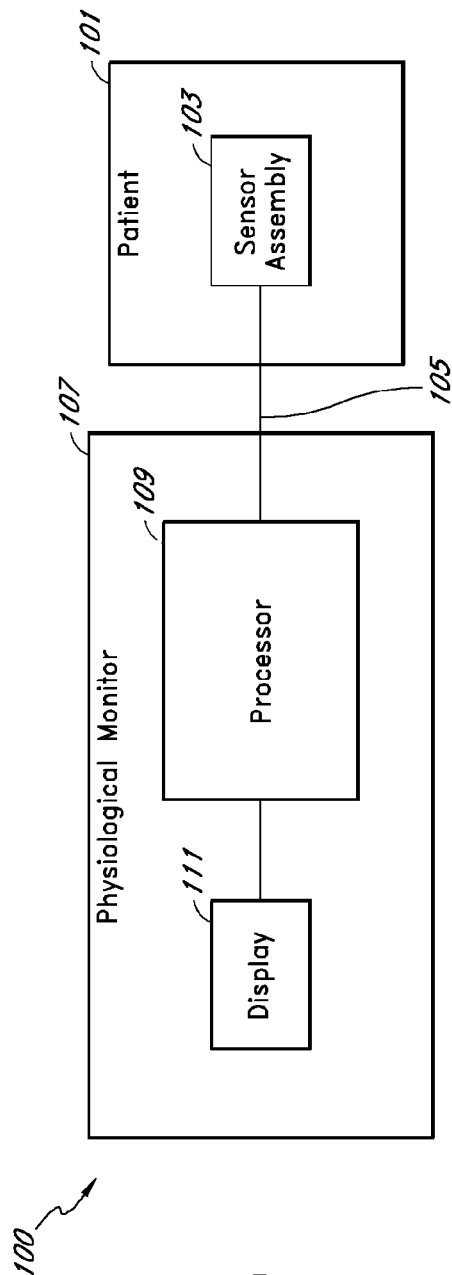
FIGS. 1A-B are block diagrams illustrating physiological monitoring systems in accordance with embodiments of the disclosure.

FIG. 1A illustrates an embodiment of a physiological monitoring system 100. A medical patient 101 is monitored using one or more sensor assemblies 103, each of which transmits a signal over a cable 105 or other communication link or medium to a physiological monitor 107. The physiological monitor 107 includes a processor 109 and, optionally, a display 111. The one or more sensors 103 include sensing elements such as, for example, acoustic piezoelectric devices, electrical ECG leads, or the like. The sensors 103 generate respective signals by measuring a physiological parameter of the patient 101. The signal is then processed by one or more processors 109. The one or more processors 109 then communicate the processed signal to the display 111. In an embodiment, the display 111 is incorporated in the physiological monitor 107. In another embodiment, the display 111 is separate from the physiological monitor 107. In one embodiment, the monitoring system 100 is a portable monitoring system.

For clarity, a single block is used to illustrate the one or more sensors 103 shown in FIG. 1A. It should be understood that the sensor 103 block shown is intended to represent one or more sensors. In an embodiment, the one or more sensors 103 include a single sensor of one of the types described below. In another embodiment, the one or more sensors 103 include at least two acoustic sensors. In still another embodiment, the one or more sensors 103 include at least two acoustic sensors and one or more ECG sensors. In each of the foregoing embodiments, additional sensors of different types are also optionally included. Other combinations of numbers and types of sensors are also suitable for use with the physiological monitoring system 100.

In some embodiments of the system shown in FIG. 1A, all of the hardware used to receive and process signals from the sensors are housed within the same housing. In other embodiments, some of the hardware used to receive and process signals is housed within a separate housing. In addition, the physiological monitor 107 of certain embodiments includes hardware, software, or both hardware and software, whether in one housing or multiple housings, used to receive and process the signals transmitted by the sensors 103.

Figure 1B:
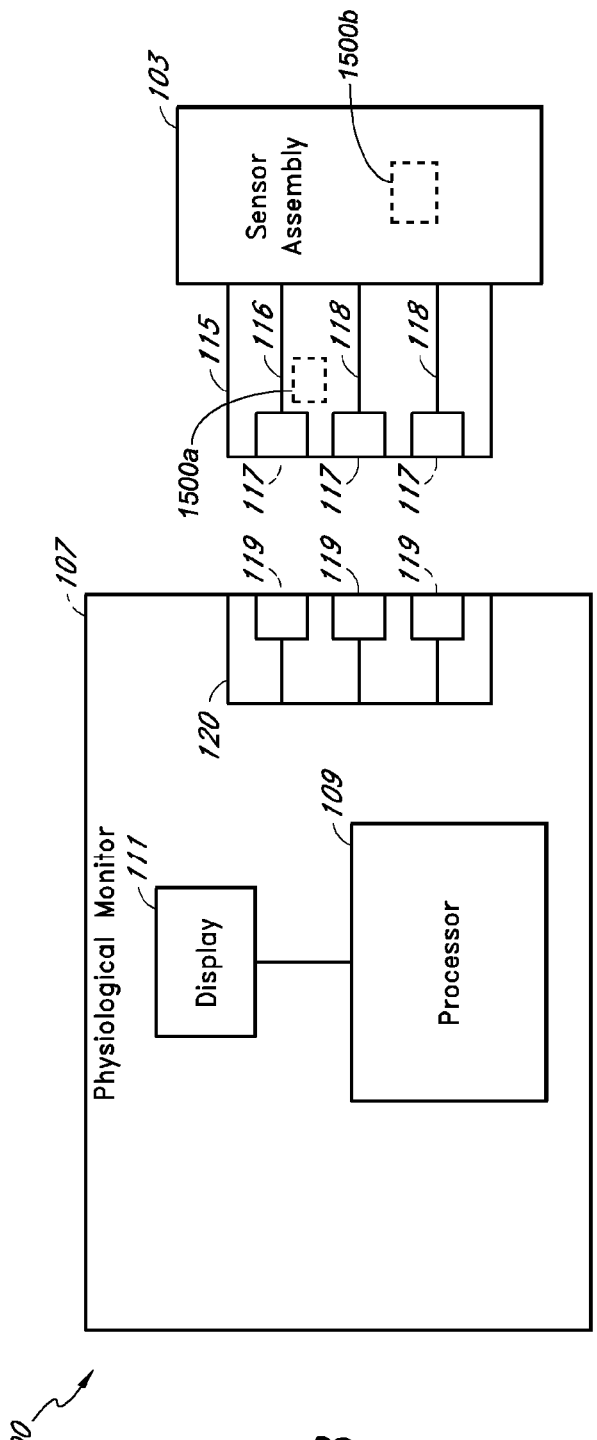

As shown in FIG. 1B, the acoustic sensor assembly 103 can include a cable 115 or lead. The cable 115 typically carries three conductors within an electrical shielding: one conductor 116 to provide power to a physiological monitor 107, one conductor 118 to provide a ground signal to the physiological monitor 107, and one conductor 118 to transmit signals from the sensor 103 to the physiological monitor 107. In some embodiments, the "ground signal" is an earth ground, but in other embodiments, the "ground signal" is a patient ground, sometimes referred to as a patient reference, a patient reference signal, a return, or a patient return. In some embodiments, the cable 115 carries two conductors within an electrical shielding layer, and the shielding layer acts as the ground conductor. Electrical interfaces 117 in the cable 115 enable the cable to electrically connect to electrical interfaces 119 in a connector 120 of the physiological monitor 107. In another embodiment, the sensor assembly 103 and the physiological monitor 107 communicate wirelessly. Additional information relating to acoustic sensors compatible with embodiments described herein, including other embodiments of interfaces with the physiological monitor, are included in U.S. patent application Ser. No. 12/044,883, filed Mar. 7, 2008, entitled "Systems and Methods for Determining a Physiological Condition Using an Acoustic Monitor," (hereinafter referred to as "the '883 Application") which is incorporated in its entirety by reference herein.

FIG. 2A is a top perspective of a sensor system 200 including a sensor assembly 201 suitable for use with any of the physiological monitors shown in FIGS. 1A-C and a monitor cable 211. The sensor assembly 201 includes a sensor 215, a cable assembly 217 and a connector 205. The sensor 215, in one embodiment, includes a sensor subassembly 202 and an attachment subassembly 204. The cable assembly 217 of one embodiment includes a cable 207 and a patient anchor 203. The various components are connected to one another via the sensor cable 207. The sensor connector subassembly 205 can be removably attached to monitor connector 209 which is connected to physiological monitor (not shown) through the monitor cable 211. In one embodiment, the sensor assembly 201 communicates with the physiological monitor wirelessly. In various embodiments, not all of the components illustrated in FIG. 2A are included in the sensor system 200. For example, in various embodiments, one or more of the patient anchor 203 and the attachment subassembly 204 are not included. In one embodiment, for example, a bandage or tape is used instead of the attachment subassembly 204 to attach the sensor subassembly 202 to the measurement site. Moreover, such bandages or tapes may be a variety of different shapes including generally elongate, circular and oval, for example.

The sensor connector subassembly 205 and monitor connector 209 may be advantageously configured to allow the sensor connector 205 to be straightforwardly and efficiently joined with and detached from the monitor connector 209. Embodiments of sensor and monitor connectors having similar connection mechanisms are described in U.S. patent application Ser. No. 12/248,856 (hereinafter referred to as "the '856 Application"), filed on Oct. 9, 2008, which is incorporated in its entirety by reference herein. For example, the sensor connector 205 includes a mating feature 213 which mates with a corresponding feature (not shown) on the monitor connector 209. The mating feature 213 may include a protrusion which engages in a snap fit with a recess on the monitor connector 209. In certain embodiments, the sensor connector 205 can be detached via one hand operation, for example. Examples of connection mechanisms may be found specifically in paragraphs [0042], [0050], [0051], [0061]-[0068] and [0079], and with respect to FIGS. 8A-F, 13A-E, 19A-F, 23A-D and 24A-C of the '856 Application, for example. The sensor system 200 measures one or more physiological parameters of the patient, such as one of the physiological parameters described above.

The sensor connector subassembly 205 and monitor connector 209 may advantageously reduce the amount of unshielded area in and generally provide enhanced shielding of the electrical connection between the sensor and monitor in certain embodiments. Examples of such shielding mechanisms are disclosed in the '856 Application in paragraphs [0043]-[0053], [0060] and with respect to FIGS. 9A-C, 11A-E, 13A-E, 14A-B, 15A-C, and 16A-E, for example.

As will be described in greater detail herein, in an embodiment, the acoustic sensor assembly 201 includes a sensing element, such as, for example, a piezoelectric device or other acoustic sensing device. The sensing element generates a voltage that is responsive to vibrations generated by the patient, and the sensor includes circuitry to transmit the voltage generated by the sensing element to a processor for processing. In an embodiment, the acoustic sensor assembly 201 includes circuitry for detecting and transmitting information related to biological sounds to a physiological monitor. These biological sounds may include heart, breathing, and/or digestive system sounds, in addition to many other physiological phenomena. The acoustic sensor 215 in certain embodiments is a biological sound sensor, such as the sensors described herein. In some embodiments, the biological sound sensor is one of the sensors such as those described in the '883 Application. In other embodiments, the acoustic sensor 215 is a biological sound sensor such as those described in U.S. Pat. No. 6,661,161, which is incorporated by reference herein. Other embodiments include other suitable acoustic sensors.

The attachment sub-assembly 204 includes first and second elongate portions 206, 208. The first and second elongate portions 206, 208 can include patient adhesive (e.g., in some embodiments, tape, glue, a suction device, etc.) attached to a elongate member 210. The adhesive on the elongate portions 206, 208 can be used to secure the sensor subassembly 202 to a patient's skin. As will be discussed in greater detail herein, the elongate member 210 can beneficially bias the sensor subassembly 202 in tension against the patient's skin and reduce stress on the connection between the patient adhesive and the skin. A removable backing can be provided with the patient adhesive to protect the adhesive surface prior to affixing to a patient's skin.

The sensor cable 207 is electrically coupled to the sensor subassembly 202 via a printed circuit board ("PCB") (not shown) in the sensor subassembly 202. Through this contact, electrical signals are communicated from the multi-parameter sensor subassembly to the physiological monitor through the sensor cable 207 and the cable 211.

Figure 2B:
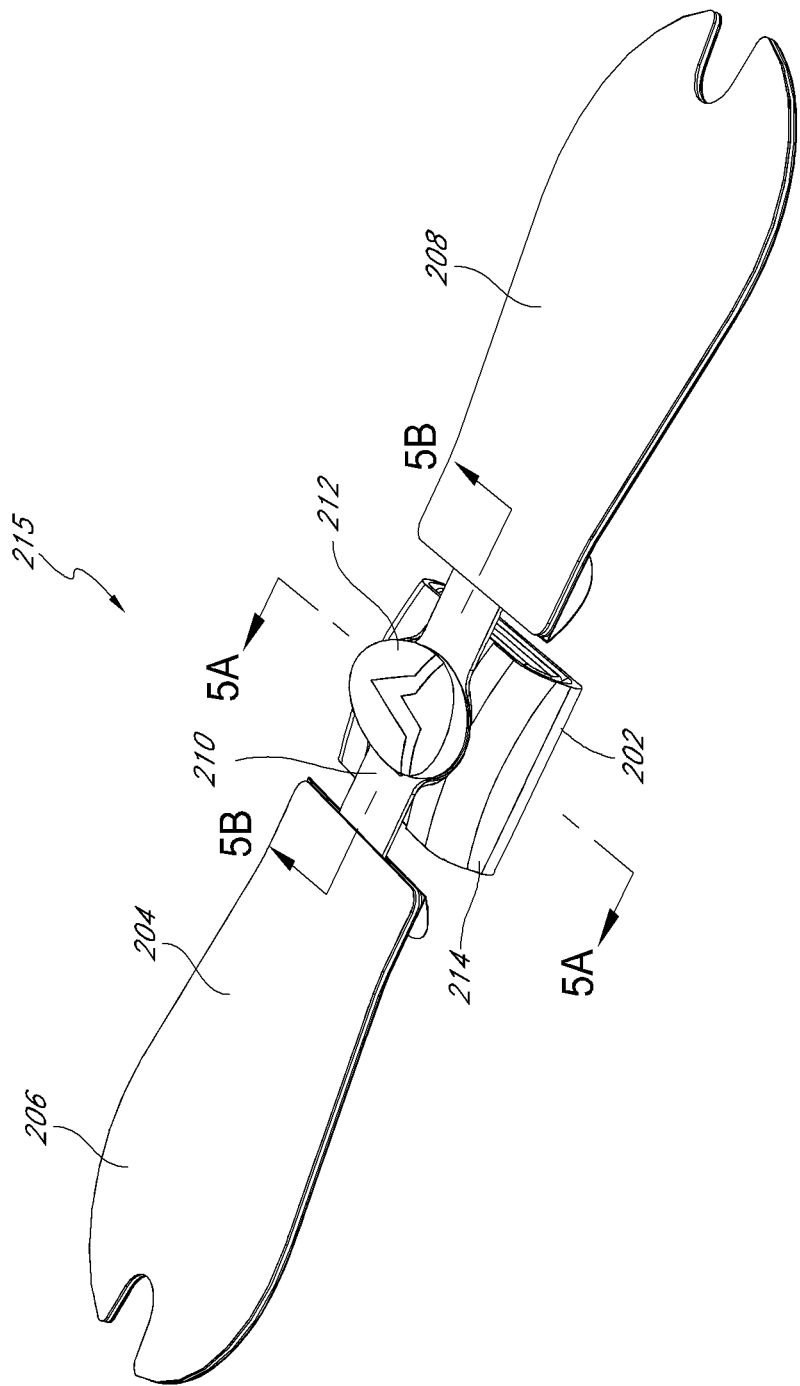
FIGS. 2B-C are top and bottom perspective views, respectively, of a sensor including a sensor subassembly and an attachment subassembly of FIG. 2A.
Figure 2C:
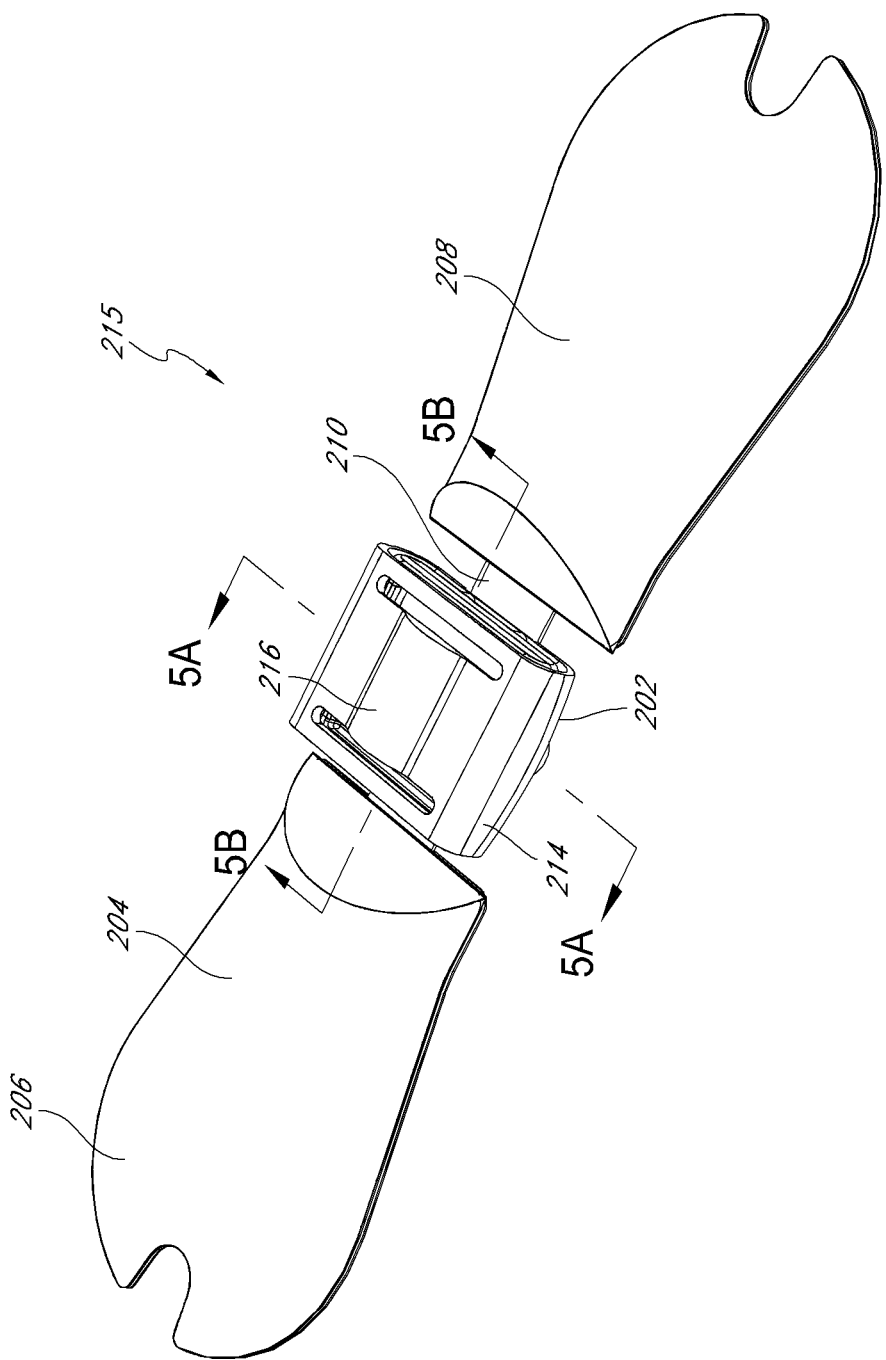

FIGS. 2B-C are top and bottom perspective views of a sensor including subassembly 202 and an attachment subassembly 204 in accordance with an embodiment of the present disclosure. The attachment subassembly 204 generally includes lateral extensions symmetrically placed about the sensor subassembly 202. For example, the attachment subassembly 204 can include single, dual or multiple wing-like extensions or arms that extend from the sensor subassembly 202. In other embodiments, the attachment subassembly 202 has a circular or rounded shape, which advantageously allows uniform adhesion of the attachment subassembly 204 to an acoustic measurement site. The attachment subassembly 204 can include plastic, metal or any resilient material, including a spring or other material biased to retain its shape when bent. In the illustrated embodiment, the attachment subassembly 204 includes a first elongate portion 206, a second elongate portion 208, an elongate member 210 and a button 212. As will be discussed, in certain embodiments the attachment subassembly 204 or portions thereof are disposable and/or removably attachable from the sensor subassembly 202. The button 212 mechanically couples the attachment subassembly 204 to the sensor subassembly 202. The attachment subassembly 204 is described in greater detail below with respect to FIGS. 9A-9D. The attachment subassembly 204 may also be referred to as an attachment element herein.

In one embodiment, the sensor subassembly 202 is configured to be attached to a patient and includes a sensing element configured to detect bodily sounds from a patient measurement site. The sensing element may include a piezoelectric membrane, for example, and is supported by a support structure such as a generally rectangular support frame 218. The piezoelectric membrane is configured to move on the frame in response to acoustic vibrations, thereby generating electrical signals indicative of the bodily sounds of the patient. An electrical shielding barrier (not shown) may be included which conforms to the contours and movements of the piezoelectric element during use. In the illustrated embodiment, additional layers are provided to help adhere the piezoelectric membrane to the electrical shielding barrier 227. Embodiments of the electrical shielding barrier are described below with respect to FIGS. 3A-B and FIGS. 5A-B, for example.

Embodiments of the sensor subassembly 202 also include an acoustic coupler, which advantageously improves the coupling between the source of the signal to be measured by the sensor (e.g., the patient's skin) and the sensing element. The acoustic coupler of one embodiment includes a bump positioned to apply pressure to the sensing element so as to bias the sensing element in tension. The acoustic coupler can also provide electrical isolation between the patient and the electrical components of the sensor, beneficially preventing potentially harmful electrical pathways or ground loops from forming and affecting the patient or the sensor.

The sensor subassembly 202 of the illustrated embodiment includes an acoustic coupler 214 which generally envelops or at least partially covers some or all of the components of the sensor subassembly 202. Referring to FIG. 2C, the bottom of the acoustic coupler 214 includes a contact portion 216 which is brought into contact with the skin of the patient. Embodiments of acoustic couplers are described below with respect to FIGS. 2D-E, 4, and 5A-B, for example.

Figure 2D:
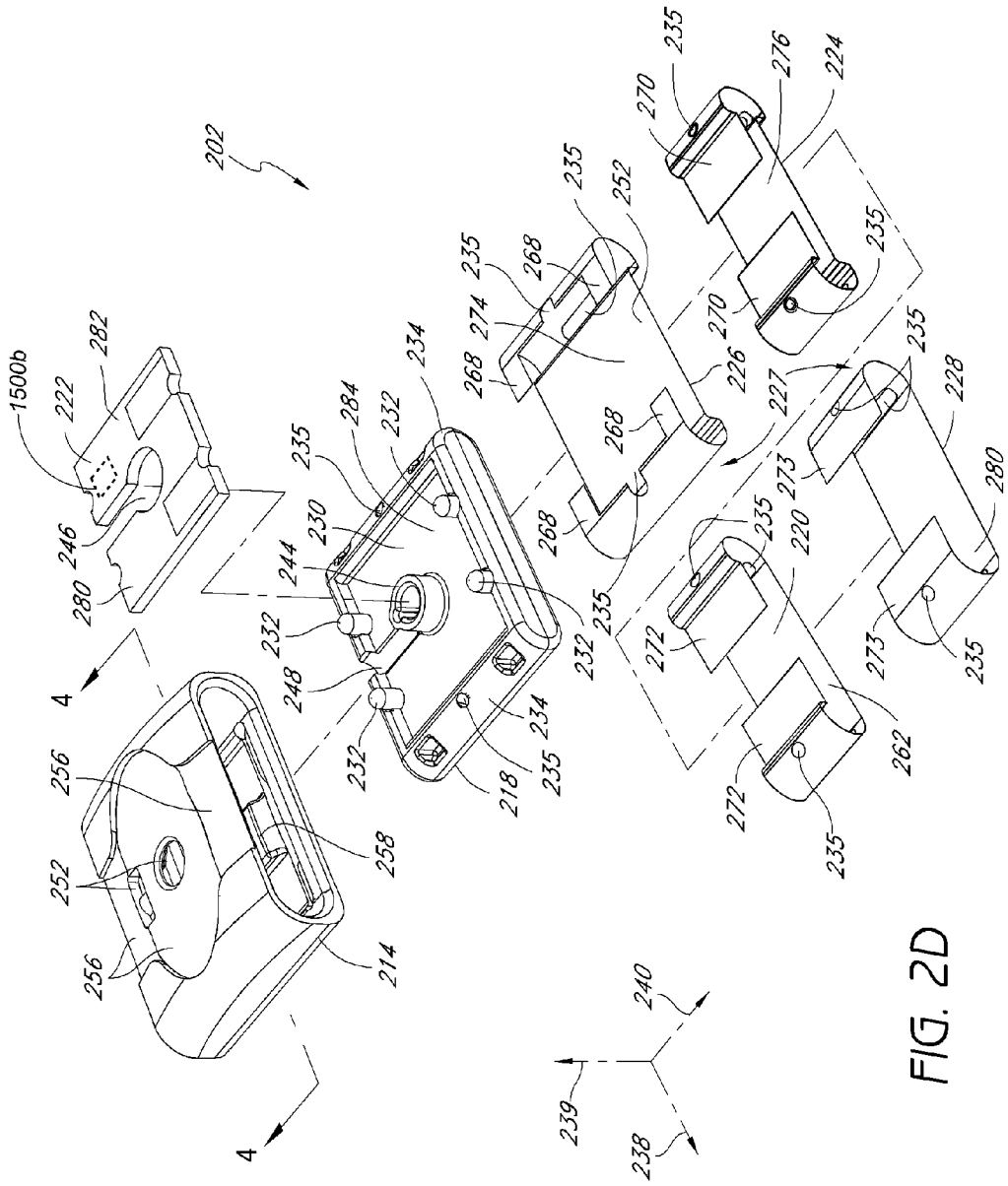
FIGS. 2D-2E are top and bottom exploded, perspective views, respectively, of the sensor subassembly of FIGS. 2A-C.
Figure 2E:
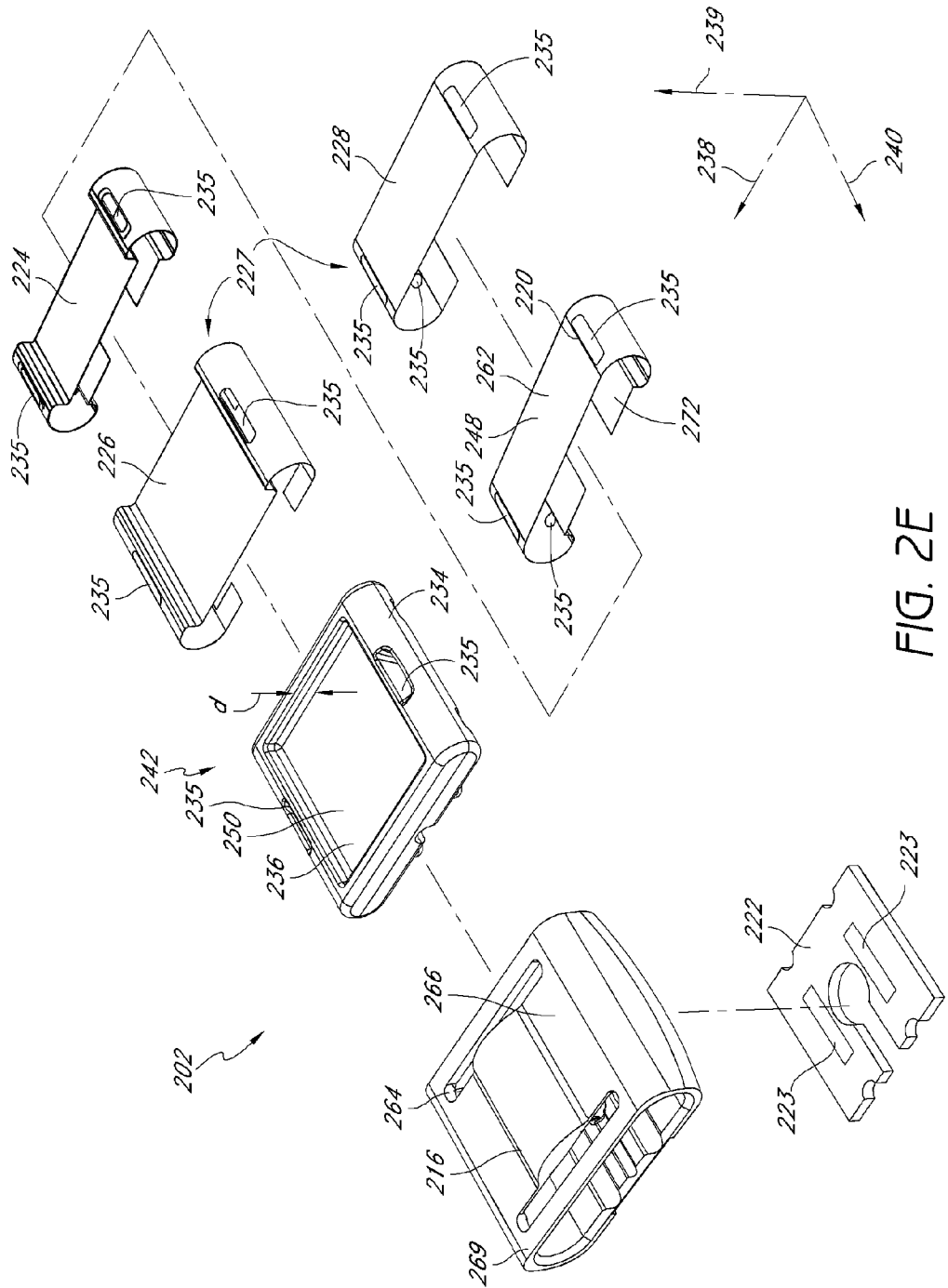

FIGS. 2D-E are top and bottom exploded, perspective views, respectively, of the sensor subassembly 202 of FIGS. 2A-C.

Support Frame

The frame generally supports the various components of the sensor. For example, the piezoelectric element, electrical shielding barrier, attachment element and other components may be attached to the frame. The frame can be configured to hold the various components in place with respect to the frame and with respect to one another, thereby beneficially providing continuous operation of the sensor under a variety of conditions, such as during movement of the sensor. For example, the frame can be configured to hold one or more of the components together with a predetermined force. Moreover, the frame can include one or more features which can improve the operation of the sensor. For example, the frame can include one or more cavities which allow for the piezoelectric element to move freely and/or which amplify acoustic vibrations from bodily sounds of the patient.

In the illustrated embodiment, a PCB 222 is mounted on the frame 218. The frame 218 supports a series of layers which are generally wrapped around the underside 242 of the frame 218 and include, from innermost to outermost, an inner shield layer 226, an bonding layer 224, a sensing element 220 and an outer shield layer 228.

As shown in FIG. 2D, the support frame 218 has a generally rectangular shape, as viewed from the top or bottom, although the frame shape could be any shape, including square, oval, elliptical, elongated, etc. In various embodiments, the frame 218 has a length of from between about 5 and 50 millimeters. In one embodiment, the frame 218 has a length of about 17 millimeters. The relatively small size of the frame 218 can allow the sensor subassembly 202 to be attached comfortably to contoured, generally curved portions of the patient's body. For, example, the sensor subassembly 202 can be comfortably attached to portions of the patient's neck whereas a larger frame 218 may be awkwardly situated on the patient's neck or other contoured portion of the patient. The size of the frame 218 may allow for the sensor subassembly 202 to be attached to the patient in a manner allowing for improved sensor operation. For example, the relatively small frame 218, corresponding to a relatively smaller patient contact area, allows for the sensor subassembly 202 to be applied with substantially uniform pressure across the patient contact area.

The frame 218 is configured to hold the various components in place with respect to the frame. For example, in one embodiment, the frame 218 includes at least one locking post 232, which is used to lock the PCB 222 into the sensor sub-assembly 202, as described below. In the illustrated embodiment, the frame 218 includes four locking posts 232, for example, near each of the 218 four corners of the frame 218. In other embodiments, the frame 218 includes one, two, or three locking posts 218. When the locking posts 232 are brought into contact with horns of an ultrasonic welder or a heat source, they liquefy and flow to expand over the material beneath it and then harden in the expanded state when the welder is removed. When the components of the sensor subassembly 202 are in place, the locking posts 232 are flowed to lock all components into a fixed position.

In one embodiment, the locking posts 232 are formed from the same material as, and are integral with the frame 218. In other embodiments, the locking posts 232 are not formed from the same material as the frame 218. For example, in other embodiments, the locking posts 232 include clips, welds, adhesives, and/or other locks to hold the components of the sensor sub-assembly 202 in place when the locking posts 232 are locked into place.

With further reference to FIG. 2E, in an assembled configuration, the PCB 222 sits inside of an upper cavity 230 of the frame 218 and is pressed against the sensing element 220 to create a stable electrical contact between the PCB 222 and electrical contact portions of the sensing element 220. For example, in certain embodiments, the expanded locking posts 232 press downward on the PCB 222 against the sensing element 220, which is positioned between the PCB 222 and the frame 218. In this manner, a stable and sufficient contact force between the PCB 222 and the sensing element 220 is maintained. For example, as the sensor assembly 200 moves due to acoustic vibrations coming from the patient or due to other movements of the patient, the electrical contact between the PCB 222 and the sensing element 220 remains stable, constant, uninterrupted, and/or unchanged.

In another embodiment, the sensing element 220 may be positioned over the PCB 222 between the expanded locking posts 232 and the PCB 222. In certain embodiments, the contact force between the PCB 222 and the sensing element 220 is from between about 0.5 pounds and about 10 pounds. In other embodiments, the contact force is between about 1 pound and about 3 pounds. In one embodiment, the contact force between the PCB 222 and the sensing element 220 is at least about 2 pounds. The bonding layer 224 is positioned between the frame 218 and the sensing element 220 and allows, among other things, for the sensing element 220 to be held in place with respect to the frame 218 prior to placement of the PCB 222. The PCB 222 and frame 218 include corresponding cutout portions 246, 248 which are configured to accept the sensor cable (not shown).

The PCB cutout portion 246 also includes a circular portion which is configured to accept a button post 244 positioned in the center of the cavity 230. The button post 244 is configured to receive the button 212 (FIG. 2B). The frame 218, shielding layers 226, 228, adhesive layer 224, and sensing element 220 each include injection holes 235 extending through opposing sides of the respective components. Additionally, in an assembled configuration the injection holes 235 of the various components line up with the holes 235 of the other components such that a syringe or other device can be inserted through the holes. Glue is injected into the holes 235 using the syringe, bonding the assembled components together.

Referring now to FIG. 2E, a lower cavity 236 is disposed on the underside of the frame 218 and has a depth d. In an assembled configuration, the sensing element 220 is wrapped around the frame 218 in the direction of the transverse axis 238 such that the lower planar portion 262 of the sensing element 220 stretches across the top of the lower cavity 236. As such, the lower cavity 236 can serve as an acoustic chamber of the multi-parameter sensor assembly. The sensing element 220 thus has freedom to move up into the acoustic chamber in response to acoustic vibrations, allowing for the mechanical deformation of the piezoelectric sensing material and generation of the corresponding electrical signal. In addition, the chamber of certain embodiments allows sound waves incident on the sensing element to reverberate in the chamber. As such, the sound waves from the patient may be amplified or more effectively directed to the sensing element 220, thereby improving the sensitivity of the sensing element 220. As such, the cavity 236 allows for improved operation of the sensor.

Figure 2F:
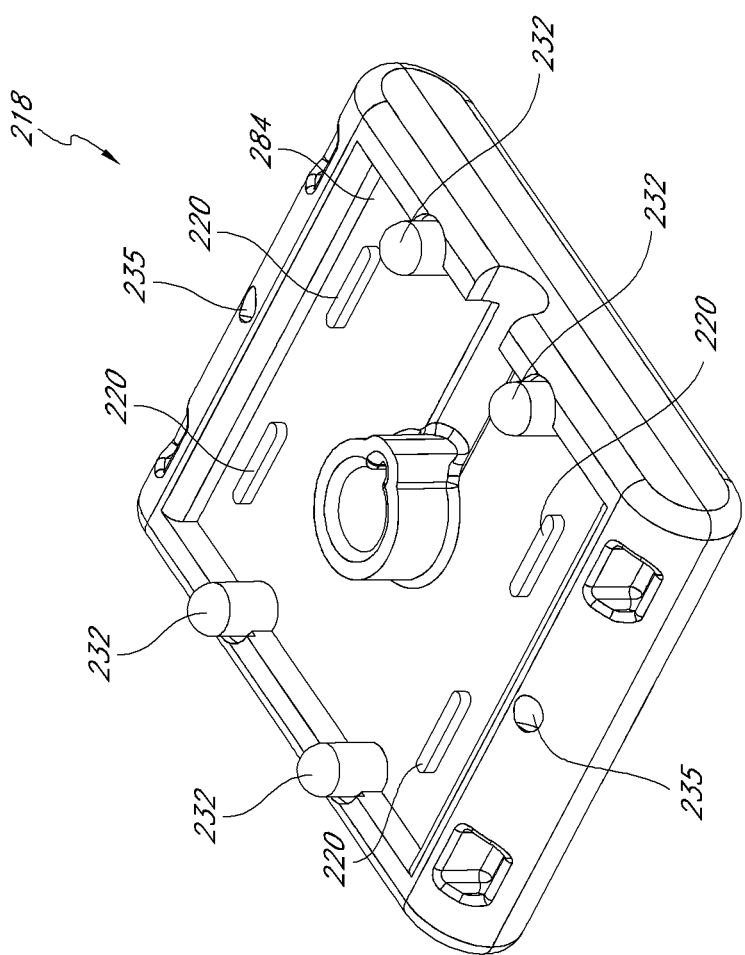
FIG. 2F shows a top perspective view of an embodiment of a support frame.

The frame may include one or more contacts extending from the frame which press into corresponding contact strips of the PCB, helping to ensure a stable, relatively constant contact resistance between the PCB and the sensing element. FIG. 2F shows a top perspective view of another embodiment of a support frame 218, which includes such contacts. The frame 218 may be generally similar in structure and include one or more of the features of the frame 218, such as the locking posts 232 and the upper surface 284. The frame 218 further includes one or more contact bumps 220 which press into corresponding contact strips 223 (FIG. 2B) of the PCB 222 when the sensor sub-assembly is assembled. For example, the contact bumps 220 may include generally narrow rectangular raised segments and may be positioned on the upper surface 284 of the frame 218.

The contact bumps 220 help ensure a stable, constant contact resistance between the PCB 222 and the sensing element 220. The contact bumps 220 are dimensioned to press a portion of the sensing element 220 into the PCB 222 when the sensor subassembly 202 is assembled. In some embodiments, the height of the contact bumps 220 is from about 0.1 to about 1 mm. In some embodiments, the height of the contact bumps 220 is in the range from about 0.2 to about 0.3 mm. In one embodiment, the contact bumps 220 have a height of about 0.26 mm. The height is generally selected to provide adequate force and pressure between the sensing element 220 and PCB 222.

In other embodiments, the contact bumps may have different shapes. For example, the bumps 220 may be generally circular, oval, square or otherwise shaped such that the bumps 220 are configured to press into corresponding contact strips 223 on the PCB 222. The contact strips 223 may be shaped differently as well. For example, the strips 223 may be shaped so as to generally correspond to the cross-sectional shape of the bumps 220. While there are two bumps 220 per contact strip 223 in the illustrated embodiment, other ratios of contact bumps 220 to contract strips 223 are possible. For example, there may be one contact bump 220 per contact strip 223, or more than two contact bumps 220 per contact strip 223.

Referring again to FIGS. 2D-E, the frame 218 includes rounded edges 234 around which the various components including the inner shield 226, the bonding layer 224, the sensing element 220, and the outer shield 228 wrap in the direction of the transverse axis 238. The rounded edges 234 help assure that the sensing element 220 and other layers 226, 224, 228 extend smoothly across the frame 218, and do not include wrinkles, folds, crimps and/or unevenness. Rounded edges 234 advantageously allow uniform application of the sensing element 220 to the frame 218, which helps assure uniform, accurate performance of the sensor assembly 202. In addition, the dimensions of the rounded corners and the upper cavity 230 can help to control the tension provided to the sensing element 220 when it is stretched across the frame 218.

The frame 218 may have different shapes or configurations. For example, in some embodiments, the frame 218 does not include a recess 230 and the PCB 222 sits on top of the frame 218. In one embodiment the edges 234 are not rounded. The frame 218 may be shaped as a board, for example. The frame 218 may include one or more holes. For example, the frame 218 includes four elongate bars connected to form a hollow rectangle in one configuration. In various embodiments, the frame 218 may not be generally rectangular but may instead be generally shaped as a square, circle, oval or triangle, for example. The shape of the frame 218 may be selected so as to advantageously allow the sensor subassembly 202 to be applied effectively to different areas of the body, for example. The shape of the frame 218 may also be selected so as to conform to the shape of one or more of the other components of the sensor system 200 such as the sensing element 220.

In addition, in some embodiments, one or more of the inner shield 226, the bonding layer 224, the sensing layer 220 and the outer shield 228 are not wrapped around the frame 218. For example, in one embodiment, one or more of these components are generally coextensive with and attached to the underside of the frame 218 and do not include portions which wrap around the edges 234 of the frame.

Sensing Element

The sensing element 220 of certain embodiments is configured to sense acoustic vibrations from a measurement site of a medical patient. In one embodiment, the sensing element 220 is a piezoelectric film, such as described in U.S. Pat. No. 6,661,161, incorporated in its entirety by reference herein, and in the '883 Application. Referring still to FIGS. 2D-E, the sensing element 220 includes upper portions 272 and lower planar portion 262. As will be discussed, in an assembled configuration, the top of the upper portions 272 include electrical contacts which contact electrical contacts on the PCB 222, thereby enabling transmission of electrical signals from the sensing element 220 for processing by the sensor system. The sensing element 220 can be formed in a generally "C" shaped configuration such that it can wrap around and conform to the frame 218. Sensing elements in accordance with embodiments described herein can also be found in U.S. patent application Ser. No. 12/044,883, filed Mar. 7, 2008, which is incorporated in its entirety by reference herein. In some embodiments, the sensing element 220 includes one or more of crystals of tourmaline, quartz, topaz, cane sugar, and/or Rochelle salt (sodium potassium tartrate tetrahydrate). In other embodiments, the sensing element 220 includes quartz analogue crystals, such as berlinite ($AlPO_4$) or gallium orthophosphate ($GaPO_4$), or ceramics with perovskite or tungsten-bronze structures ($BaTiO_3$, $SrTiO_3$, $Pb(ZrTi)O_3$, $KNbO_3$, $LiNbO_3$, $LiTaO_3$, $BiFeO_3$, $Na_xWO_3$, $Ba_2NaNb_5O_5$, $Pb_2KNb_5O_{15}$).

In other embodiments, the sensing element 220 is made from a polyvinylidene fluoride plastic film, which develops piezoelectric properties by stretching the plastic while placed under a high pooling voltage. Stretching causes the film to polarize and the molecular structure of the plastic to align. For example, stretching the film under or within an electric field causes polarization of the material's molecules into alignment with the field. A thin layer of conductive metal, such as nickel-copper or silver is deposited on each side of the film as electrode coatings, forming electrical poles. The electrode coating provides an electrical interface between the film and a circuit.

In operation, the piezoelectric material becomes temporarily polarized when subjected to a mechanical stress, such as a vibration from an acoustic source. The direction and magnitude of the polarization depend upon the direction and magnitude of the mechanical stress with respect to the piezoelectric material. The piezoelectric material will produce a voltage and current, or will modify the magnitude of a current flowing through it, in response to a change in the mechanical stress applied to it. In one embodiment, the electrical charge generated by the piezoelectric material is proportional to the change in mechanical stress of the piezoelectric material.

Piezoelectric material generally includes first and second electrode coatings applied to the two opposite faces of the material, creating first and second electrical poles. The voltage and/or current through the piezoelectric material are measured across the first and second electrical poles. Therefore, stresses produced by acoustic waves in the piezoelectric material will produce a corresponding electric signal. Detection of this electric signal is generally performed by electrically coupling the first and second electrical poles to a detector circuit. In one embodiment, a detector circuit is provided with the PCB 222, as described in greater detail below.

By selecting the piezoelectric material's properties and geometries, a sensor having a particular frequency response and sensitivity can be provided. For example, the piezoelectric material's substrate and coatings, which generally act as a dielectric between two poles, can be selected to have a particular stiffness, geometry, thickness, width, length, dielectric strength, and/or conductance. For example, in some cases stiffer materials, such as gold, are used as the electrode. In other cases, less stiff materials, such as silver, are employed. Materials having different stiffness can be selectively used to provide control over sensor sensitivity and/or frequency response.

The piezoelectric material, or film, can be attached to, or wrapped around, a support structure, such as the frame 218. As shown in FIGS. 2D-E, the geometry of the piezoelectric material can be selected to match the geometry of the frame. Overall, the sensor can optimized to pick up, or respond to, a particular desired sound frequency, and not other frequencies. The frequency of interest generally corresponds to a physiological condition or event that the sensor is intended to detect, such as internal bodily sounds, including, cardiac sounds (e.g., heart beats, valves opening and closing, fluid flow, fluid turbulence, etc.), respiratory sounds (e.g., breathing, inhalation, exhalation, wheezing, snoring, apnea events, coughing, choking, water in the lungs, etc.), or other bodily sounds (e.g., swallowing, digestive sounds, gas, muscle contraction, joint movement, bone and/or cartilage movement, muscle twitches, gastro-intestinal sounds, condition of bone and/or cartilage, etc.).

The surface area, geometry (e.g., shape), and thickness of the piezoelectric material 220 generally defines a capacitance. The capacitance is selected to tune the sensor to the particular, desired frequency of interest. Furthermore, the frame 218 is structured to utilize a desired portion and surface area of the piezoelectric material.

The capacitance of the sensor can generally be expressed by the following relationship: $C = \varepsilon S/D$, where C is the sensor's capacitance, $\varepsilon$ is the dielectric constant associated with the material type selected, S is the surface area of the material, and D is the material thickness (e.g., the distance between the material's conducive layers). In one embodiment, the piezoelectric material (having a predetermined capacitance) is coupled to an sensor impedance (or resistance) to effectively create a high-pass filter having a predetermined high-pass cutoff frequency. The high-pass cutoff frequency is generally the frequency at which filtering occurs. For example, in one embodiment, only frequencies above the cutoff frequency (or above approximately the cutoff frequency) are transmitted.

The amount of charge stored in the conductive layers of the piezoelectric material 220 is generally determined by the thickness of its conductive portions. Therefore, controlling material thickness can control stored charge. One way to control material thickness is to use nanotechnology or MEMS techniques to precisely control the deposition of the electrode layers. Charge control also leads to control of signal intensity and sensor sensitivity. In addition, as discussed above, mechanical dampening can also be provided by controlling the material thickness to further control signal intensity and sensor sensitivity.

In addition, controlling the tension of the sensing element 220 in the region where the mechanical stress (e.g., mechanical stress due to acoustic vibration from a patient's skin) is incident upon the sensing element 220 can serve to improve the sensitivity of the sensing element 220 and/or the coupling between the source of the signal (e.g., the patient's skin) and the sensing element 220. This feature will be discussed in greater detail below with respect to the coupler 214.

One embodiment of a piezoelectric sensing element 300 is provided in FIGS. 3A-C. The sensing element 300 includes a substrate 302 and coatings 304, 306 on each of its two planar faces 308, 310. The planar faces 308, 310 are substantially parallel to each other. At least one through hole 312 extends between the two planar faces 308, 310. In one embodiment, the sensing element 300 includes two or three through holes 312.

In one embodiment, a first coating 304 is applied to the first planar face 308, the substrate 302 wall of the through holes 312, and a first conductive portion 314 of the second planar face 310, forming a first electrical pole. By applying a first coating 304 to the through holes 312, a conductive path is created between the first planar face 308 and the first conductive portion 314 of the sensing element 300. A second coating 306 is applied to a second conductive portion 316 of the second planar face 310 to form a second electrical pole. The first conductive portion 314 and second conductive portion 316 are separated by a gap 318 such that the first conductive portion 314 and second conductive portion 316 are not in contact with each other. In one embodiment, the first conductive portion 314 and second conductive portion 316 are electrically isolated from one another.

In some embodiments, the first and second conductive portions 314, 316 are sometimes referred to as masked portions, or coated portions. The conductive portions 314, 316, can be either the portions exposed to, or blocked from, material deposited through a masking, or deposition process. However, in some embodiments, masks aren't used. Either screen printing, or silk screening process techniques can be used to create the first and second conductive portions 314, 316.

In another embodiment, the first coating 304 is applied to the first planar face 308, an edge portion of the substrate 302, and a first conductive portion 314. By applying the first coating 304 to an edge portion of the substrate 302, through holes 312 can optionally be omitted.

In one embodiment, the first coating 304 and second coating 306 are conductive materials. For example, the coatings 304, 306 can include silver, such as from a silver deposition process. By using a conductive material as a coating 304, 306, the multi-parameter sensor assembly can function as an electrode as well.

Electrodes are devices well known to those of skill in the art for sensing or detecting the electrical activity, such as the electrical activity of the heart. Changes in heart tissue polarization result in changing voltages across the heart muscle. The changing voltages create an electric field, which induces a corresponding voltage change in an electrode positioned within the electric field. Electrodes are typically used with echo-cardiogram (EKG or ECG) machines, which provide a graphical image of the electrical activity of the heart based upon signal received from electrodes affixed to a patient's skin.

Therefore, in one embodiment, the voltage difference across the first planar face 308 and second planar face 310 of the sensing element 300 can indicate both a piezoelectric response of the sensing element 300, such as to physical aberration and strain induced onto the sensing element 300 from acoustic energy released from within the body, as well as an electrical response, such as to the electrical activity of the heart. Circuitry within the sensor assembly and/or within a physiological monitor (not shown) coupled to the sensor assembly distinguish and separate the two information streams. One such circuitry system is described in U.S. Provisional No. 60/893,853, filed Mar. 8, 2007, titled, "Multi-parameter Physiological Monitor," which is expressly incorporated by reference herein.

Referring still to FIGS. 3A-C, the sensing element 300 is flexible and can be wrapped at its edges, as shown in FIG. 3C. In one embodiment, the sensing element 300 is the sensing element 220 wrapped around the frame 218, as shown in FIGS. 2D and 2E. In addition, by providing both a first conductive portion 314 and a second conductive portion 316, both the first coating 304 and second coating 306 and therefore the first electrical pole of and the second electrical pole of the sensing element 300 can be placed into direct electrical contact with the same surface of the PCB, such as the PCB 222 as shown FIGS. 5A-B below. This advantageously provides symmetrical biasing of the sensing element 300 under tension while avoiding uneven stress distribution through the sensing element 300.

Bonding Layer

Referring back to FIGS. 2D-E, the bonding layer 224 (sometimes referred to as an insulator layer) of certain embodiments is an elastomer and has adhesive on both of its faces. In other embodiments, the bonding layer 224 is a rubber, plastic, tape, such as a cloth tape, foam tape, or adhesive film, or other compressible material that has adhesive on both its faces. For example, in one embodiment, the bonding layer 224 is a conformable polyethylene film that is double coated with a high tack, high peel acrylic adhesive. The bonding layer 224 in some embodiments is about 2, 4, 6, 8 or 10 millimeters thick.

The bonding layer 224 advantageously forms a physical insulation layer or seal between the components of the sensor subassembly 202 preventing substances entering and/or traveling between certain portions of the sensor subassembly 202. In many embodiments, for example, the bonding layer 224 forms a physical insulation layer that is water resistant or water proof, thereby providing a water-proof or water-resistant seal. The water-resistant properties of the bonding layer 224 provides the advantage of preventing moisture from entering the acoustic chamber or lower cavity 236. In certain embodiments, the sensing element 220, the bonding layer 224 and/or the shield layers 226, 228 (described below) form a water resistant or water proof seal. The seal can prevent moisture, such as perspiration, or other fluids, from entering portions of the sensor subassembly 202, such as the cavity 236 when worn by a patient. This is particularly advantageous when the patient is wearing the multi-parameter sensor assembly 200 during physical activity. The water-resistant seal prevents current flow and/or a conductive path from forming from the first surface of the sensing element 220 to its second surface or vice versa as a result of patient perspiration or some other moisture entering and/or contacting the sensing element 220 and/or sensor assembly 202.

The bonding layer 224 can also provide electrical insulation between the components of the sensor subassembly 202, preventing the flow of current between certain portions of the sensor subassembly 202. For example, the bonding layer 224 also prevents the inside electrical pole from shorting to the outside electrical pole by providing electrical insulation or acting as an electrical insulator between the components. For example, in the illustrated embodiment, the bonding layer 224 provides electrical insulation between the sensing element 220 and the inner shield layer 226, preventing the inside electrical pole of the sensing element 220 from shorting to the outside electrical pole. In another embodiment, a bonding layer is placed between the outer surface of the sensing element 220 and the outer shield layer 228.

The elasticity or compressibility of the bonding layer 224 can act as a spring and provide some variability and control in the pressure and force provided between the sensing element 220 and PCB 222. In some embodiments, the sensor assembly does not include a bonding layer 224.

Electrical Noise Shielding Barrier

An electrical noise shielding barrier can electrically shield the sensing element from external electrical noises. In some embodiments the electrical shielding barrier can include one or more layers which form a Faraday cage around a piezoelectric sensing element, and which distribute external electrical noise substantially equally to the electrical poles of the piezoelectric sensing element. In addition, the shielding barrier flexibly conforms to the surface shape of the piezoelectric element as the surface shape of the piezoelectric element changes, thereby improving the shielding and sensor performance.

Referring still to FIGS. 2D-E, the electrical shielding barrier 227 of the illustrated embodiment includes first and second shield layers 226, 228 (also referred to herein as inner and outer shield layers 226, 228) which form a Faraday cage (also referred to as a Faraday shield) which encloses the sensing element 220 and acts to reduce the effect of noise on the sensing element from sources such as external static electrical fields, electromagnetic fields, and the like. As will be described, one or more of the inner and outer shield layers 226, 228 advantageously conform to the contours of the sensing element 220 during use, allowing for enhanced shielding of the sensing element from external electrical noise.

The inner and outer shield layers 226, 228 include conductive material. For example, the inner and outer shield layers 226, 228 includes copper in certain embodiments and are advantageously formed from a thin copper tape such that the layers can conform to the shape, contours and topology of the sensor element 220 and the frame 218. In various embodiments, one or more of the inner and outer shield layers 226, 228 are from between about 0.5 micrometer and 10 micrometers thick. For example, the shield layers 226, 228, may be from between about 1.5 and about 6 micrometers thick. In one embodiment, the inner and outer shield layers 226, 228 include copper tape about 3 micrometers thick. In yet other embodiments, the shield layers 226, 228 may be greater than 10 micrometers thick or less than 0.5 micrometers thick. In general, the thickness of the shield layer 226, 228 is selected to provide improved electrical shielding while allowing for the shield layers 226, 228 to conform to the sensor element 220 and/or the frame 218. The inner shield layer 226 includes an adhesive on the inside surface 252 such that it can adhere to the frame 218. The inner shield layer 226 adheres directly to the frame 218 and advantageously conforms to the contours of the frame such as the rounded edges 234 and the lower cavity 236, adhering to the surface 250 defining the base of the cavity 236. The bonding layer 224 (e.g., a tape adhesive) is wrapped around and generally conforms to the contours of the inner shield layer 226 and the frame 218. The sensing element 220 is wrapped around the bonding layer 224, the inner shield layer 226 and the frame 218. The outer shield layer 228 is wrapped around and advantageously conforms to the contours of the sensing element 220 and the frame 218. In certain embodiments, a bonding or insulating layer is positioned between the sensing element 220 and the outer shielding layer 228 as well. As such, the sensing element 220 is sandwiched between and enclosed within the inner and outer shield layers 226, 228 which form a Faraday cage around the sensing element 220. The configuration of the shield layers 226, 228, the sensing element 220 and the bonding layer 224 will be described in greater detail below with respect to FIGS. 5A-B.

As discussed, the electrical shielding barrier 227 such as the Faraday cage formed by the inner and outer shield layers 226, 228 helps to reduce the effect of noise electrical noise on the sensing element 220 from sources such as external static electrical fields and electromagnetic fields, thereby lowering the noise floor, providing better noise immunity, or both. For example, the electrical shielding barrier 227 allows for the removal of electrical interference or noise incident directed towards the sensing element 220 while allowing the non-noise component of the sensed signal indicative of bodily sounds to be captured by the sensor 215. For example, in one embodiment the sensing element 220 is a piezoelectric film such as one of the piezoelectric films described herein having positive and negative electrical poles and configured in a differential mode of operation. The electrical shielding barrier 227 acts to balance the effect of the noise by distributing the noise substantially equally to the positive and negative electrical poles of the piezoelectric element. In some embodiments, the electrical shielding barrier 227 distributes the noise equally to both the positive and negative poles. Moreover, the noise signals distributed to the positive and negative electrical poles are substantially in phase or actually in phase with each other. For example, the noise signals distributed to the positive and negative poles are substantially similar frequencies and/or amplitudes with substantially no phase shift between them.

Because the noise signal components on the positive and negative poles are substantially in phase, the difference between the noise components on the respective poles is negligible or substantially negligible. On the other hand, the difference between the differential non-noise sensor signal components indicative of bodily sounds on the positive and negative poles will be non-zero because the sensing element is configured in a differential mode. As such, the noise signals can advantageously be removed or substantially removed through a common-mode rejection technique.

For example, a common-mode rejection element may receive a signal including the combined noise and non-noise sensor signal components of the positive and negative poles, respectively. The common-mode rejection element is configured to output a value indicative of the difference between the combined signal on the positive pole and the combined signal on the negative pole. Because the difference between the noise signals is negligible, the output of the common-mode rejection element will be substantially representative of the non-noise component of the sensor signal and not include a significant noise component. The common mode rejection element may include, for example, an operational amplifier. In one embodiment, for example, three operational amplifiers (not shown) are used and they are disposed on the PCB 222.

Because the shielding layers 226, 228 conform to the topology of the frame 218 and the sensing element 220, the shielding layers 226, 228 are physically closer to the electrical poles of the sensing element 220 and are more uniformly displaced from the sensing element 220. Moreover, the outer shield layer 228 of certain embodiments actively moves with and conforms to the contours of the sensing element 220 during use, such as when the sensor assembly is placed against the skin or when the sensing element 220 is moving due to acoustic vibrations. For example, when placed against the skin, the coupling element 258 pushes against both the outer shielding layer 228 of the shielding barrier 227 and the sensing element 220, causing them to curve along the inside surface of the coupling element 258 (FIG. 5A). Because the cage is flexible and can conform to the movement of the sensing element 220, the shielding performance and sensor performance is improved. This arrangement provides advantages such as for example, for the noise signals to be more accurately and evenly distributed to the positive and negative electrical poles of the sensing element 220 by the shielding layers 226, 228, thereby providing enhanced noise reduction. This arrangement can also provide for improved manufacturability and a more stream-lined design.

Alternative configurations for the electrical shielding barrier 227 are possible. For example, the inner shield layer may not include an adhesive layer and may, for example, be held in place against the frame 218 by pressure (e.g., from the locking posts 232). The outer shield 228 may also include an adhesive layer in some embodiments. In various other embodiments, the shield layers 226, 228 may include other materials such as other types of metals. One or more of the shield layers may be relatively rigid in some configurations. In one embodiment, an insulating layer or bonding layer is disposed between sensing element 220 and the outer shield layer 228. In some embodiments, the inner shield layer 226 actively conforms to the contours of the sensing element 220 during use in addition to the outer shield layer 228. In another embodiment, the inner shield layer 226 actively conforms to the sensing element 220 during use and the outer shield layer 228 does not. In yet other embodiments, the sensor assembly 201 does not include an electrical shielding barrier 227.

Acoustic Coupler

The sensor may also include an acoustic coupler or biasing element, which advantageously improves the coupling between the source of the signal to be measured by the sensor (e.g., the patient's skin) and the sensing element. The acoustic coupler generally includes a coupling portion positioned to apply pressure to the sensing element so as to bias the sensing element in tension. For example, the acoustic coupler may include one or more bumps, posts or raised portions which provide such tension. The bumps, posts or raised portions may be positioned on the inner surface of the coupler, the outer surface of the coupler, or both and may further act to evenly distribute pressure across the sensing element.

In certain embodiments, the acoustic coupler is configured to flex the sensing element, providing improved coupling. For example, the sensing element is attached to the frame and generally stretched in tension across an open cavity of the frame, defining a plane. The acoustic coupler may then be attached to the frame such that it applies pressure to the sensing element, causing the sensing element to flex into the cavity and out of the plane. Such a configuration further biases the sensing element in tension and provides improved sensor operation.

In some embodiments, the acoustic coupler has a first side facing the sensing element and a second side facing the patient's skin when attached to the patient. One or more of the first and second sides can include concave or convex surfaces, for example. In some embodiments, the acoustic coupler includes a concave portion on the second side and, and a convex portion on the first side. In certain embodiments, a portion on the second side of the coupler (e.g., a concaved portion, bump, post, raised portion, etc.) can be sized appropriately so as to contact a patient's skin when the sensor is applied to the patient, providing improved sensor operation.

In addition, the acoustic coupler can be further configured to transmit bodily sound waves to the sensing element. The acoustic coupler can also be configured to provide electrical isolation between the patient and the electrical components of the sensor. In certain embodiments, the sensing element is not electrically coupled to acoustic coupler, for example.

In the illustrated embodiment, the acoustic coupler 214 houses the other components of the sensor subassembly including the frame 218, the PCB 222, the shield layers 226, 228, the bonding layers 224 and the sensing element 220. The acoustic coupler 214 includes a non-conductive material or dielectric. As shown, the acoustic coupler 214 generally forms a dielectric barrier between the patient and the electrical components of the sensor assembly 201. As such, the acoustic coupler 214 provides electrical isolation between the patient and the electrical components of the sensor subassembly 202. This is advantageous in avoiding potential harmful electrical pathways or ground loops forming between the patient and the sensor.

As shown in FIGS. 2D-E, the acoustic coupler 214 is formed in a hollow shell capable of housing the components of the other sensor subassembly 202. Referring to FIG. 2D, the acoustic coupler 214 of the illustrated embodiment also includes recesses 256 and holes 252 capable of receiving and securing the button 212 (FIG. 2B) and portions of the elongate member 210 (FIG. 2B) of the attachment subassembly 204.

FIG. 4 is a cross-sectional view of the acoustic coupler 214 taken along the line 5-5. In certain embodiments, the acoustic coupler includes a bump or protrusion on the inner surface of the coupler 214 and configured to advantageously bias the sensing membrane in tension. For example, a coupling element 258 is disposed on the on the interior bottom portion of the acoustic coupler 214 and which biases the sensing element 220 in tension. The coupling element 258 of the illustrated embodiment is a generally rectangular bump which extends by a height h above the cavity 260 which is formed on the interior bottom of the acoustic coupler 214. The coupling element 258 is centered about and extends along the longitudinal axis 240 (FIGS. 2D and 2E) from near the front of the acoustic coupler 214 to near the back of the acoustic coupler 214. In the illustrated embodiment, the coupling element 258 is about ¼ of the width of the acoustic coupler 214 along the transverse axis 238. As will be discussed in greater detail below with respect to FIG. 5A-B, the coupling element 258 can advantageously bias the sensing element 220 in tension by applying pressure to the sensing element 220. Because the sensing element 220 may be generally taut in tension under the pressure of the coupling bump 258, the sensing element 220 will be mechanically coupled to the coupling bump 258 and responsive to acoustic vibrations travelling through the coupler 214 to the sensing element 220, thereby providing improved coupling between the patient's skin and the sensing element 220. As such, the acoustic coupler 214 provides for improved measurement sensitivity, accuracy, or both, among other advantages.

The acoustic coupler 214 is further configured to transmit bodily sound waves to the sensing element 220. The coupler 214 can further include a portion disposed on the outer surface of the coupler 214 and which is configured to contact the skin during use. For example, the acoustic coupler 214 can include an outer protrusion, bump or raised portion on the outer surface. Referring to FIGS. 2E and 4, the underside of the acoustic coupler 214 includes portion 216 which is configured to contact the skin of the patient and can provides contact between the skin and the acoustic coupler 214. Acoustic vibrations from the skin will be incident on the portion 216, travel through the acoustic coupler to the coupling bump 258 and eventually be incident on the sensing element 220 held in tension by the bump 258. In addition, the contact portion 216 may, in conjunction with the coupling element 258 or on its own, also help to improve the coupling between the skin and the sensing element 220. For example, when pressed against the skin, the contact portion 216 may push a portion of the inner surface of the coupler 214, such as the coupling element 258, into the sensing element 220, advantageously holding the sensing element 220 in tension. As shown, the contact portion 216 of the illustrated embodiment includes a semi-cylindrical bump mounted generally underneath the coupling element 258. Similar to the coupling element 258, the contact portion 216 is centered about and extends along the longitudinal axis 240 from near the front of the acoustic coupler 214 to near the back of the acoustic coupler 214. Moreover, the acoustic coupler 214 acts to evenly distribute pressure to the sensing element 220 during use. For example, because the coupling element 258 and the portion 216 are generally positioned such that they are centered with respect to surface of the sensing element 220, pressure will be distributed symmetrically and/or evenly across the sensing element 220.

Referring to FIG. 2E, a pair of slots 264 are disposed on either end of the contact portion 216 and each run generally along the transverse axis from near the left side of the acoustic coupler 214 to the right side of the acoustic coupler 214. The slots serve to decouple a segment 266 of the bottom of the acoustic coupler 214 including the coupling element 258 and the contact portion 216 from the remainder of the acoustic coupler 214. As such, the segment 266 can move at least partially independent from the rest of the acoustic coupler 214 in response to acoustic vibrations on the skin of the patient, thereby efficiently transmitting acoustic vibrations to the sensing element 220. The acoustic coupler 214 of certain embodiments includes an elastomer such as, for example, rubber or plastic material.

In an alternative embodiment of the acoustic coupler 214, for example, the acoustic coupler 214 does not include a hollow shell and does not house the other components of the sensor subassembly. For example, the coupler 214 may include a single planar portion such as, for example, a board which couples to the underside of the frame 218 such that the shielding layers 226, 228, the sensing element 220 and the bonding layer 224 are positioned between the coupler 214 and the frame 218. In some configurations, the coupler 214 is positioned between the frame 218 and one or more of the shielding layers 226, 228, the sensing element 220 and the bonding layer 224. Moreover, the acoustic coupler 214 may include a dielectric material, which advantageously electrically isolates the electrical components of the sensor subassembly 202 from the patient. For example, the dielectric layer may ensure that there is no electrical connection or continuity between the sensor assembly and the patient.

In certain embodiments, portions of the sensor assembly such as, for example, the acoustic coupler 214 may include a gel or gel-like material. The gel may provide beneficial acoustic transmission, for example, serving to enhance the coupling between the acoustic vibrations from the patient's skin and the sensing element 220. The gel may provide acoustic impedance matching, for example, between the skin and the sensor. For example, the gel may serve to reduce the impedance mismatch from potential skin-to-air and air-to-sensing element discontinuity, thereby reducing potential reflections and signal loss. The gel may be embedded in a portion of the acoustic coupler 214. For example, one or more of the coupling element 258 and the contact portion 216 may include a gel or gel-like material. The acoustic coupler 214 may include an embedded gel in certain embodiments where one or more of the coupling element 258 and the contact portion 216 are not included. For example, the entire patient contact portion of the acoustic coupler 214 may include gel material extending substantially from the patient contact surface to the interior of the coupler 214 across the contact portion. One or more columns of gel material may extend from the patient contact surface of the coupler 214 to the interior of the coupler 214 in other embodiments. In yet further embodiments, the gel is not embedded in the acoustic coupler 214 but is added to the skin directly. In one embodiment, the gel is embedded in the acoustic coupler 214 and is configured to be released from the coupler 214 when the sensor assembly is applied to the patient. For example, gel can be filled in one or more cavities of the acoustic coupler 214 prior to use wherein the cavities are configured to open and release the gel when the coupler is pressed against the skin.

FIGS. 5A-B are cross-sectional views of the sensor subassembly 202 of FIG. 2 along the lines 5A-5A and 5B-5B, respectively. As shown, the inner copper shield 226 is positioned as the inner most of the shield layers 226, 228, the bonding layer 224 and the sensing element 220. Referring to FIGS. 2D-E and FIGS. 5A-B, the four tabs 268 of the inner copper shield 226 are flat and extend across the top of the frame recess 230 and the four corners of the top surface of the PCB (not shown in FIGS. 5A-B) which sits in the frame recess 230. The bonding layer 224 is wrapped around the inner copper shield 226. The upper portions 270 of the bonding layer 224 bend downward to conform to the shape of the frame 218 such that they extend across and contact the bottom of the frame cavity 230. The sensing element 220 is wrapped around the bonding layer 224 and the upper portions 272 of the sensing element 220 also bend downward to conform to the shape of the frame 218. As such, the upper portions 272 of the sensing element 220 extend across the bottom of the frame cavity 230 and are in contact with the bottom of the PCB 222 and the top surface of the bonding layer 224. The outer copper layer 228 is wrapped around the sensing element 220 and the upper planar portions 273 of the outer copper shield 228 are flat, extend across the top of the frame recess 230, and are in contact with the top surface of the PCB (not shown).

The shield layers 226, 228, the bonding layer 224 and the sensing element 220 wrap around the rounded edges 234 of the frame 218. The lower planar portions 274, 276 of the inner shield layer 226 and the bonding layer 224 bend upwards so as extend across the bottom surface 250 of the frame 218. The lower planar portions 262, 280 of the sensing element 220 and the outer shield layer 228, on the other hand, extend between the lower frame cavity 236 and the coupler cavity 260. Moreover, the lower planar portions 262, 280 of the sensing element 220 and the outer shield layer 228 extend across the top of the coupling portion 258. Because the coupler portion 258 extends slightly above the coupler cavity 260 into the lower frame cavity 236 by the distance h, the sensing element 220 is advantageously biased in tension improving the sensitivity of the sensing element 220, the coupling of the sensing element 220 to acoustic vibrations in the skin of the patient (not shown), or both.

In various embodiments, the components of the sensor subassembly 202 may be arranged differently. For example, the components may be combined such that the overall assembly include fewer discrete components, simplifying manufacturability. In one embodiment, one or more of the shielding layers 226, 228, the bonding layer 224 and the sensing element 220 may include an integral portion (e.g., a multi-layered film). In some embodiments, more than one bonding layer 224 is used. In one embodiment, adhesive layers are formed on one or more of the shielding layers 226, 228 and the sensing element 220, and no separate bonding layer 224 is present. In another embodiment, the various layers are held together by pressure (e.g., from the contact posts 232 and/or PCB) instead of through the use of adhesives.

Referring still to FIGS. 2D-E and 5A-B, a method for attaching the shielding layers 226, 228, the bonding layer 224, the sensing element 220 and the PCB 222 to the frame 218 includes providing the inner shield 226 and attaching it to the frame 218. The sensing element 220 and bonding layer 224 are provided and also attached to the frame 218. A printed circuit board 222 is then provided. The printed circuit board 222 is placed on top of the sensing element 220 such that a first edge 280 of the printed circuit board 222 is placed over a first conductive portion of the sensing element 220, and a second edge 282 of the printed circuit board 222 is placed over a second conductive portion of the sensing element 220.

The printed circuit board 222 is pressed down into the sensing element 220 in the direction of the frame 218. As the printed circuit board 222 is pressed downward, the contact bumps (not shown) of the frame 218 push the bonding layer 224 and sensing element 220 into contact strips located along the first and second sides or edges 280, 282 of the printed circuit board 222. The contact strips of the printed circuit board 222 are made from conductive material, such as gold. Other materials having a good electro negativity matching characteristic to the conductive portions of the sensing element 220, may be used instead. The elasticity or compressibility of the bonding layer 224 acts as a spring, and provides some variability and control in the pressure and force provided between the sensing element 220 and printed circuit board 222.

Once the outer shield 228 is provided and attached to the frame 218, a desired amount of force is applied between the PCB 222 and the frame 218 and the locking posts 232 are vibrated or ultrasonically or heated until the material of the locking posts 232 flows over the PCB 222. The locking posts 232 can be welded using any of a variety of techniques, including heat staking, or placing ultrasonic welding horns in contact with a surface of the locking posts 232, and applying ultrasonic energy. Once welded, the material of the locking posts 232 flows to a mushroom-like shape, hardens, and provides a mechanical restraint against movement of the PCB 222 away from the frame 218 and sensing element 220. By mechanically securing the PCB 222 with respect to the sensing element 220, the various components of the sensor subassembly 202 are locked in place and do not move with respect to each other when the multi-parameter sensor assembly is placed into clinical use. This prevents the undesirable effect of inducing electrical noise from moving assembly components or inducing instable electrical contact resistance between the PCB 222 and the sensing element 220. In certain embodiments, the locking posts 232 provide these advantages substantially uniformly across multiple sensors.

Therefore, the PCB 222 can be electrically coupled to the sensing element 220 without using additional mechanical devices, such as rivets or crimps, conductive adhesives, such as conductive tapes or glues, like cyanoacrylate, or others. In addition, the mechanical weld of the locking posts 232 helps assure a stable contact resistance between the PCB 222 and the sensing element 220 by holding the PCB 222 against the sensing element 220 with a constant pressure, for example, and/or preventing movement between the PCB 222 and the sensing element 220 with respect to each other.

The contact resistance between the sensing element 220 and PCB 222 can be measured and tested by accessing test pads on the PCB 222. For example, in one embodiment, the PCB 222 includes three discontinuous, aligned test pads that overlap two contact portions between the PCB 222 and sensing element 220. A drive current is applied, and the voltage drop across the test pads is measured. For example, in one embodiment, a drive current of about 100 mA is provided. By measuring the voltage drop across the test pads the contact resistance can be determined by using Ohm's law, namely, voltage drop (V) is equal to the current (I) through a resistor multiplied by the magnitude of the resistance (R), or V=IR. While one method for attaching the shield layers 226, 228, the bonding layer 224, the sensing element and the PCB 222 to the frame 218 has been described, other methods are possible. For example, as discussed, in some embodiments, one or more of the various separate layers are combined in an integral layer which is attached to the frame 218 in one step.

Printed Circuit Board

The PCB 222 includes various electronic components mounted to either or both faces of the PCB 222. When sensor assembly is assembled and the PCB 222 is disposed in the upper frame cavity 230, some of the electronic components of the PCB 222 may extend above the upper frame cavity 230. To reduce space requirements and to prevent the electronic components from adversely affecting operation of the sensor assembly, the electronic components can be low-profile, surface mounted devices. The electronic components are often connected to the PCB 222 using conventional soldering techniques, for example the flip-chip soldering technique. Flip-chip soldering uses small solder bumps such of predictable depth to control the profile of the soldered electronic components. The four tabs 268 of the inner copper shield 226 and the upper planar portions 273 of the outer copper shield 228 are soldered to the PCB 222 in one embodiment, electrically coupling the electrical shielding barrier to the PCB 222.

In some embodiments, the electronic components include filters, amplifiers, etc. for pre-processing or processing a low amplitude electric signal received from the sensing element 220 (e.g., the operational amplifiers discussed above with respect to the Faraday cage) prior to transmission through a cable to a physiological monitor. In other embodiments, the electronic components include a processor or pre-processor to process electric signals. Such electronic components may include, for example, analog-to-digital converters for converting the electric signal to a digital signal and a central processing unit for analyzing the resulting digital signal.

In other embodiments, the PCB 222 includes a frequency modulation circuit having an inductor, capacitor and oscillator, such as that disclosed in U.S. Pat. No. 6,661,161, which is incorporated by reference herein. In another embodiment, the PCB 222 includes an FET transistor and a DC-DC converter or isolation transformer and phototransistor. Diodes and capacitors may also be provided. In yet another embodiment, the PCB 3114 includes a pulse width modulation circuit.

In one embodiment, the PCB 222 also includes a wireless transmitter, thereby eliminating mechanical connectors and cables. For example, optical transmission via at least one optic fiber or radio frequency (RF) transmission is implemented in other embodiments. In other embodiments, the sensor assembly includes an information element which can determine compatibility between the sensor assembly and the physiological monitor to which it is attached and provide other functions, as described below.

Information Element

Figure 6A:
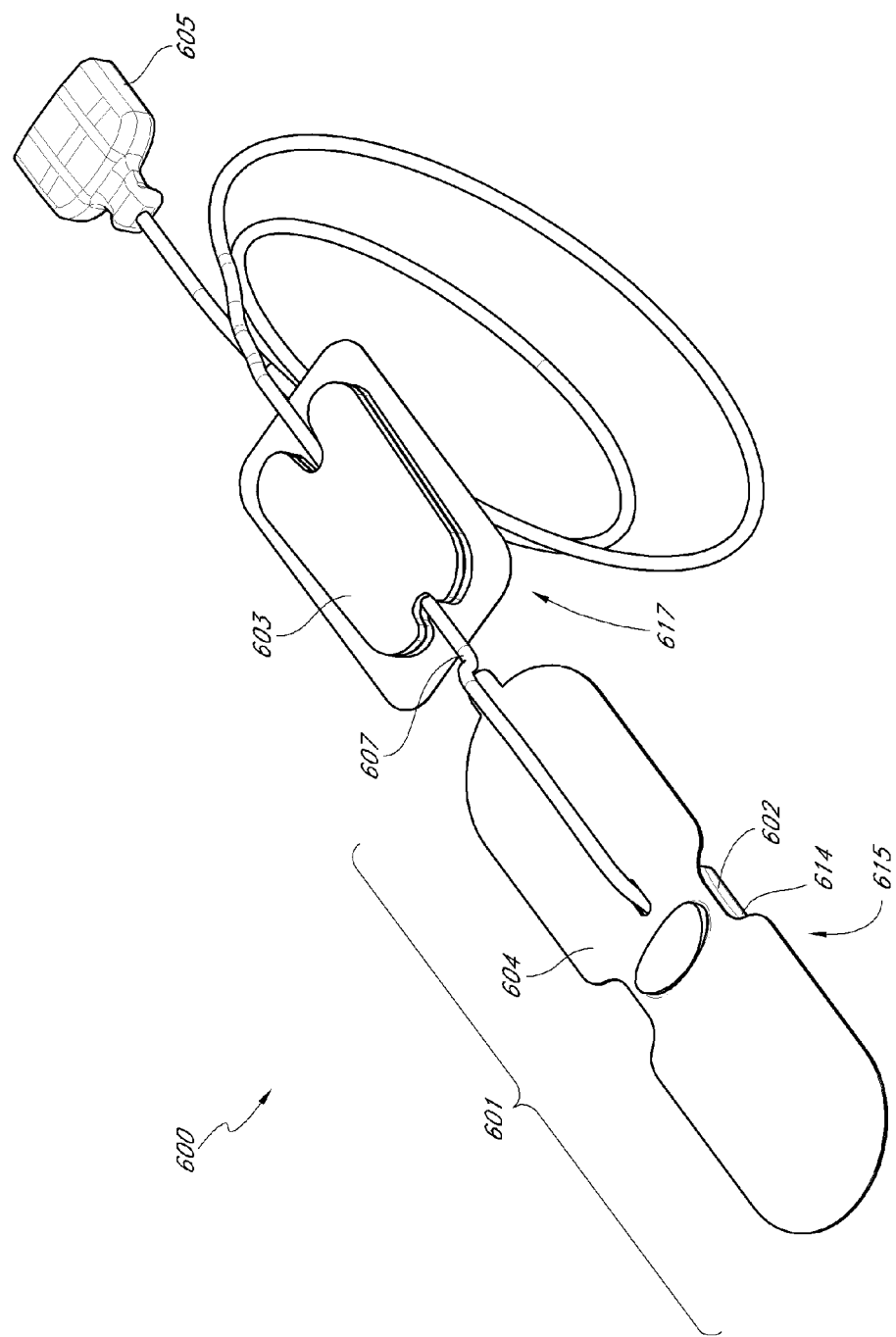
FIG. 6A is a top perspective view illustrating portions of a sensor assembly in accordance with another embodiment of the disclosure.

FIG. 6A is a top perspective view illustrating portions of another embodiment of a sensor system 600 including a sensor assembly 601 suitable for use with any of the physiological monitors shown in FIGS. 1A-C. The sensor assembly 601 includes a sensor 615, a cable assembly 617 and a connector 605. The sensor 615, in one embodiment, includes a sensor subassembly 602 and an attachment subassembly 604. The cable assembly 617 of one embodiment includes a cable 607 and a patient anchor 603. The various components are connected to one another via the sensor cable 607. The sensor connector 605 can be removably attached to a physiological monitor (not shown), such as through a monitor cable, or some other mechanism. In one embodiment, the sensor assembly 601 communicates with a physiological monitor via a wireless connection.

The sensor system 600 and certain components thereof may be generally similar in structure and function or identical to other sensor systems described herein, such as, for example, the sensor systems 100, 200 described herein with respect to FIGS. 1-5.

For example, the sensor system 600 may include an electrical shielding barrier (FIGS. 6D-E) including one or more layers which form a Faraday cage around an piezoelectric sensing element (FIG. 6D-E), and which distribute external electrical noise substantially equally to electrical poles of the piezoelectric sensing element. The shielding barrier or portions thereof of some embodiments can flexibly conform to the surface shape of the piezoelectric element as the surface shape of the piezoelectric element changes, thereby improving the shielding and sensor performance.

The sensor system 600 may further include an acoustic coupler 614 which can including a bump positioned to apply pressure to the sensing element so as to bias the sensing element in tension. The acoustic coupler can also provide electrical isolation between the patient and the electrical components of the sensor, beneficially preventing potentially harmful electrical pathways or ground loops from forming and affecting the patient or the sensor.

The sensor system 609 may also include an attachment subassembly 604. In one embodiment, the attachment subassembly 604 is configured to press the sensor against the patient's skin with a pre-determined amount of force. The attachment subassembly 604 can be configured act in a spring-like manner to press the sensor 600 against the patient. The attachment subassembly 604 can also be configured such that movement of the sensor 600 with respect to the attachment subassembly 604 does not cause the attachment subassembly 604 to peel off or otherwise detach from the patient during use.

Additionally, in some embodiments, a patient anchor 603 is provided which advantageously secures the sensor 615 to the patient at a point between the ends of the cable 607. Securing the cable 607 to the patient can decouple the sensor assembly 600 from cable 607 movement due to various movements such as accidental yanking or jerking on the cable 607, movement of the patient, etc. Decoupling the sensor assembly 600 from cable 607 movement can significantly improve performance by eliminating or reducing acoustical noise associated with cable 607 movement. For example, by decoupling the sensor 600 from cable movement, cable movement will not register or otherwise be introduced as noise in the acoustical signal generated by the sensor 600.

The shielding barrier, acoustic coupler 614, attachment subassembly 604, and patient anchor 603 may be generally similar in certain structural and functional aspects to the shielding barrier, acoustic coupler 214, attachment subassembly 204, and patient anchor 203 of other sensor systems described herein, such as the sensor system 200 described with respect to FIGS. 2A-5B, for example.

Figure 6B:
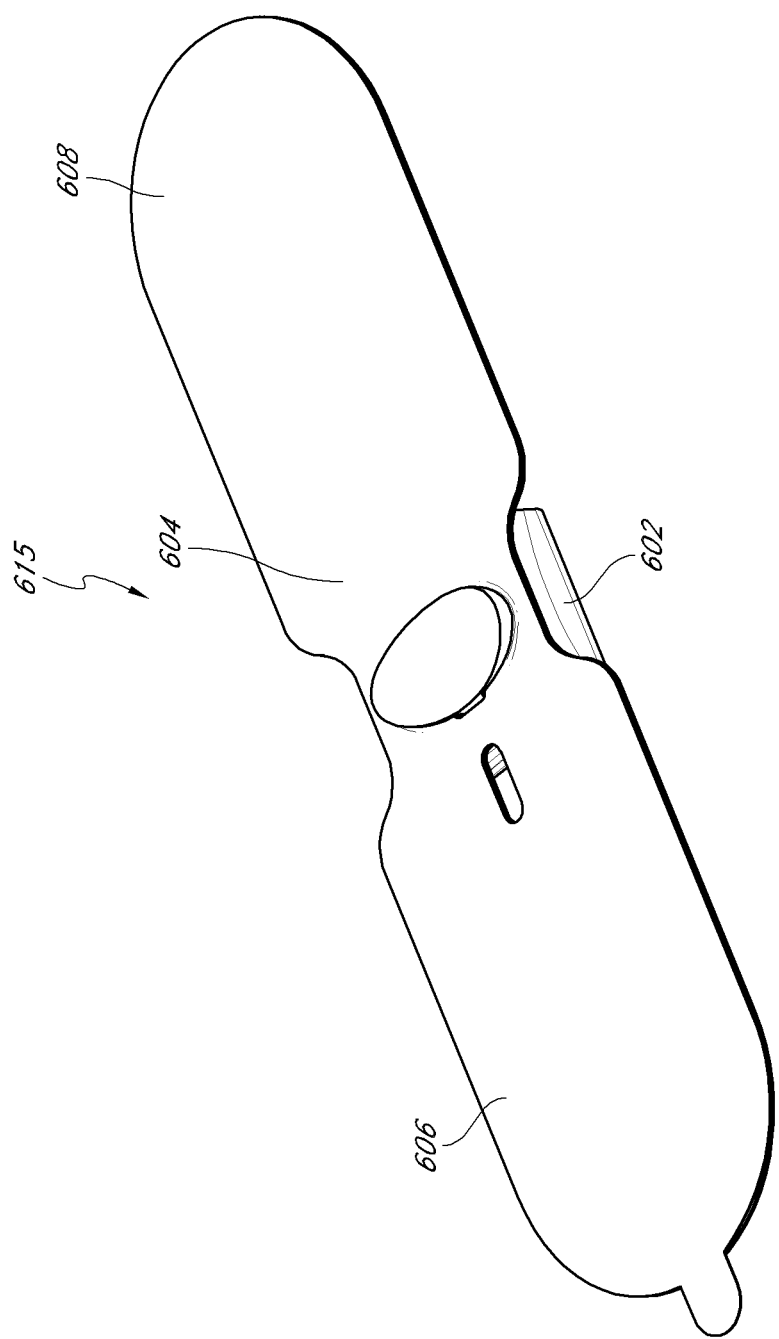
FIG. 6B-C are top and bottom perspective views, respectively, of a sensor including a sensor subassembly and an attachment subassembly of FIG. 6A.
Figure 6C:
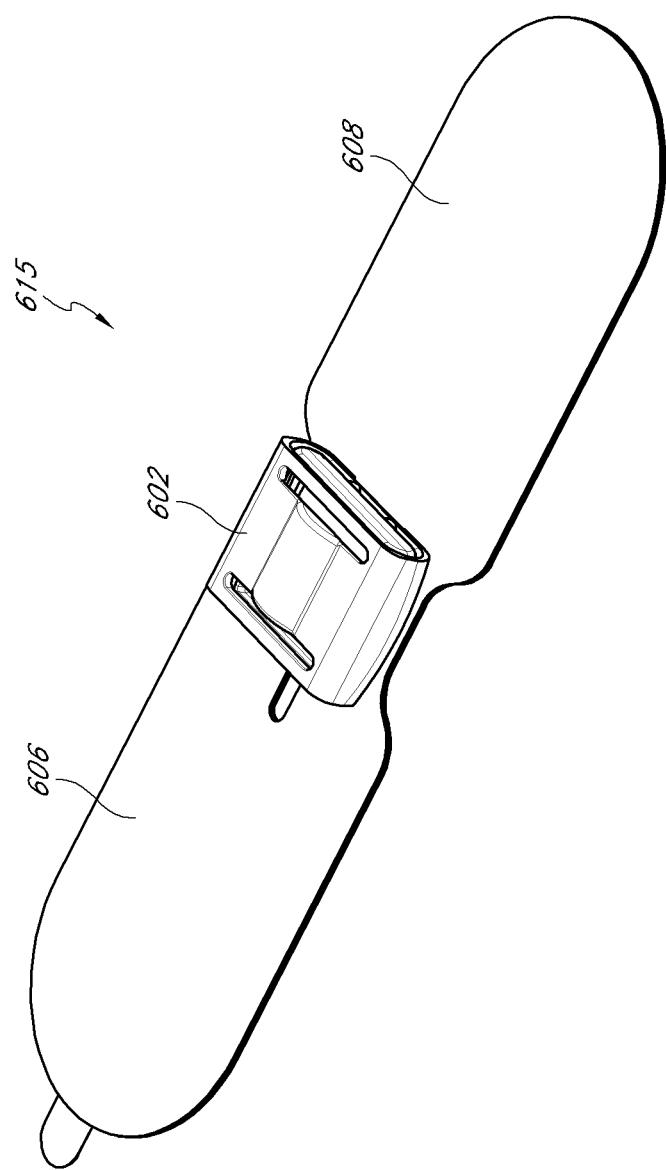

FIGS. 6B-C are top and bottom perspective views of a sensor including subassembly 602 and an attachment subassembly 604 in accordance with another embodiment of the present disclosure. The attachment subassembly 604 generally includes lateral extensions symmetrically placed about the sensor subassembly 602. An embodiment of a similar attachment subassembly is described in detail with respect to FIG. 10.

Figure 6D:
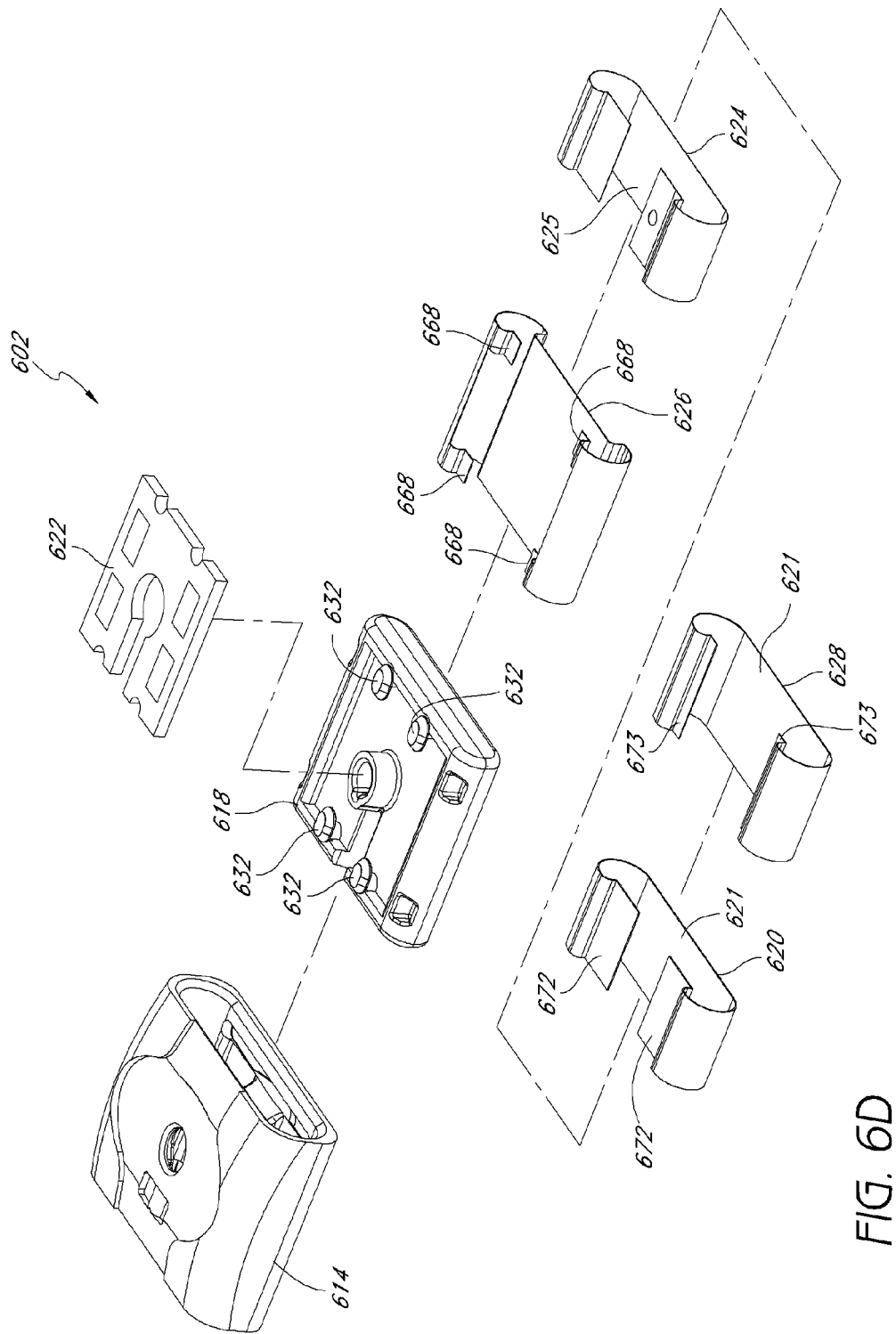
FIG. 6D-E are top and bottom exploded, perspective views, respectively, of the sensor subassembly of FIGS. 6A-C.
Figure 6E:
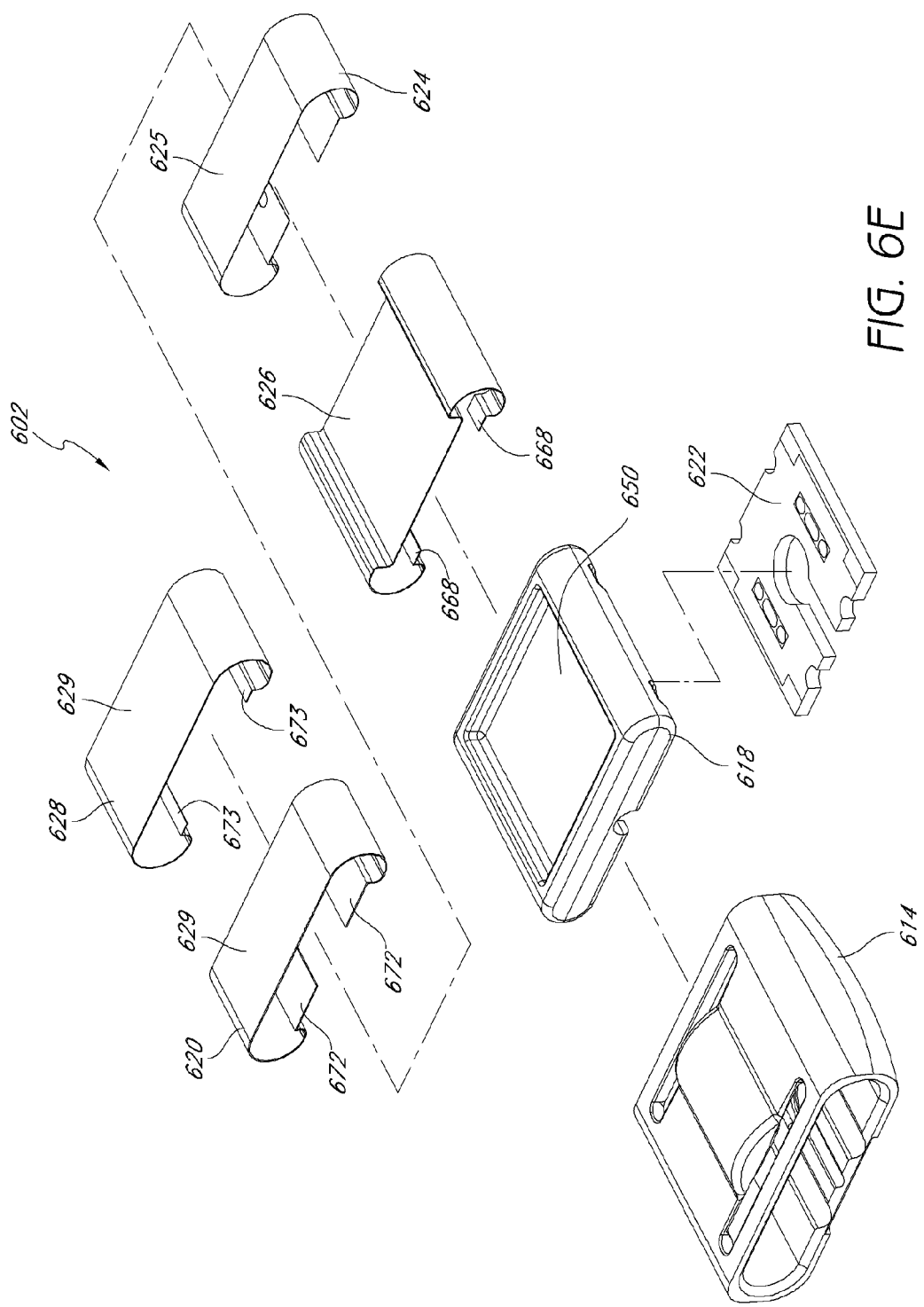

FIG. 6D-E are top and bottom exploded, perspective views, respectively, of the sensor subassembly of FIGS. 6A-C. The frame 618 generally supports the various components of the sensor such as the piezoelectric element, electrical shielding barrier, attachment element and other components. The sensor subassembly 602 includes an acoustic coupler 614, sensing element 620, adhesive layer 624, and first and second electrical shielding layers 626, 628 which may, in certain aspects, be generally similar in structure and function to the acoustic coupler 214, sensing element 220, adhesive layer 224, and first and second electrical shielding layers 226, 228 of FIGS. 2A-2E, for example.

As shown, and unlike the embodiment shown in FIGS. 2A-E, the adhesive layer 624 of FIG. 6D-E stretches straight across the frame 628 without conforming to the surface 650 on the underside of the frame 618. Thus, the sensing element 620 is sandwiched between the adhesive layer 624 and the outer shielding layer 628. The adhesive layer 624 includes adhesive over its entire outer surface which is in contact with the sensing element 220. Moreover, the copper layer 628 may also include an adhesive on its interior surface which contacts the other side of the sensing element 220. As such, the adhesive layer 624 and the shielding layer 628 bond to opposite sides of the sensing element 220, sandwiching and creating a seal around it. This sandwiching and sealing of the sensing element 620 improves the liquid resistivity of the sensor subassembly 602 by impeding water or water vapors (e.g., from sweat or other sources) from ingressing and contacting the sensing element 220. Thus, the sandwiching of the sensing element 620 protects the sensor 602 from undesired effects such as electrical shorting due to liquid ingress. In one embodiment, the sensor 602 is IPX1 compliant.

The planar portion 625 of the adhesive layer 624, along with the corresponding planar portions 621, 629 of the sensing element 620 and outer shielding layer 628, are configured to move with respect to the cavity defined by the underside of the frame 618 in response to vibrations. The adhesive layer 624 generally includes adhesive on all of its surface area except for the interior surface of the planar portion 625. As such, the adhesive layer 624 is securely bonded in place while the planar portion 625 can move freely with respect to the cavity during operation without sticking. Moreover, because the interior portion of the planar portion 625 is non-adhesive, foreign material such as dust particles will generally not stick to the non-adhesive planar portion 625, improving sensor operation.

Similar to the frame 218 of FIG. 2D, the frame 618 includes four locking posts 632. However, the posts 632 of FIG. 6D are shown in a locked or liquefied configuration, unlike the posts 232 illustrated in FIG. 2D.

As shown in FIG. 6D, the shielding layers 626, 628 include flap portions 668, 673 which conform to the frame 618 and sit underneath the PCB 622 in an assembled configuration. Similarly, the sensing element 620 of the sensor subassembly 602 includes a flap portion 672 which conforms to the frame 618 and sits underneath the PCB 622. Upon welding of the locking posts 632, the PCB 622 is pressed downwards into physical and electrical contact with the flap portions 668, 673, 672 of the shielding layers 626, 628 and sensing element 620. As such, because the flaps 668, 673, 672 are configured to sit underneath the PCB 622, they are held in place in a pressure fit without soldering, improving manufacturability.

In addition, the sensor assembly can include any of a variety of information elements 1500b, such as readable and/or writable memories. Information elements can be used to keep track of device usage, manufacturing information, duration of sensor usage, compatibility information, calibration information, identification information, other sensor, physiological monitor, and/or patient statistics, etc. The information element can communicate such information to a physiological monitor. For example, in one embodiment, the information element identifies the manufacturer, lot number, expiration date, and/or other manufacturing information. In another embodiment, the information element includes calibration information regarding the multi-parameter sensor assembly 602. Information from the information element is provided to the physiological monitor according to any communication protocol known to those of skill in the art. For example, in one embodiment, information is communicated according to an I$^2$C protocol. The information element may be provided on or be in electrical communication with the PCB 622 (see, e.g., 1500b in FIG. 2D). In various embodiments, the information element can be located in another portion of the sensor assembly. For example, in one embodiment, the information element is provided on a cable connected to the PCB 622. The information element may further be located on the sensor connector 605 (see, e.g., 1500a in FIG. 1B), the attachment subassembly 604, or some other part of the sensor assembly.

The information element can include one or more of a wide variety of memory devices known to an artisan from the disclosure herein, including an EPROM, an EEPROM, a flash memory, a combination of the same or the like. The information element can include a read-only device such as a ROM, a read and write device such as a RAM, combinations of the same, or the like. The remainder of the present disclosure will refer to such combination as simply EPROM for ease of disclosure; however, an artisan will recognize from the disclosure herein that the information element can include the ROM, the RAM, single wire memories, combinations, or the like.

The information element can advantageously store some or all of a wide variety data and information, including, for example, information on the type or operation of the sensor, type of patient or body tissue, buyer or manufacturer information, sensor characteristics including calculation mode data, calibration data, software such as scripts, executable code, or the like, sensor electronic elements, sensor life data indicating whether some or all sensor components have expired and should be replaced, encryption information, monitor or algorithm upgrade instructions or data, or the like. In some embodiments, the information element can be used to provide a quality control function. For example, the information element may provide sensor identification information to the system which the system uses to determine whether the sensor is compatible with the system.

In an advantageous embodiment, the monitor reads the information element on the sensor to determine one, some or all of a wide variety of data and information, including, for example, information on the type or operation of the sensor, a type of patient, type or identification of sensor buyer, sensor manufacturer information, sensor characteristics including history of the sensor temperature, the parameters it is intended to measure, calibration data, software such as scripts, executable code, or the like, sensor electronic elements, whether it is a disposable, reusable, or multi-site partially reusable, partially disposable sensor, whether it is an adhesive or non-adhesive sensor, sensor life data indicating whether some or all sensor components have expired and should be replaced, encryption information, keys, indexes to keys or has functions, or the like monitor or algorithm upgrade instructions or data, some or all of parameter equations, information about the patient, age, sex, medications, and other information that can be useful for the accuracy or alarm settings and sensitivities, trend history, alarm history, sensor life, or the like.

FIG. 7 shows one embodiment of a information element 700. Information element 700 has a read only section 702 and a read write section 704. The read only and read write sections can be on the same memory or on a separate physical memory. In addition, the read only block 702 and the read write block 704 can include multiple separate physical information elements or a single information element. The read only section 702 contains read only information, such as, for example, sensor life monitoring functions (SLM) 706, near expiration percentage 708, update period 710, expiration limit 712, index of functions 714, sensor type or the like. For example, in some embodiments, the index of functions 714 includes configuration information related to what parameters can be measured by the sensor (e.g., ventilation, apnea, respiration rate, etc.). In one embodiment, the information element 700 provides information related to the sensitivity of the sensing element, information related to the mechanical configuration of the sensor, or some other type of configuration or calibration information.

The read write section 704 contains numerous read write parameters, such as the number of times sensor is connected to a monitoring system 716, the number of times the sensor has been successfully calibrated 718, the total elapsed time connected to monitor system 720, the total time used to process patient vital parameters 722, the cumulative temperature of sensor on patient 726, the expiration status 728. Although described in relation to certain parameters and information, a person of ordinary skill in the art will understand from the disclosure herein that more or fewer read only and read/write parameters can be stored on the memory as is advantageous in determining the useful life of a sensor or some other parameter.

Figure 8:
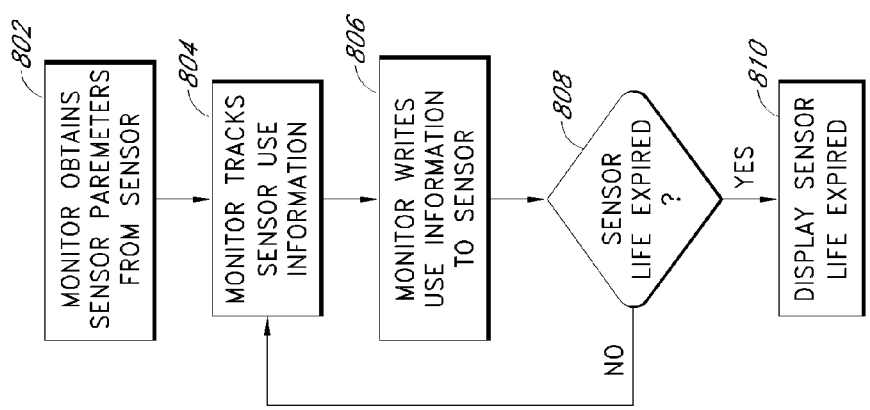
FIG. 8 illustrates a flowchart of one embodiment of a sensor life monitoring method.

FIG. 8 illustrates a flow chart of one embodiment of the read/write process between the monitor and the sensor. In block 802, the monitor obtains sensor parameters from the sensor. For example, in block 802, the monitor can access the read only section 702 of the information element in order to obtain functions such as SLM functions 706, near expiration percentage 708, update period 710, expiration limit 712, and/or the index of functions 714 (FIG. 7). The monitor uses these functions in block 804 to track sensor use information. In block 804, the monitor tracks sensor use information, such as, for example, the amount of time the sensor is in use, the amount of time the sensor is connected, the average temperature, as well as any other stress that can be experienced by the sensor. The monitor then writes this use information on a periodic basis to the sensor at block 806. At decision block 808, the monitor decides whether or not the sensor life is expired based on the obtained parameters from the sensor and the use information. If the sensor's life has not expired at block 808, then the system returns to block 804 where the monitor continues to track sensor use information. If, however, at decision block 808 the monitor decides that the sensor life has expired, the monitor will display a sensor life expired at block 810.

Sensor use information can be determined in any number of ways. For example, in an embodiment, the time period in which power is provided to the sensor is determined and an indication stored in memory. In an embodiment, the amount of current supplied to the sensor is monitored and an indication is stored in memory. In an embodiment, the number of times the sensor is powered up or powered down is monitored and an indication is stored in memory. In an embodiment, the number of times the sensor is connected to a monitor is tracked and an indication is stored in memory. In an embodiment, the number of times the sensor is placed on or removed from a patient is monitored and an indication is stored in the memory. The number of times the sensor is placed on or removed from a patient can be monitored by monitoring the number of probe off conditions sensed, or it can be monitored by placing a separate monitoring device on the sensor to determine when the sensor or portions thereof are sensor depressed, opened, removed, replaced, attached, etc.

In an embodiment, the average operating temperature of the sensor is monitored and an indication stored. This can be done, for example, through the use of bulk mass as described above, or through directly monitoring the temperature of the sensing element, or the temperature of other parts of the sensor. In an embodiment, the number of different monitors connected to the sensor is tracked and an indication is stored in memory. In an embodiment, the number of times the sensor is calibrated is monitored, and an indication is stored in the memory. In an embodiment, the number of patients which use a sensor is monitored and an indication is stored. This can be done by, for example, by storing sensed or manually entered information about the patient and comparing the information to new information obtained when the sensor is powered up, disconnected and/or reconnected, or at other significant events or periodically to determine if the sensor is connected to the same patient or a new patient.

In an embodiment, a user is requested to enter information about the patient that is then stored in memory and used to determine the useful sensor life. In an embodiment, a user is requested to enter information about cleaning and sterilization of the sensor, and an indication is stored in the memory. Although described with respect to measuring certain parameters in certain ways, a person of ordinary skill in the art will understand from the disclosure herein that various electrical or mechanical measurement can be used to determine any useful parameter in measuring the useful life of a sensor.

The monitor and/or the sensor determines the sensor life based on sensor use information. In an embodiment, the monitor and/or sensor uses a formula supplied by the sensor memory to measure the sensor life using the above described variables. In an embodiment, the formula is stored as a function or series of functions, such as SLM functions 706. In an embodiment, experimental or empirical data is used to determine the formula used to determine the sensor's life. In an embodiment, damaged and/or used sensors are examined and use information is obtained in order to develop formulas useful in predicting the useful sensor life.

In an embodiment, a formula or a set of formulas is stored in the monitor's memory. An indication of the correct formula or set of formulas to be used by the monitor is stored in the sensor. The indication stored on the sensor is read by the monitor so that the monitor knows which formula or series of formulas are to be used in order to determine the useful life of the sensor. In this way, memory space is saved by storing the functions or set of functions on the monitor's memory and only storing an indication of the correct function or functions to be used on the sensor memory. Further details regarding embodiments of sensor information elements and systems and methods for monitoring sensor life can be found in U.S. Publication No. 2008/0088467, which is hereby incorporated in its entirety by reference herein.

Attachment Subassembly

The acoustic sensor can also include an attachment subassembly configured to press the sensor against the patient's skin with a pre-determined amount of force. The attachment subassembly can include lateral extensions symmetrically placed about the sensor such as wing-like extensions or arms that extend from the sensor. In other embodiments, the attachment subassembly has a circular or rounded shape, which advantageously allows uniform adhesion of the attachment subassembly to an acoustic measurement site. The attachment subassembly can include plastic, metal or any resilient material, including a spring or other material biased to retain its shape when bent so as to act in a spring-like manner to advantageously press the sensor against the patient. Moreover, the attachment subassembly can also include an attachment layer which may interact with the elongate member so as to adhesively attach to the patient without peeling off of the patient.

Figure 9A:
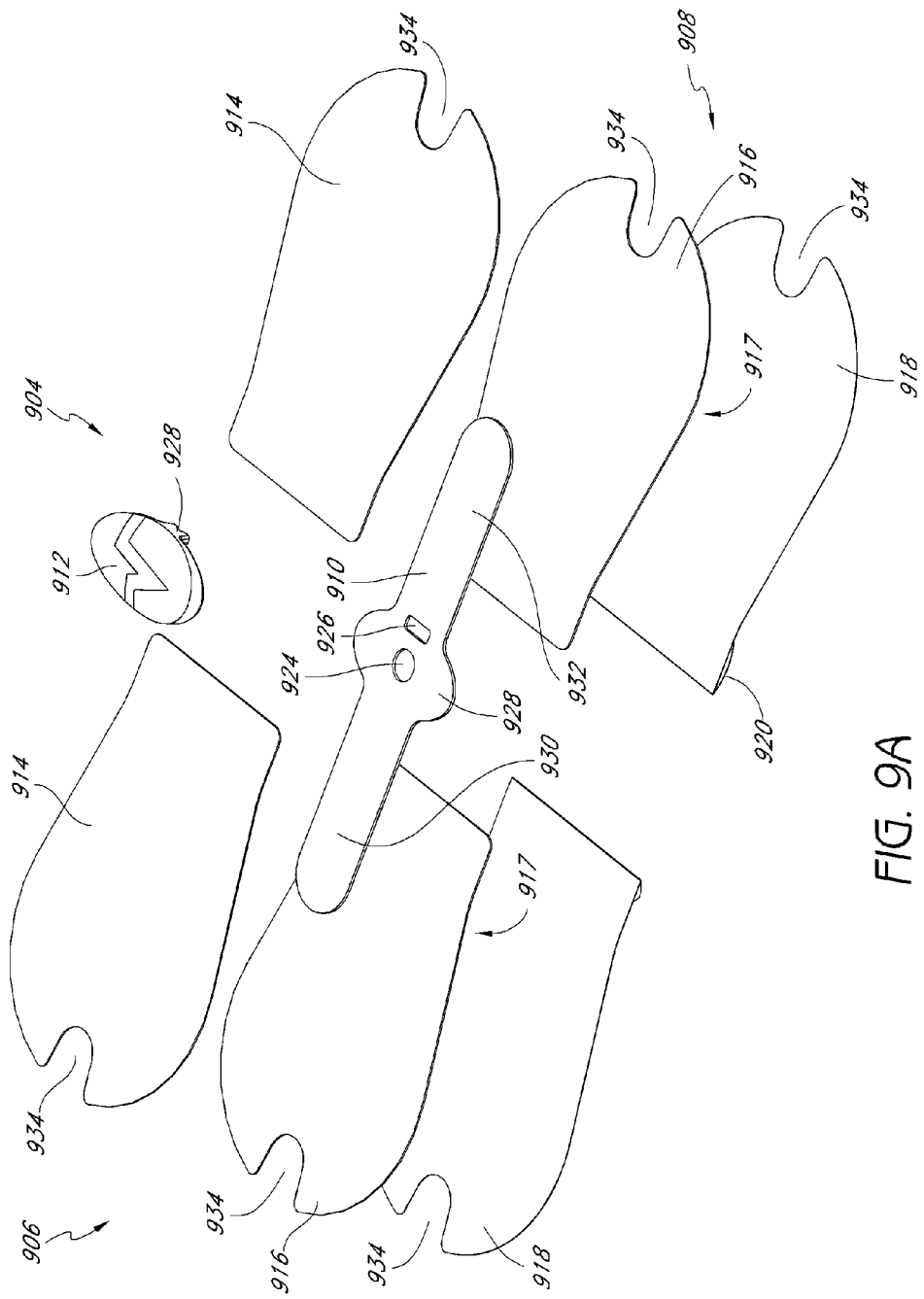
FIG. 9A is a perspective, exploded view of an attachment subassembly compatible with any of the sensor assemblies of FIGS. 1A-2E and 6A-6E according to an embodiment of the disclosure.

FIG. 9A is a perspective, exploded view of an attachment subassembly 904 according to an embodiment of the disclosure. The attachment subassembly 904 may be the attachment subassembly 204 of FIG. 2. The attachment subassembly 904 couples a sensor, such as the sensor subassembly 202, to the skin of the patient. The attachment subassembly 904 includes first and second elongate portions 906, 908 each comprising top tape portions 914, bottom tape portions 916 and liner portions 918. The attachment subassembly 904 further includes a button portion 912 which mechanically mates the attachment subassembly 904 to the sensor subassembly. The attachment subassembly 904 is sometimes referred to as an attachment element or spring assembly.

A elongate member 910 includes a strip of resilient material in certain embodiments. For example, the elongate member 910 includes a resilient, bendable material which rebounds readily after being bent, is semi-rigid, acts as a spring or is elastic or semi-elastic. The elongate member 910 of the illustrated embodiment is sandwiched between the top and bottom tape portions 914, 916 when the attachment subassembly 904 is assembled. The elongate member 910 includes first and second tongue segments 930, 932 which form part of the first and second elongate portions 906, 908, respectively. The elongate member 910 may be referred to as or may include a spring portion. For example, the tongue segments 930, 932 may be described as a spring portion of the elongate member 910. The entire elongate member 910 may be referred to as a spring portion in other embodiments. The elongate member 910 further includes a generally circular center portion 928. The circular portion 928 includes one or more holes 924, 926 for receiving one or more mating features 928 on the button 912. The elongate member 910 includes plastic in one embodiment.

For each of the first and second elongate portions 906, 908, the underside of the top tape portion 914 includes an adhesive substance which adheres to the top of the bottom tape portion 916 and to the top of the tongue segments 930, 932 of the elongate member 910 in an assembled configuration. In addition, the underside of the bottom tape portion 916 includes an adhesive substance which is revealed when the liner portion 918 is removed from the bottom tape portion 916. For example, the user can remove the liner portion 918 by pulling on the tab portion 920. The bottom tape portion 916 of each of the first and second elongate portions 906, 908 can then be attached to the skin of the patient. The portion of the elongate portions 906, 908 which attach to the patient are sometimes referred to as attachment portions 917. In some embodiments, the attachment portions are positioned on other portions of the attachment subassembly 904 rather than on the bottom tape portion 916, such as, for example, directly on the elongate member 910.

Figure 9B:
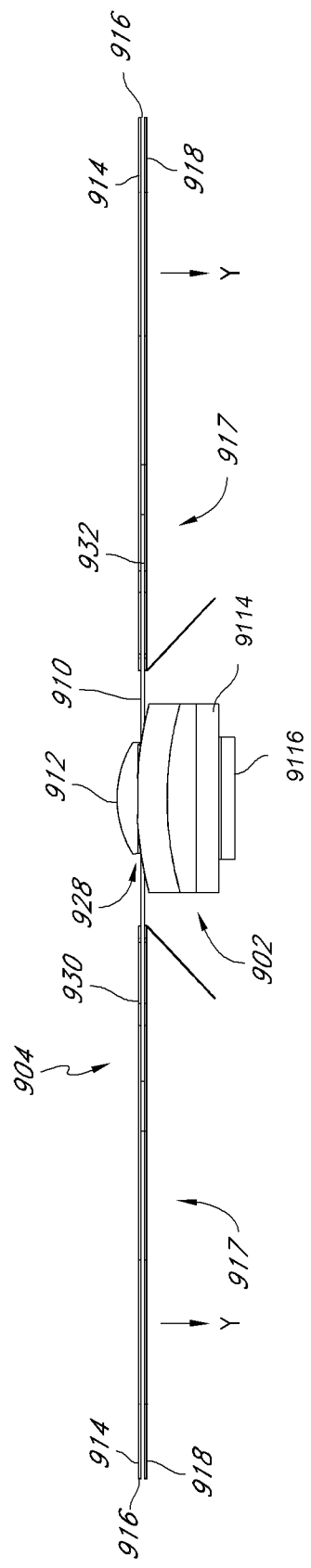
FIG. 9B is a side view of a sensor subassembly that includes the attachment subassembly of FIG. 9A according to embodiments of the disclosure.

FIG. 9B is a side view of the attachment subassembly 904 attached to a sensor subassembly 902. The sensor subassembly 902 may be the sensor subassembly 202 of FIG. 2 or some other sensor subassembly. The attachment subassembly 904 advantageously improves the connection between the patient's skin and the sensor subassembly 902, providing better sensor performance and more efficient use. The elongate member 910 includes a resilient material which allows the first and second tongue segments 930, 932 and the corresponding first and second elongate portions 906, 908 to be bent from a first, unattached position in the direction y such that the first and second elongate portions 906, 908 can be adhesively attached to the patient's skin at a second, attached position. While the elongate member 910 is positioned generally on the top of the sensor subassembly 902 in the illustrated embodiment, other configurations are possible. For example, in some embodiments, the elongate member extends from a middle portion of the sensor subassembly 954 such as from a middle portion of the support frame. In one embodiment, for example, the elongate member 910 includes two or more separate pieces which attach to and extend from opposing sides of the sensor subassembly 954. In another embodiment, the elongate member 910 includes one integral piece which extends through the body of the sensor subassembly 954 and includes two or more arms which extend from opposing sides of the sensor subassembly 954.

In the bent, attached, configuration, the elongate member 910 is in tension. As such, the center portion 928 of the elongate member 910 urges downward, towards the skin of the patient in the direction y in order to achieve equilibrium with the tongue segments 930, 932. The center portion 928 will therefore exert a predetermined force in the y direction on the top of the sensor subassembly 902, advantageously biasing the contact portion 9116 of the acoustic coupler 9114 against the patient's skin. The elongate member 910 thereby provides an improved contact between the skin and the sensor subassembly 902. For example, the elongate member 910 provides greater pressure and/or more uniform pressure between the skin and the sensor subassembly 902 in certain embodiments. The improved coupling also advantageously enhances the reliability of sensor measurements. Moreover, because the spring-like characteristics of the spring portion of the elongate member 910 may vary based on the stiffness of the spring portion, the predetermined force with which the sensor subassembly 902 is pressed against the skin may be determined at least in part based on a stiffness of the spring portion. In addition, the because the elongate member 910 will generally remain in tension while sensor is attached to the patient, the attachment subassembly 904 will generally apply a continuous force on the sensor subassembly 954.

The attachment subassembly 904 is further configured to advantageously allow for a continued secure connection between the sensor subassembly and the patient in the event of stretching of the patient's skin. Because the elongate member is in tension when in the bent, attached, configuration, the tongue segments 930, 932 will urge the attachment portions 917 at least partially laterally, away from the sensor subassembly 902. As such, the patient's skin may stretch laterally, away from the sensor subassembly 902. However, as the skin stretches, the elongate member 910 is configured such that the center portion 928 will apply an increased force on the sensor subassembly 902. The amount of increased force may correspond to the amount of stretching, for example. As such, the attachment subassembly 904 is configured to apply a continuous force on the sensor subassembly 904, such as to the frame of the sensor subassembly 904, thereby pressing it into the patient's skin as the medical patient's skin stretches.

The attachment subassembly 904 may be provided in a variety of alternative configurations as well. For example, the elongate member 910 may bend away from the frame 218 when the sensor assembly 201 is not attached to the patient. In one embodiment the elongate member 910 is formed in a pre-biased configuration so as to increase the amount of pressure the attachment subassembly 904 exerts on the connection between the sensor subassembly 902 and the skin. For example, in one embodiment, the elongate member 910 is not flat but is instead formed in a curved configuration such that the tongue segments 930, 932 are bent upwards, away from the skin prior to adhesion of the sensor subassembly 902 to the skin. Accordingly, when the tongue segments 930, 932 and the elongate portions 906, 908 are bent downwards to attach the sensor to the patient, greater pressure is exerted by the center portion 928 of the elongate member 910 on the sensor subassembly 902 due to the bias that is built into the elongate member 910. In other embodiments, different materials or components may be used or combined. For example, in one embodiment, the elongate member includes a metal material.

In some embodiments, the attachment subassembly 904 itself is used to measure one or more sensor to skin coupling parameters. For example, in one embodiment the attachment subassembly 904 includes an auxiliary sensor (not shown) which can provide an output signal indicative of the actual force being applied by the sensor subassembly 902 on the skin. The elongate member 910, for example, may include a strain gauge which can measure the strain of the elongate member 910. The strain measurement may then be used, for example, to determine the force being applied by the sensor subassembly on the skin. In one embodiment, the strain gauge includes a Wheatstone bridge circuit. In certain embodiments, the signals from the auxiliary sensor may be communicated to electronics on the sensor assembly for further processing, such as to one of the processors and/or information elements described herein. In other embodiments, separate electrical leads may be used to communicate the signals from the pressure sensor to the patient monitor.

Measurements from the auxiliary sensor may be used for a variety of purposes. Measurements from an auxiliary sensor such as the strain gauge may be used, for example, to determine whether the sensor subassembly 902 is coming loose from the skin or otherwise not in sufficient connection with the skin to produce a reliable measurement. For example, since the skin is elastic, it may stretch over time, particularly when attached to a sensor 201. Therefore, providing a strain gauge or other pressure, strain or tension, etc., measuring device with the backbone 910 allows the physiological monitoring system 100 to intelligently monitor the quality of the sensor-to-skin coupling, and adapt to changes in the coupling condition. In this way, the monitor 100 may provide an output signal based on a measured physiological signal, such as an acoustic sound coming from within the patient, and a coupling signal, indicating the quality of the sensor-to-skin coupling. The coupling signal may include a strain, pressure, tension or other signal indicative of the sensor-to-skin coupling.

The system may indicate an alarm condition and/or may automatically shut-down operation of the sensor in the event of a poor connection, for example. In such embodiments the attachment subassembly 904 triggers an alarm. The auxiliary sensor readings may also be used to calibrate the sensor. For example, if the auxiliary sensor indicates that the connection between the sensor subassembly 902 and the skin is relatively weak, the system may increase the sensitivity of the sensor or increase the gain of an amplifier configured to amplify the sensor signal. On the other hand, if the auxiliary sensor indicates that the connection between the sensor subassembly 902 and the skin is relatively strong, the system may decrease the sensitivity of the sensor or decrease the gain of an amplifier configured to amplify the sensor signal. In some embodiments, the user may optionally change the calibration of the sensor based on the auxiliary readings and the system does not automatically change the calibration.

The auxiliary sensor reading may be used to evaluate physiological measurement signals from the sensor (e.g., measurements relating to ventilation, apnea, respiration rate and the like). For example, if there is a change in a physiological measurement, the system may evaluate the auxiliary sensor reading to determine whether the change in the physiological measurement was actually at least in part due to a faulty connection between the sensor and the patient. In another embodiment, the auxiliary sensor may be connected to a portion of the sensor subassembly 902. For example, in one embodiment, the contact portion 9116 of the acoustic coupler 9114 includes a pressure sensor which measures the force being applied to the skin.

Various embodiments of auxiliary sensors and auxiliary sensor configurations may be provided. For example, an auxiliary sensor may be included on other parts of the sensor assembly instead of, or in addition to, the attachment subassembly. For example, the sensor subassembly includes an auxiliary sensor in one embodiment. In various embodiments, the auxiliary sensor may be a push-button or scale type pressure sensor, a temperature sensor or the like.

As discussed above, in certain embodiments the sensor is resposable and has both disposable and reusable parts. For example, in one embodiment the attachment subassembly 904 or portions thereof are disposable and/or removably attachable from the sensor subassembly 902. The attachment subassembly 904 can removably attach to the sensor subassembly via a snap-fit mechanism. The attachment subassembly 904 may removably attach to the sensor subassembly 902 via other mechanisms such as, for example, friction-fit mechanisms, adhesive mechanisms and the like. In various other embodiments, the disposable element, such as the attachment subassembly 904, may attach via one of the attachment mechanisms described in the '345 Patent, such as an attachment mechanism similar to one of those described with respect to column 5, line 15 through column 8, line 26, for example. A removably attachable and/or disposable attachment subassembly 904 can be advantageous for several reasons. For example, the attachment subassembly 904 or components thereof (e.g., the adhesive portions) may wear out relatively quickly in comparison to the other components of the sensor assembly (e.g., in comparison to the sensor subassembly 902) or may become soiled due to direct adhesive contact with the skin. Moreover, the attachment subassembly 904 may be relatively less costly to manufacture than the other components of the sensor assembly. As such, in the event that attachment subassembly 904 becomes damaged, a removably attachable and/or disposable attachment subassembly 904 can reduce costs because a user will not have to replace the entire sensor assembly. In addition, in the event that the attachment subassembly 904 becomes soiled, the user can optionally replace only the attachment subassembly 904 rather than take the time to sterilize it for subsequent use.

The attachment subassembly 904 may further include an information element (not shown) which can provide information to the system. The information element may be one of the information elements described herein or may be another information element. For example, the information element may monitor the life of the sensor assembly, the attachment subassembly 904 or another part of the sensor assembly in the manner described above with respect to FIGS. 7 and 8. In one embodiment, the information element may store the information provided by an auxiliary sensor on the attachment subassembly 904, such as, for example, the strain gauge described above. The information element may provide information to the system which can be used to configure the sensor. In some embodiments, the information element can be used to provide a quality control function. For example, the information element may provide identification information to the system which the system uses to determine whether the attachment subassembly 904 is compatible with the system. In another embodiment, the information element provides use information related to the amount of use of the attachment subassembly 904.

As mentioned above, the attachment subassembly can also include an attachment layer which may interact with the elongate member so as to adhesively attach to the patient without peeling off of the patient. The attachment subassembly may include an elongate member that includes a resilient material and is coupled to the attachment layer. The attachment layer may include one or more of the bottom tape portions 916 and the top tape portions 914 of FIGS. 9A-9B, for example. For example, the elongate member can be configured to move from a first position in which the elongate member is substantially parallel to the attachment layer to a second position in which the elongate member is inclined at an angle with respect to the attachment layer when the attachment layer is attached to the medical patient.

FIGS. 9C-D show an embodiment of an attachment subassembly 950 attached to the patient's skin 951 and in an unattached configuration, respectively. The attachment subassembly 950 includes an attachment element 952 supported by the sensor subassembly 954 and extending beyond a first side 956 of the sensor subassembly 954.

The attachment element 952 includes an attachment layer 958 having a patient attachment surface 960. As shown, an end 975 of the elongate member 974 is positioned a predetermined distance from an edge 976 of the attachment layer 958. A connecting portion 966 of the attachment element 952 is attached to the top of the elongate member 974, coupling the elongate member 974 to the attachment layer 958. As shown in FIG. 9C, the elongate member 974 is positionable in a first position in which the elongate member 974 is substantially parallel or parallel to the attachment layer 958. The elongate member 974 is positioned in the first position, for example, when the attachment surface 960 of the attachment layer 958 is not attached to the skin 951 of the patient. Moreover, as shown in FIG. 9D, the elongate member 974 is configured to move to a second position from the first position in which the elongate member 974 is inclined at an angle θ with respect to the attachment layer when the attachment surface 960 is attached to the skin 951 of the patient.

When in the attached, bent configuration of FIG. 9D, the elongate member 974 will urge upward. As such, the elongate member 974 will urge the connecting portion 966 and thus the attachment layer 958 upward as well. Moreover, movement of the sensor subassembly 954 due to acoustic vibrations or movement of the patient, for example, will urge the elongate member 974 and thus the attachment layer 958 away from the skin of the patient. However, the elongate member 974 is connected to the attachment layer such that neither the movement of the sensor subassembly 954 with respect to the attachment layer nor the force from the elongate member 974 cause the attachment layer to detach from the medical patient during use.

As shown in FIG. 9D, in the bent, attached configuration, the elongate member 974 and the attachment layer 958 are not adhesively or otherwise connected in the region 978 formed between the top of the attachment layer 958 and the underside of the elongate member 974, advantageously allowing for the elongate member 974 to incline with respect to the attachment layer 958. In addition, the elongate member 974 is positioned at a distance from the edge 976 of the attachment layer 958 and the force incident on the attachment layer 958 in the upward direction from the elongate member 974 is therefore distributed near the end 975 of the elongate portion 974 rather than at the edge 976. As such, the force is distributed away from the edge 976 of the connection of the attachment layer 958 and the skin. Upward force away from the edge of attachment layer 958 has less of a tendency to peel the attachment layer 958 off of the skin, thus reducing unintended detachments and thereby providing for improved and more reliable measurement.

The distance that the end 975 of the elongate member 974 and is positioned from the edge 976 of the attachment layer 958 is selected so as to reduce the tendency of peel off. For example, the end 975 of the elongate member 974 may be positioned near the attachment layer's 958 center in certain embodiments. In addition, the angle θ may be a function of various factors such as, for example, the stiffness of the elongate member 974. The angle θ may also be a function of the distance the end 975 of the elongate member travels to the skin from the first position to the second position. This distance may correspond, in one embodiment, to approximately height of the sensor subassembly 954 where the elongate member 974 is positioned on the top of the sensor subassembly 954, for example. In some alternative embodiments, however, the connecting portion couples to the attachment layer 958 substantially near or at the edge 976 of the attachment layer 958.

As shown, the attachment subassembly 950 further includes a second attachment element 972 extending from a second side 970 of the sensor subassembly 954 substantially opposite the first side 956. In some embodiments, more than two attachment elements can be included. For example, in one embodiment, a third and fourth attachment element extend beyond opposing third and fourth sides of the sensor subassembly 954. In one embodiment, only one attachment element is included. In some embodiments, the connecting portion 966 may include a tape portion such as the top tape portion 914 described above.

The connecting portion 966 may further include an elongate member 974 comprising a resilient material. The elongate member may be, for example, the elongate member 910 described above or some other elongate member or spring. The elongate member 974 may be coupled to the sensor subassembly 954 but not be substantially coupled to the attachment layer 958. Like the elongate member 910, the elongate member 974 may be configured to apply a predetermined force on the frame such that the sensor subassembly is pressed against a measurement site of the medical patient during use.

Referring back to the attachment subassembly 904 of FIGS. 9A-B, the bottom surface of the bottom tape portion 916 includes an adhesive which attaches to the patient's skin. Moreover, the underside of the top tape portion 914 includes an adhesive and attaches to the top of the elongate member 910 and to the top of the bottom tape portion 916. As such, the top tape portion 914 couples the elongate member 910 to the bottom tape portion 918. Accordingly, the top tape portion acts as a the connecting portion, such as the connecting portion 966 described above, and the bottom tape portion 916 acts as the attachment layer 958, as described above.

Moreover, the top surface of the bottom tape portion (attachment layer) 916 is not adhesive and thus does not adhere to the bottom of the elongate member 910. As such, the top tape portion 914 and the elongate member 910 the elongate member 910 is positionable in a first position in which the elongate member 910 is substantially parallel or parallel to the bottom tape portion 918 and is configured to move to a second position from the first position in which the elongate member 910 is inclined at an angle θ with respect to the bottom tape portion 918 or attachment layer when the attachment surface 960 is attached to the skin 951 of the patient. As such, and as described above with respect to FIGS. 9C-D, the upward force from the elongate member 910 in the bent, attached configuration will be distributed away from the edge 976 of the connection of the bottom tape portion 918 and the skin, thereby reducing the incidence of peel off or other unintended detachment of the sensor.

Referring again to FIGS. 9C-D, the connecting portion 966 and the attachment layer 958 may form an integral piece. In other embodiments, as discussed above, the connecting portion 966 and the attachment layer 958 include separable units, such as bottom and top layers of tape, for example. In certain embodiments where the connecting portion 966 includes adhesive, only select portions of the bottom surface of the connecting portion 966 include such adhesive. For example, in one embodiment, only the portion of the connecting portion 966 which contacts the elongate member 974 includes an adhesive. In another embodiment, only a select portion of the connecting portion 966 which adhesively attaches to the attachment layer 958 includes adhesive. In yet other configurations, the connecting portion includes adhesive which connects to both the elongate member 974 and to a select portion which attaches to the attachment layer 958.

Figure 10:
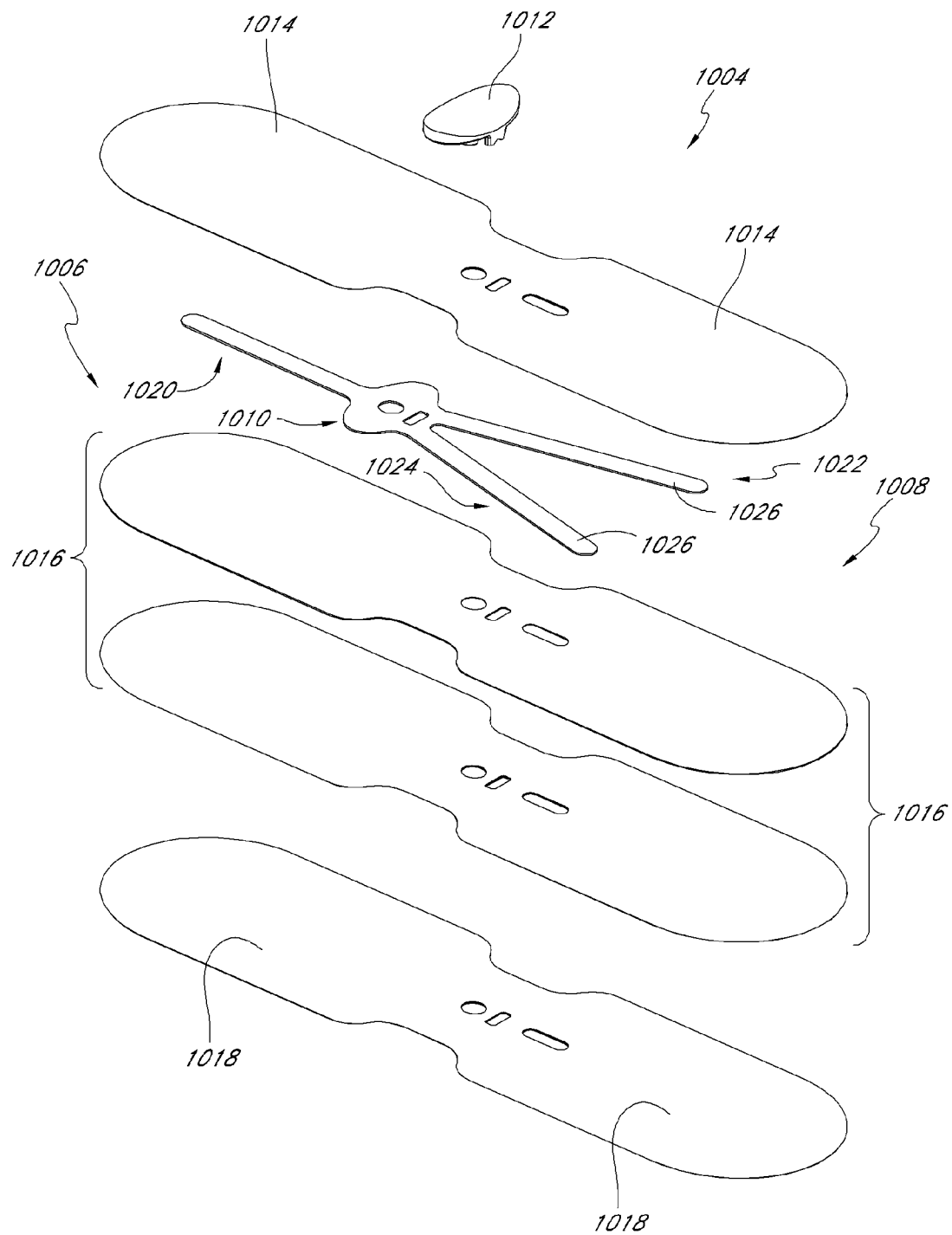
FIG. 10 is a perspective, exploded view of an attachment subassembly compatible with any of the sensor assemblies of FIGS. 1A-2E and 6A-6E according to another embodiment of the disclosure.

FIG. 10 is a perspective, exploded view of an attachment subassembly 1004 compatible with any of the sensor assemblies of FIGS. 1A-2E and 6A-E according to another embodiment of the disclosure. The attachment subassembly 1004 may be the attachment subassembly 604 of FIG. 6, for example. Similar to other attachment elements described herein, the attachment subassembly 1004 couples a sensor, such as the sensor subassembly 602, to the skin of the patient and can be configured to press the sensor against the patient's skin with a pre-determined amount of force, acting in a spring-like manner to press the sensor against the measurement site. The attachment subassembly 1004 can also be configured such that movement of the sensor with respect to the attachment subassembly 1004 does not cause the attachment element to peel off or otherwise detach from the patient during use. For example, the attachment subassembly 1004 may operate in a similar manner and provide similar advantages and functions to other attachment elements described (e.g., the attachment subassembly 900 described with respect to FIGS. 9A-9D).

The attachment subassembly 1004 has a first end 1006 and a second end 1008. The attachment subassembly 1004 includes a top tape portion 1014, bottom tape portions 1016, liner portion 1018, and an elongate member 1010. The attachment subassembly 1004 further includes a button 1012 which mechanically mates the attachment subassembly 1004 to the sensor subassembly (not shown). In one embodiment, the top tape portion 1014 is translucent and includes adhesive on its underside. The top tape portion adheres to the top of the elongate member 1010 and the top of the upper bottom tape portion 1016. The upper bottom tape portion 1016 includes printed text that is visible through the translucent top tape portion 1016. The underside of the upper bottom tape portion 1016 adheres to the top of the lower bottom tape portion 1016. The liner 1018 protects the bottom tape portion and can be peeled off to expose adhesive on the underside of the lower bottom tape portion 1016.

The attachment subassembly 1004 is sometimes referred to as an attachment element or spring assembly. The elongate member 1010 of FIG. 10 can include any of variety of shapes, including a forked or "Y" shape, and the elongate member 1010 includes a first end 1020 having one leg 1022 and a second end 1024 having two legs 1026.

The forked structure provides certain advantages. For example, the multiple-legged structure of the second end 1024 may provide an increased amount of spring action in pressing the sensor against the skin, or may provide a more evenly distributed and/or efficiently directed force.

The single-legged structure of the first end 1020 allows for enhanced adhesion to the measurement site under certain circumstances, such as when the first elongate portion 1006 is attached to an uneven or bumpy region of the patient's skin, or to a measurement site that is otherwise relatively difficult to attach to. For example, because the leg of the first end 1020 is centrally located and thus removed from the edges of the tape portions 1014, 1016, it can reduce the tendency for the first elongate portion 1006 to peel-off of the patient. Moreover, the single-legged structure may have relatively less spring action or restoring force than a multiple-legged structure, also reducing peel-off tendency.

In one use scenario, first end 1006 of the attachment element 1004 including the single-legged first end 1020 of the backbone 1010 are placed over the patient's Adam's apple, providing enhanced adhesion to the relatively uneven Adam's apple region. In the example use scenario, the sensor assembly is further wrapped around the side of the patient's neck such that the sensing element is positioned across the side of the front of the patient's neck. Finally, the second end 1008 of the attachment element 1004 including the multi-legged structure of the second end 1022 of the backbone 1010 are placed generally on the side of the patient's neck, which is relatively less bumpy than the Adam's apple region. In such a case, the forked structure of the elongate member 1010 allows for both: (1) robust adhesion over the patient's Adam's apple due to the single-legged structure of the first end 1020; and (2)

improved spring-like behavior in pressing the sensor against the measurement site due to the double-legged structure of the second end 1022.

In other embodiments, the first end 1020 may also be forked and the elongate member 1010 may generally comprise an "X" shape. One or more of the first and second ends 1020, 1022 may include more than two legs. In yet other embodiments, both of the first and second ends 1020, 1022 may include only one leg in a manner similar to the elongate member 910 of FIG. 9.

Patient Anchor

Movements such as yanking, jerking or pulling of the cable may cause stress on the adhesive connection between the sensor assembly 201 and the patient. Such stress may be caused by movement of the patient, movement of the monitor, or accidental pulling on the cable by medical personnel, for example. It can therefore be beneficial to secure the cable to the body at a point between the ends of the cable, thereby decoupling potential movement of the cable from the adhesive connection between the sensor assembly 201 and the patient. As such, the cable assembly can include a patient anchor which advantageously secures the cable to the patient at a point between the ends of the cable. The patient anchor may include one or more panels which adhesively secure the cable to the body, for example.

Figure 11A:
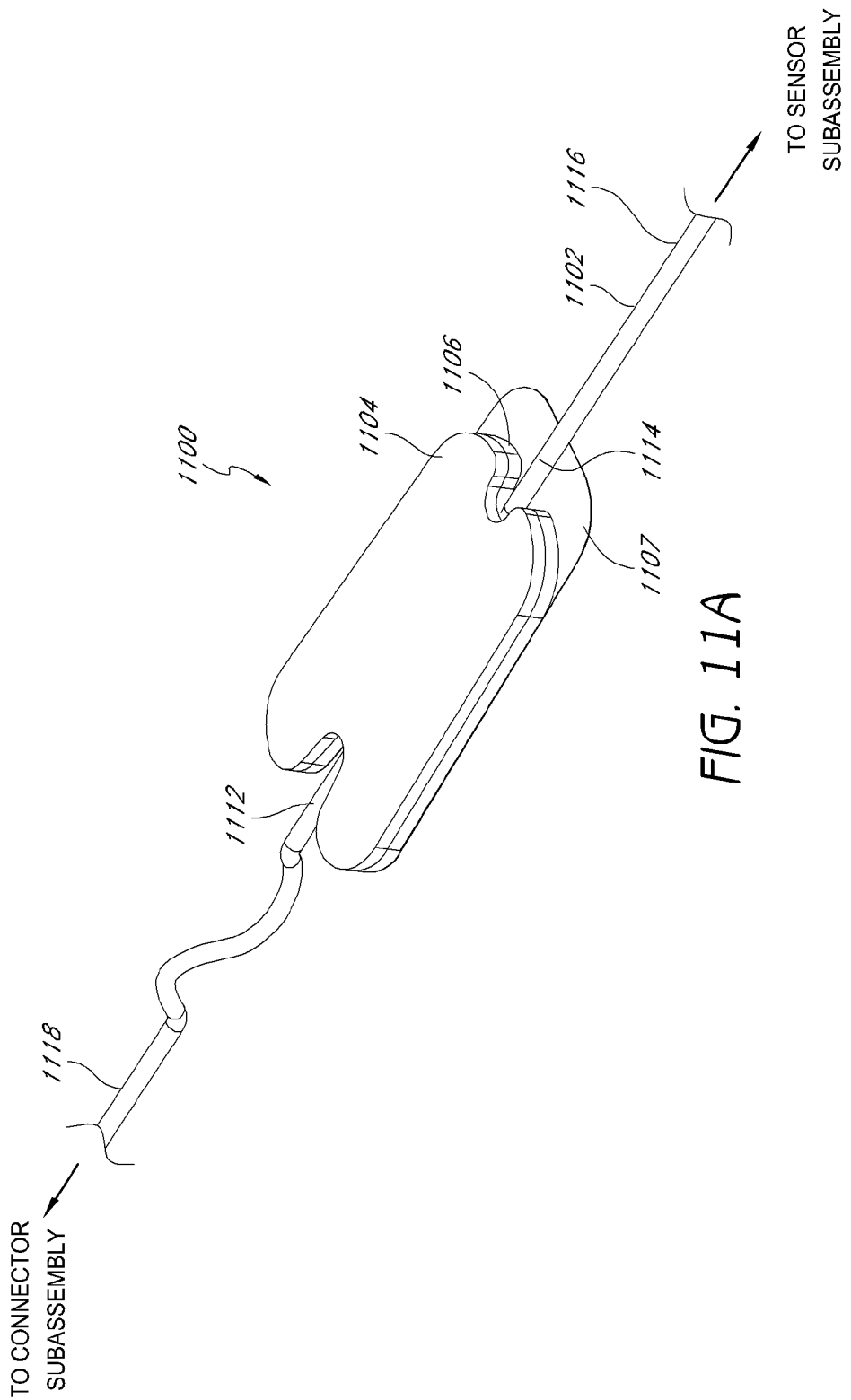
FIG. 11A is a perspective view of a patient anchor compatible with any of the sensor assemblies of FIGS. 1A-2E and 6A-6E according to an embodiment of the disclosure.

FIG. 11A is a perspective view of a patient anchor 1100 according to one embodiment of the disclosure. The patient anchor 1100 may be the patient anchor 203 of FIG. 2A or some other patient anchor. However, in some embodiments, the sensor assembly 201 does not include any patient anchor. The patient anchor may be referred to as forming part of a cable assembly. As shown, the patient anchor 1100 is attached to the sensor cable 1102 between a sensor subassembly (not shown) and a sensor connector subassembly (not shown) such as one of the sensor subassemblies and sensor connector subassemblies described herein. As will be described, the patient anchor 1100 advantageously provides a intermediate point of contact between the sensor assembly and the patient, thereby reducing the stress on the point of contact between the patient and the sensor subassembly. Such stress may be caused by jerking or yanking of the cable 1102, for example. The patient anchor is positioned on the cable 1102 between a proximal segment 1116 of the cable 1102 and a distal segment 1118 of the cable 1102. The proximal segment 1116 terminates in a proximal end (not shown) configured to attach to the sensor subassembly and the distal segment 1118 terminates in a distal end configured to connect to a sensor connector subassembly.

Figure 11B:
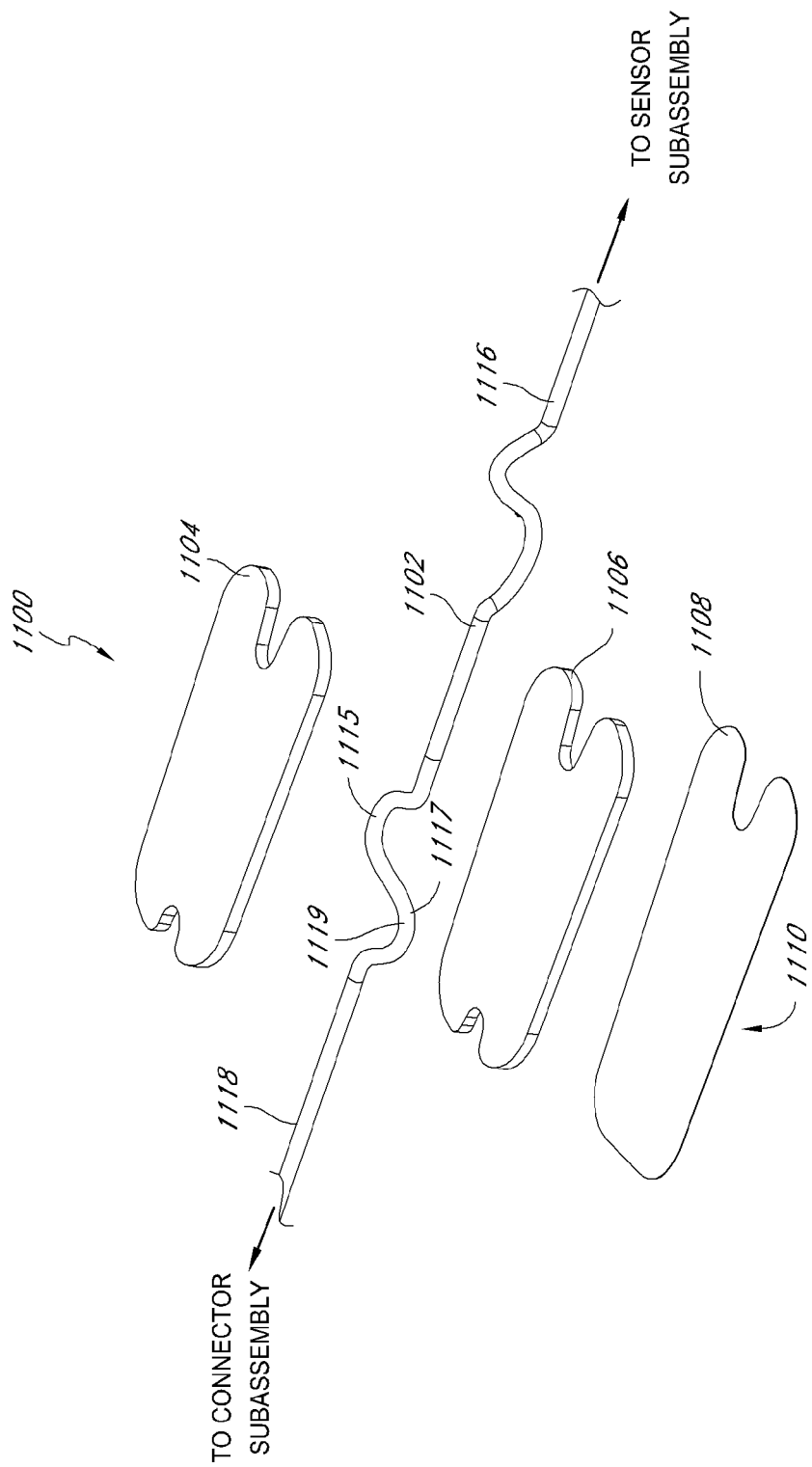
FIG. 11B is a perspective, exploded view of the patient anchor of FIG. 10A.

FIG. 11B is a perspective, exploded view of a patient anchor 1100 according to one embodiment of the disclosure. Referring to FIGS. 11A-B, the patient anchor 1100 includes a top anchor panel 1104, a bottom anchor panel 1106, and a liner panel 1108. The top and bottom anchor panels 1104, 1106 adhesively attach to opposing sides of the cable 1102 and to each other while the liner panel 1108 adhesively attaches to the underside of the bottom panel 1106. The underside 1110 of the liner panel is removable from the bottom panel 1106 to reveal an adhesive on the underside of the bottom panel 1106 which is configured to attach to the patient's skin. In various embodiments, the panels 1106, 1108 include rubber, plastic, tape, such as a cloth tape, foam tape, or adhesive film, or other compressible material that has adhesive on one or both of their faces. The liner panel includes an adhesive film or other similar material.

As shown, the cable 1102 is straight at the points at which the cable 1102 enters the patient anchor 1100. However, as shown in FIG. 11B, the cable 1102 includes a bent portion 1119 in the region in which the patient anchor is attached. The shape of the bent portion 1119 further decouples the proximal segment 1116, and thus the adhesive connection between sensor assembly and the patient, from stress incident on the distal segment 1118. This improved decoupling is achieved by providing one or more mechanical bends, such as the bends 1115, 1117, in the cable 1102. The bent portion 1119 may also improve the attachment of the cable 1102 to the panels 1104, 1106 by, for example, providing more cable surface area for the panels 1104, 1106 to attach to. For example, in the illustrated embodiment, the bent portion 1119 is formed in the shape of an "S." The cable 1102 is bent before application of the anchor panels 1104, 1106 which adhere to the cable 1102 and hold bent portion 1119 in place, for example. The bent portion 1119 can be held in place in other ways. For example, in one embodiment, the bent portion 1119 of the cable 1102 is relatively rigid.

Figure 12:
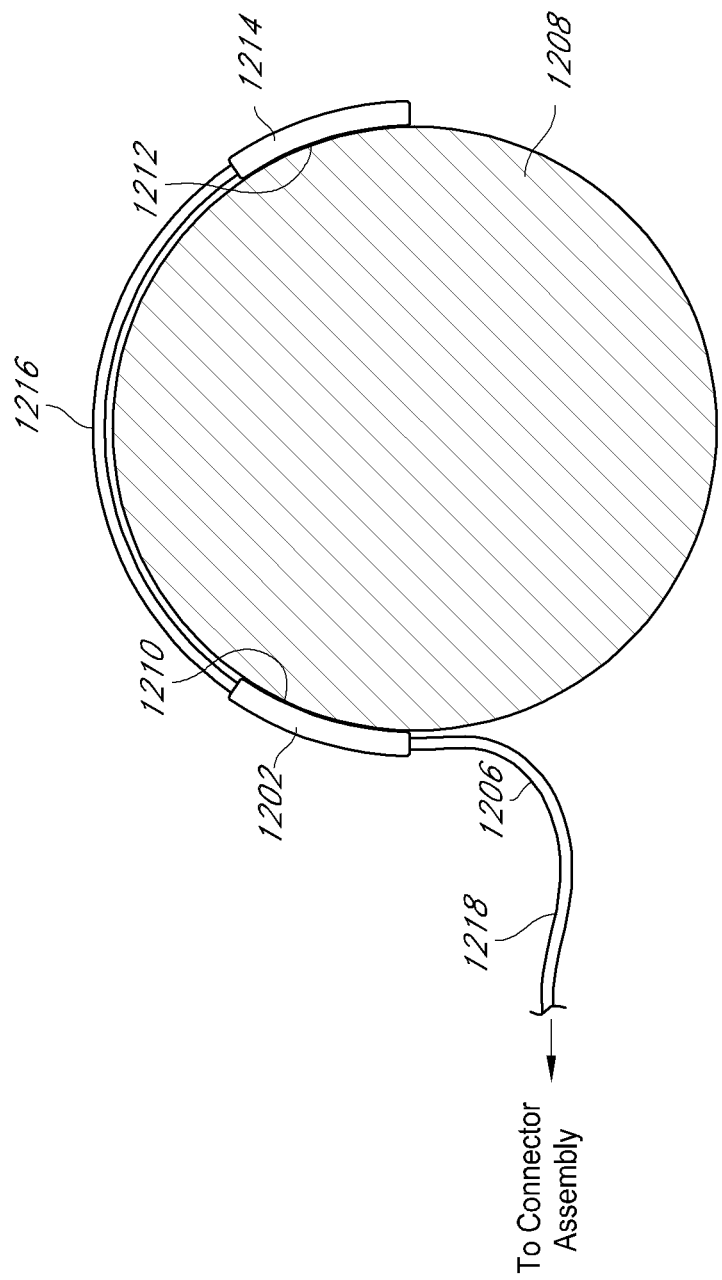
FIG. 12 is a top view of a patient anchor and a sensor subassembly attached to a patient according to embodiments of the disclosure.

FIG. 12 is a top view of a patient anchor 202 and a sensor subassembly element attached to a patient according to one embodiment of the disclosure. As shown with respect to a top cross-sectional view of a patient's neck 1208, the patient anchor 1202 is attached to the patient 1208 at an intermediate point 1210 while the sensor subassembly is attached at the monitoring point 1212. As discussed, the patient anchor advantageously reduces stress on the contact point 1212 between the sensor subassembly and the patient due, for example, to stress from yanking or jerking on the cable 1206. While the patient anchor 1202 is shown attached to the patient's neck, the patient anchor 1202 may be attached elsewhere in some embodiments. For example, in one configuration, the patient anchor 1202 is attached to the patient's upper chest. In various configurations, the anchor 1202 may be attached to the shoulder, arm, or some other portion of the patient. In some cases, the anchor 1202 may be attached to an object other than the patient. For example, the patient anchor 1202 can be attached to the patient's bed or another generally fixed object.

A method of attaching a sensor to a measurement site using a patient anchor, such as the patient anchor 1100, for example includes attaching the sensor to the measurement site. The method further includes attaching the patient anchor to an anchoring location a predetermined distance from the measurement site. As discussed the patient anchor is positioned between a proximal end of a cable coupled to the sensor and a distal end of a cable coupled to a sensor connector. The predetermined distance may be selected such that the proximal segment 1118 of cable 1006 between the sensor subassembly and the patient anchor 1100 provides some slack when the sensor assembly and patient anchor are attached, thereby avoiding any tension on the proximal segment 1118 and any resulting stress on the adhesive connection between the patient and the sensor assembly. Moreover, the predetermined distance may be selected so as to provide a certain maximum amount of slack when the sensor assembly and patient anchor are attached so that the proximal segment 1118 is unlikely to become snagged or pulled during use. The predetermined distance of certain embodiments is also selected such that the length of the proximal segment 1118 is appropriate for attachment of the patient anchor 1100 to a portion of the body relatively well-suited for attachment to the patient anchor, such as a flat or hairless portion of the body. In various embodiments, the predetermined distance is from between about one inch and 12 inches and the length of the proximal segment 1118 is from between 1.5 inches and 18 inches. In other embodiments, the predetermined distance is from between about three inches and six inches and the length of the proximal segment 1018 is from between about four inches and nine inches. In other embodiments, the predetermined distance is less than one inch or greater than 12 inches.

In another embodiment, the patient anchor includes one integral piece and does not include the separate panels 1106, 1108 and a liner 1110. In another embodiment, the bent portion 1119 may not be included, or may be formed into a different shape, such as an "L" shape, for example. In various embodiments, the bent portion 1119 may include any shape that includes one or more pre-formed bends, as described above, or which otherwise decouple stress incident on the distal segment 1116 of the cable 1102 from the adhesive connection between the sensor assembly and the patient. In addition, the proximal and distal ends may be configured to connect to other components. For example, in other embodiments, the distal end is configured to connect to a patient monitor or patient monitor connector. Moreover, in some embodiments, the patient anchor 1100 is attached to the patient or other object via a non-adhesive mechanism. For example, the patient anchor 1100 may comprise a clip or other mechanical attachment mechanism. In on embodiment the anchor 1100 comprises an alligator type clip attachable to a patient's clothing.

An acoustic sensor has been described with respect to certain embodiments. Various combinations of the components and subcomponents described herein are within the scope of the disclosure. For example, in certain embodiments, one or more of the attachment subassembly, the auxiliary sensor, the acoustic coupler, the electrical shielding barrier, the bonding layer, the information element and patient anchor are not included. In one embodiment, for example, the sensor assembly includes all of the aforementioned components except for the auxiliary sensor and the patient anchor. In another embodiment, the sensor assembly includes all of the aforementioned components except for the information element.

Other combinations, omissions, substitutions and modifications are within the scope of the disclosure. It is contemplated that various aspects and features of the systems and methods described can be practiced separately, combined together, or substituted for one another, and that a variety of combination and sub combinations of the features and aspects can be made and still fall within the scope of the disclosure. Furthermore, the systems described above need not include all of the modules and functions described in the preferred embodiments. Accordingly, the present disclosure is not intended to be limited by the recitation of the preferred embodiments, but is to be defined by reference to the appended claims.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. An acoustic sensor assembly comprising: a frame at least partially defining an open cavity; a sensing element configured to output a signal responsive to acoustic vibrations, the sensing element supported by the frame, at least a portion of the sensing element comprising a piezoelectric material that is stretched in tension across the open cavity; electrical contacts electrically coupled with the sensing element and configured to convey an electrical signal corresponding to the signal responsive to the acoustic vibrations; an acoustic coupler supported by the frame and including an inner protrusion that extends into the open cavity and is positioned to apply pressure to at least the portion of the sensing element that is stretched in tension across the open cavity to push a section of the sensing element into the open cavity both when the acoustic sensor assembly is attached to a medical patient and when the acoustic sensor assembly is not attached to the medical patient, the acoustic coupler configured to transmit acoustic vibrations to the sensing element through the acoustic coupler when the acoustic sensor assembly is attached to the medical patient; and an elastic portion attached to the frame and extending at least partially beyond opposite sides of the frame, wherein the elastic portion is configured to apply a predetermined force to the frame through stretching of the elastic portion such that the acoustic sensor assembly is pressed against a measurement site of the medical patient when the acoustic sensor assembly is attached to the medical patient.

2. The acoustic sensor assembly of claim 1, wherein the acoustic coupler further includes an outer protrusion disposed on an outside surface of the acoustic coupler.

3. The acoustic sensor assembly of claim 1, wherein the acoustic coupler electrically isolates the sensing element from the medical patient when the acoustic sensor assembly is attached to the medical patient.

4. The acoustic sensor assembly of claim 1, wherein the acoustic coupler comprises an elastomer.

5. The acoustic sensor assembly of claim 1, wherein the acoustic coupler is configured to evenly distribute pressure on the sensing element.

6. The acoustic sensor assembly of claim 1, wherein the predetermined force is determined at least in part based upon an elasticity of the elastic portion.

7. The acoustic sensor assembly of claim 1, wherein the elastic portion at least partially surrounds the frame when the acoustic sensor assembly is attached to the medical patient.

8. The acoustic sensor assembly of claim 1 further comprising:
a tape portion configured to be attachable to the medical patient so as to attach the acoustic sensor assembly to the medical patient, wherein the elastic portion is attached to the tape portion on a topside of the tape portion, and wherein the elastic portion is attached to a topside of the frame.

9. The acoustic sensor assembly of claim 8, wherein the elastic portion is attached at a middle point of the topside of the tape portion.

10. The acoustic sensor assembly of claim 9, wherein, when the acoustic sensor assembly is attached to the patient, the elastic portion is inclined with respect to the tape portion.

11. The acoustic sensor assembly of claim 1, wherein the elastic portion is permanently affixed to the frame.

12. A method comprising:
using acoustic sensor assembly according to claim 1, attached to a medical patient, to provide a signal responsive to acoustic vibrations indicative of one or more physiological parameters of the medical patient, the acoustic coupler being in contact with the medical patient; and
outputting the signal based on acoustic vibrations transmitted through the acoustic coupler and detected by the sensing element.

13. The method of claim 12 further comprising using the elastic portion of the acoustic sensor assembly to apply a predetermined force to the frame, wherein the acoustic sensor assembly is pressed against the medical patient.

14. A method of using an acoustic sensor assembly according to claim 1, the acoustic sensor assembly attached to a medical patient via the elastic portion such that the acoustic coupler is pressed against the medical patient, the method comprising:
receiving, via the acoustic coupler, acoustic vibrations;
transmitting, via the acoustic coupler, the received acoustic vibrations to the sensing element;
converting, via the sensing element, the transmitted acoustic vibrations into electrical signals; and
providing the electrical signals to the electrical contacts of the acoustic sensor assembly.

15. The method of claim 14, wherein attaching the acoustic sensor assembly to the medical patient causes the acoustic coupler to further push the section of the sensing element into the open cavity.

16. A method of manufacturing an acoustic sensor assembly, the method comprising: providing a frame at least partially defining an open cavity; at least partially supporting, by the frame, a sensing element configured to output a signal responsive to acoustic vibrations, at least a portion of the sensing element comprising a piezoelectric material that is stretched in tension across the open cavity; providing electrical contacts electrically coupled with the sensing element and configured to convey an electrical signal corresponding to the signal responsive to the acoustic vibrations; at least partially supporting, by the frame, an acoustic coupler including an inner protrusion that extends into the open cavity and is positioned to apply pressure to at least the portion of the sensing element that is stretched in tension across the open cavity to push a section of the sensing element into the open cavity both when the acoustic sensor assembly is attached to a medical patient and when the acoustic sensor assembly is not attached to the medical patient, the acoustic coupler configured to transmit acoustic vibrations to the sensing element through the acoustic coupler when the acoustic sensor assembly is attached to the medical patient; and affixing, to the frame, an elastic portion that extends at least partially beyond opposite sides of the frame, wherein the elastic portion is configured to apply a predetermined force to the frame through stretching of the elastic portion such that the acoustic sensor assembly is pressed against a measurement site of the medical patient when the acoustic sensor assembly is attached to the medical patient.

17. The acoustic sensor assembly of claim 16, wherein the predetermined force is determined at least in part based upon an elasticity of the elastic portion.

18. The method of claim 16, wherein the elastic portion is configured to at least partially surrounds the frame when the acoustic sensor assembly is attached to the medical patient.

19. The method of claim 16 further comprising:
providing a tape portion configured to be attachable to the medical patient so as to attach the acoustic sensor assembly to the medical patient, wherein the elastic portion is attached to the tape portion on a topside of the tape portion, and wherein the elastic portion is attached to a topside of the frame.

20. The method of claim 19, wherein the elastic portion is attached at a middle point of the topside of the tape portion.

21. The method of claim 20, wherein, when the acoustic sensor assembly is attached to the patient, the elastic portion is configured to be inclined with respect to the tape portion.

* * * * *

UNITED STATES PATENT AND TRADEMARK OFFICE
CERTIFICATE OF CORRECTION

PATENT NO.          : 9,131,917 B2
APPLICATION NO.     : 14/671367
DATED               : September 15, 2015
INVENTOR(S)         : Valery G. Telfort Page 1 of 1

It is certified that error appears in the above-identified patent and that said Letters Patent is hereby corrected as shown below:

Title Page

In column 2 (page 6, item 56) at line 6, Under Other Publications, change "PCTUS2010052760" to --PCT/US2010/052760--.

In the Specification

In column 17 at line 50, Change "not" to --no--.

In column 39 at line 23, Change "a the" to --the--.

In the Claims

In column 45 at line 62, In Claim 12, change "using" to --using an--.

In column 46 at line 53, In Claim 17, change "acoustic sensor assembly" to --method--.

Signed and Sealed this
Nineteenth Day of April, 2016

Michelle K. Lee
*Director of the United States Patent and Trademark Office*